US008501816B2

(12) United States Patent
Paterson et al.

(10) Patent No.: US 8,501,816 B2
(45) Date of Patent: Aug. 6, 2013

(54) ANTITUSSIVE COMPOSITIONS COMPRISING MEMANTINE

(75) Inventors: Blake Paterson, Baltimore, MD (US); Mark Ginski, Baltimore, MD (US); Brendan Canning, Ellicott City, MD (US)

(73) Assignee: Cerecor, Inc., Baltimore, MD (US)

( * ) Notice: Subject to any disclaimer, the term of this patent is extended or adjusted under 35 U.S.C. 154(b) by 0 days.

(21) Appl. No.: 13/272,031

(22) Filed: Oct. 12, 2011

(65) Prior Publication Data

US 2012/0121729 A1 May 17, 2012

Related U.S. Application Data

(60) Provisional application No. 61/392,291, filed on Oct. 12, 2010, provisional application No. 61/452,710, filed on Mar. 15, 2011, provisional application No. 61/392,250, filed on Oct. 12, 2010, provisional application No. 61/412,664, filed on Nov. 11, 2010, provisional application No. 61/412,660, filed on Nov. 11, 2010.

(51) Int. Cl.
*A61K 31/13* (2006.01)
*A61K 9/20* (2006.01)

(52) U.S. Cl.
USPC ........... 514/662; 514/663; 514/579; 514/849; 514/850; 424/435; 424/464; 424/465

(58) Field of Classification Search
None
See application file for complete search history.

(56) References Cited

U.S. PATENT DOCUMENTS

| | | | |
|---|---|---|---|
| 6,194,000 B1 | 2/2001 | Smith et al. | |
| 7,355,080 B2 | 4/2008 | Zhang et al. | |
| 7,462,743 B2 | 12/2008 | Merli et al. | |
| 7,619,007 B2 | 11/2009 | Went et al. | |
| 2002/0110578 A1* | 8/2002 | Pather et al. | 424/434 |
| 2006/0002999 A1* | 1/2006 | Yang et al. | 424/464 |
| 2006/0051416 A1 | 3/2006 | Rastogi et al. | |
| 2006/0252788 A1 | 11/2006 | Went et al. | |
| 2007/0065512 A1 | 3/2007 | Dedhiya et al. | |
| 2009/0004229 A1 | 1/2009 | Pastini et al. | |
| 2009/0004254 A1 | 1/2009 | Maibach | |
| 2009/0004281 A1 | 1/2009 | Nghiem et al. | |
| 2009/0110717 A1* | 4/2009 | Singh et al. | 424/448 |
| 2009/0186107 A1 | 7/2009 | Haber et al. | |
| 2009/0208576 A1 | 8/2009 | Gandhi et al. | |

(Continued)

FOREIGN PATENT DOCUMENTS

| | | |
|---|---|---|
| WO | 2004/039361 | 5/2004 |
| WO | 2006/096194 | 9/2006 |

(Continued)

OTHER PUBLICATIONS

Shojaei, Amir H., "Buccal Mucosa As a Route for Systemic Drug Delivery: A Review", J Pharm Pharmaceut Sci, 1(1):15-30, 1998.*

(Continued)

*Primary Examiner* — James H Alstrum Acevedo
*Assistant Examiner* — Monica Shin
(74) *Attorney, Agent, or Firm* — Cooley LLP

(57) ABSTRACT

Memantine compositions and methods of use are described herein. In some embodiments, the compositions comprise memantine and an absorption enhancer, or memantine and an elimination enhancer, or memantine and an absorption enhancer and an elimination enhancer.

16 Claims, 20 Drawing Sheets

U.S. PATENT DOCUMENTS

| | | |
|---|---|---|
| 2009/0208579 A1 | 8/2009 | Ueki et al. |
| 2009/0312361 A1 | 12/2009 | Streeper et al. |
| 2010/0016262 A1 | 1/2010 | Mehal et al. |
| 2010/0047342 A1 | 2/2010 | Went et al. |
| 2010/0074955 A1 | 3/2010 | Buschmann et al. |
| 2010/0105783 A1 | 4/2010 | Lee et al. |
| 2010/0260838 A1 | 10/2010 | Went et al. |
| 2010/0266684 A1 | 10/2010 | Went et al. |
| 2010/0272794 A1 | 10/2010 | Dumicic |
| 2010/0292341 A1 | 11/2010 | Sankar et al. |
| 2011/0045074 A1 | 2/2011 | Ueki et al. |

FOREIGN PATENT DOCUMENTS

| | | |
|---|---|---|
| WO | 2007/084818 | 7/2007 |
| WO | 2007/113856 | 10/2007 |
| WO | 2007/125533 | 11/2007 |
| WO | 2007/125545 | 11/2007 |
| WO | 2008/001341 | 1/2008 |
| WO | 2008/008120 | 1/2008 |
| WO | 2008/010794 | 1/2008 |
| WO | 2008/016602 | 2/2008 |
| WO | 2008/034815 | 3/2008 |
| WO | 2008/036798 | 3/2008 |
| WO | 2008/065339 | 6/2008 |
| WO | 2008/074816 | 6/2008 |
| WO | 2008/098195 | 8/2008 |
| WO | 2008/116165 | 9/2008 |
| WO | 2008/132712 | 11/2008 |
| WO | 2008/140459 | 11/2008 |
| WO | 2009/002084 | 12/2008 |
| WO | 2009/016486 | 2/2009 |

OTHER PUBLICATIONS

McNeil Consumer Products Company, "Chapter 4.A.3. McNeil 11.5-mg Zinc Gluconate Lozenge Study", pp. 1-3, <http://george-eby-research.com/html/hand_4a3.html>.*

Tox Wiki, "Memantine", pp. 1-5, <http://toxwiki.wikispaces.com/Memantine>.*

Canning, Brendan J., "Central Regulation of the Cough Reflex: Therapeutic Implications", Pulm. Pharmacol Ther. Apr. 2009, 22(2). pp. 75-81.*

"Namenda Product Insert; Last revised Jan. 2011".

* cited by examiner

Fig. 9: Memantine-pH dependent *in vitro* intestinal permeability (Caco-2 cells)

Fig. 10: Memantine-pH dependent ex vivo buccal permeability (porcine buccal mucosa)

ANTITUSSIVE COMPOSITIONS COMPRISING MEMANTINE

CROSS-REFERENCE TO RELATED APPLICATIONS

This application claims the benefit of U.S. Provisional Application Ser. No. 61/392,291, filed Oct. 12, 2010, U.S. Provisional Application Ser. No. 61/412,664, filed Nov. 11, 2010, U.S. Provisional Application Ser. No. 61/412,660, filed Nov. 11, 2010, U.S. Provisional Application Serial No. 61/392,250, filed Oct. 12, 2010, and U.S. Provisional Application Serial No. 61/452,710, filed on Mar. 15, 2011, each of which is herein incorporated by reference in its entirety for all purposes.

STATEMENT OF GOVERNMENTAL INTEREST

The subject matter of this application has been supported by research grants from the National Institutes of Health (NIH), Bethesda, Md., U.S.A. (Grant No. R01HL083192). The government may have certain rights to this invention.

BACKGROUND

Cough is the most common symptom for which patients seek medical advice from primary health care providers. Current antitussive therapies are minimally effective and have side effects that limit their utility. In the United States alone, over 2 billion dollars are spent annually on over the counter cough remedies with questionable efficacy, potential toxicity, and abuse potential, and billions more are spent annually in sick days and doctor's visits. Cough is the primary mechanism of transmission of airborne infections, including all forms of influenza, tuberculosis and *Bordetella pertussis*, the gram negative bacterium causing whooping cough. As such, cough represents a major public health issue that is poorly treated with currently existing therapies. Currently existing cough medications include dextromethorphan and codeine. People suffering from coughing, sneezing, rhinorrhea, and/or nasal obstruction generally take throat lozenges, cough syrups, and cough drops containing these medications for symptomatic relief. While such medications presently exist, there is room for significant improvement in the composition, efficacy, and adverse effect profiles of these medications.

Other medications currently in the market contain a combination of antitussives, for example one or more expectorants, mucolytics, decongestants, antipyretics, analgesics, or combinations thereof. While such combinations may be acceptable to some patients, others may have restrictions due to allergies or other incompatibilities with certain ingredients. Furthermore, many of these medications contain sugar or alcohol. Many patients suffering from cough would prefer medications that do not include sugar or alcohol. Moreover, the commonly used antitussive agent dextromethorphan has a potential for abuse and because of its lack of potency and side effects profile, has demonstrated limited efficacy in clinical trials. Therefore, there is a need for medications that treat/prevent coughing, sneezing, rhinorrhea, and/or nasal obstruction with fewer side effects, less drug abuse potential, free of sugar and added alcohol. This need is highlighted by the broad repercussions of acute cough on patient quality of life, school and work productivity, and public health resources. The available treatment options are limited and lack clinically proven efficacy and reliability to support their use. As such, there is an unmet need to develop new antitussive therapeutics. Specifically, new antitussive therapeutics that can provide rapid relief or suppression of cough with minimal or no side effects are particularly desirable.

Antitussive drugs may act peripherally to inhibit cough by suppressing the responsiveness of one or more vagal sensory receptors that produce cough (Spina et al., *Handb Exp Pharmacol.* 2009; (187): 155-186; Undem and Carr, *Chest,* 2010, 137(1): 177-184. Antitussive drugs may also act within the central nervous system at the level of the brain stem, where the basic neural circuitry responsible for cough is located (Bolser et al., *Respir Physiol Neurobiol.,* 2006; 152(3): 255-265; Canning, *Pulm Pharmacol Ther.* 2009; 22(2): 75-81). Specifically, centrally-acting antitussives are thought to inhibit cough by interfering with the central modulation of afferent signals from the periphery, thereby decreasing the sensitivity of the cough center located within the medulla to incoming stimuli. As an N-Methyl-d-aspartate (NMDA) glutamate receptor antagonist, dextromethorphan is thought to be a centrally-acting antitussive.

A recent model of the basic cough circuitry suggests that the eupneic respiratory pattern and the cough motor pattern are produced by essentially the same neural components. Although this pattern generator normally controls the breathing, its behavior is modified to produce cough by excitatory inputs from medullary second order interneurons mediating pulmonary C-fiber and cough receptor-afferent information. Centrally acting antitussive drugs may act at any level within this system. For example, these drugs could suppress the responsiveness of components of the central pathway by transmitting vagal sensory information (second-order interneurons) and/or can have more complex effects on the motor pattern generator for cough (Bolser et al., *Respir Physiol Neurobiol.,* 2006; 152(3): 255-265; Canning, *Pulm Pharmacol Ther.* 2009; 22(2): 75-81).

Memantine (MMT), (3,5-dimethyltricyclo[3.3.1.1$^{3,7}$]decan-1-amine or 3,5-dimethyladamantan-1-amine) is the first in a novel class of Alzheimer's disease medications acting on the glutamatergic system by blocking only open NMDA receptor ion channels. Unlike dextromethorphan and some other drugs with significant abuse potential, it does not interact with the enigmatic sigma receptor, partially explaining its lack of hallucinogenic effects. MMT has been used for some time in the elderly as a disease modifying agent and to improve the symptoms of moderate to severe Alzheimer's disease. Recent animal studies suggest that memantine may also be useful for pain treatment and protection against nerve cell damage (neuroprotection). MMT is currently approved for the treatment of moderate to severe Alzheimer's disease, and clinical experience has been remarkable for efficacy and minimal side effects and lack of abuse liability in this population.

BRIEF SUMMARY OF THE INVENTION

In its various embodiments, the antitussive compositions of the present invention comprise the combination of memantine and at least one absorption enhancer, memantine and at least one elimination enhancer, or memantine and at least one absorption enhancer and at least one elimination enhancer.

In other embodiments, the antitussive compositions of the present invention further comprise one or more additional pharmaceutically active ingredients, for example expectorants, mucolytics, decongestants, nasal decongestants, antihistamines, antipyretics, analgesics, opioids, and combinations thereof.

In further embodiments, the antitussive compositions of the present invention further comprise one or more excipients.

In still further embodiments, the antitussive compositions of the present invention comprise, consist of, or consist essentially of memantine, at least one absorption enhancer, and at least one excipient.

In yet further embodiments, the antitussive compositions of the present invention comprise, consist of, or consist essentially of memantine, at least one absorption enhancer, at least one additional pharmaceutically active ingredients selected from the group consisting of antitussives other than memantine, expectorants, decongestants, nasal decongestants, antihistamines, antipyretics, analgesics, and opioids, and at least one excipient.

In various embodiments, the present invention is further directed to methods of treating cough (e.g., acute, subacute, and chronic cough), comprising administering an antitussive composition comprising a therapeutically effective amount of memantine to a patient in need thereof. In particular embodiments of the method of the present invention, the antitussive composition further comprises one or more of an absorption enhancer, an elimination enhancer, or combinations thereof. In further embodiments, of the method of the present invention, the method further comprises administering a memantine-containing antitussive composition as described herein, which further comprises one or more additional pharmaceutically active ingredients, for example expectorants, mucolytics, decongestants, nasal decongestants, antihistamines, analgesics, antipyretics, opioids, and combinations thereof.

DETAILED DESCRIPTION OF THE INVENTION

Figure 1:
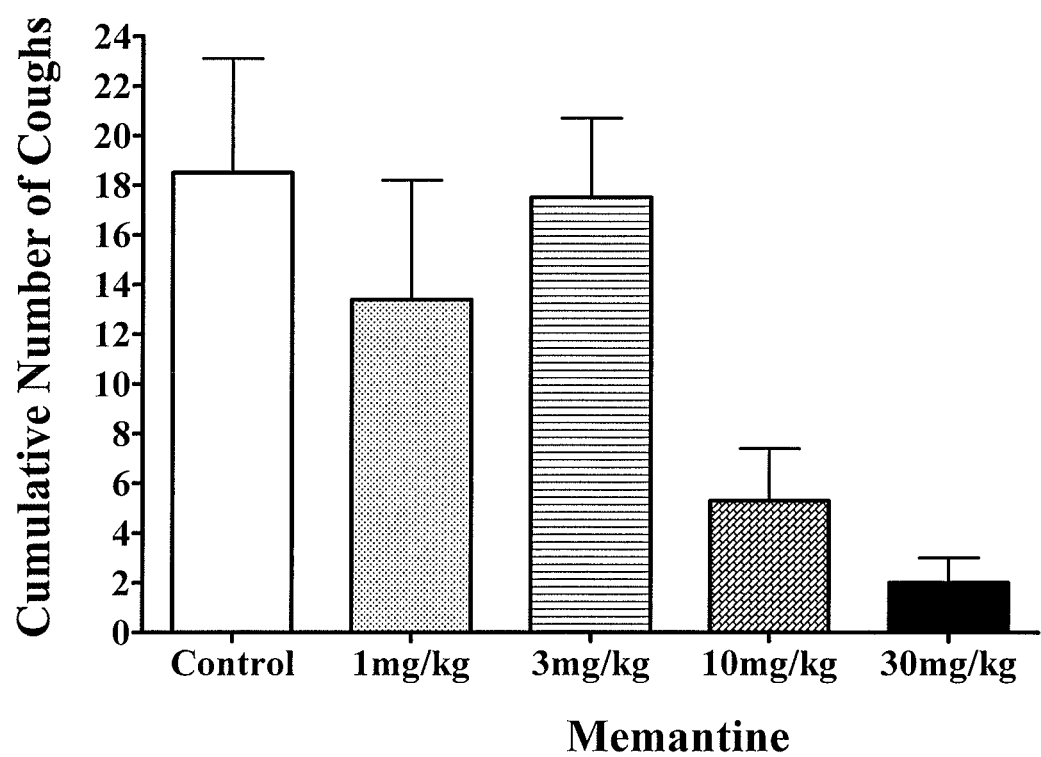
FIG. 1: Cumulative numbers of coughs (presented as mean±sem) in response to citric acid aerosols (0.01-0.3M) in control animals compared with increasing doses of memantine, administered intraperitoneally. Compared to controls 10 mg/kg and 30 mg/kg memantine both significantly reduced the cumulative number of coughs evoked by citric acid ($p<0.02$).

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

The term "memantine" as used herein refers to memantine as well as any pharmaceutically acceptable salts thereof (e.g., memantine hydrochloride or other salts as described herein).

The term "antitussive" broadly refers to agents or compositions which are capable of relieving, suppressing, or reducing the frequency of coughing.

The term "pharmaceutically acceptable" means biologically or pharmacologically compatible for in-vivo use in animals or humans, and can mean approved by a regulatory agency of the Federal or a state government or listed in the U.S. Pharmacopeia or other generally recognized pharmacopeia for use in animals, and more particularly in humans.

The term "$C_{max}$" refers to the maximum (or peak) concentration that a drug achieves in the blood plasma after the drug has been administrated and prior to the administration of a second dose.

The term "$T_{max}$" refers to the time after dosing at which the maximum or peak concentration of a drug in the blood plasma is achieved after administration of the drug.

The term "AUC" refers to the area under the time/plasma concentration curve after administration of a drug. Total "exposure" of the body of a patient to a drug is often estimated by the AUC.

The term "$t_{1/2}$" or "$T_{1/2}$" refers to the elimination half-life of a drug (i.e., the time required for elimination of half of the peak amount of drug from the body after administration.

The term "expectorant" refers a compound that works by signaling the body to increase the amount or hydration of secretions, resulting in more yet clearer secretions and as a byproduct lubricating the irritated respiratory tract. The term "mucolytic" refers to a compound which dissolves thick mucus and is usually used to help relieve respiratory difficulties. It does so by dissolving various chemical bonds within secretions, which in turn can lower the viscosity by altering the mucin-containing components. Both expectorants and mucolytics aid in the clearance of mucous from the airways, lungs, bronchi, and trachea.

The term "antipyretic" refers to compounds which reduced fever. Common antipyretics such as aspirin, NSAID such as ibuprofen, naproxen sodium, ketoacetominophen, etc. also have analgesic effects, and may also be referred to as an analgesic/antipyretic or antipyretic/analgesic.

Pharmaceutically acceptable salts include those obtained by reacting the active compound (e.g., memantine), functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The following are further examples of acid salts that can be obtained by reaction of the active compound (e.g., memantine) with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates. For example, the pharmaceutically acceptable salt can be a hydrochloride salt, a hydrobromide salt or a mesylate salt. In one embodiment, the pharmaceutically acceptable salt is a hydrochloride salt.

Antipyretics/analgesics are agents that inhibit the cyclooxygenase system centrally and thus possess antipyretic and analgesic properties. Examples include acetaminophen, aspirin and non-steroidal anti-inflammatory agents such as ibuprofen and naproxen.

The term "cognitive impairment" means the impairment of thinking, memory, and executive functions that are associated with temporary or permanent brain dysfunction. Their main symptoms include problems with memory, orientation, language, information processing, and the ability to focus and sustain attention on a task. Cognitive impairment may include, for example, impairment from CNS disorders or conditions that fall within the scope of the present invention include, but are not limited to, age-associated memory impairment (AAMI); mild cognitive impairment (MCI), delirium (aka acute confusional state); dementia (sometimes further classified as Alzheimer's or non-Alzheimer's type dementia); Alzheimer's disease; Parkinson's disease; Huntington's disease (aka chorea); mental retardation; (e.g., Rubenstein-Taybi and Downs Syndrome); cerebrovascular disease (e.g., vascular dementia, post-cardiac surgery); affective disorders; psychotic disorders; autism (aka Kanner's Syndrome); neurotic disorders; attention deficit disorder (ADD); subdural hematoma; normal-pressure hydrocephalus; brain tumor; head trauma (postconcussional disorder) and brain trauma. Cognitive impairment may be impairment caused from a drug. For example, a drug that causes drowsiness, sedation, dizziness or any other symptom that creates problems with memory, orientation, language, information processing, and the ability to focus and sustain attention on a task, may cause "cognitive impairment."

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "acute cough" means a condition of sporadic or persistent coughing in a patient for a time period up to about three weeks.

The term "subacute cough" means a condition of sporadic or persistent coughing in a patient for a time period between about three and about eight weeks.

The term "chronic cough" means a condition of sporadic or persistent coughing in a patient for a time period greater than about eight weeks.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof. As used herein with respect to the pharmaceutical formulations comprising memantine, or a pharmaceutically acceptable salt thereof, e.g., memantine hydrochloride, the term "therapeutically effective amount/dose" refers to the amount/dose of the compound that is sufficient to produce an effective response upon administration to a patient.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation. Alternatively, "about" can mean plus or minus a range of up to 20%, up to 10%, or up to 5%.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

As used herein, an "absorption enhancer" means an agent that enhances/increases the absorption rate of memantine in various embodiments of compositions of the present invention, relative to the absorption rate of memantine in compositions comprising memantine lacking such absorption enhancers (using methods for measuring absorption rate known in the art). "Permeation enhancer" as used herein, refers to an agent that enhances/increases the permeation of memantine in various embodiments of composition of the present invention relative to the permeation of memantine in compositions comprising memantine lacking such permeation enhancers (using methods for measuring permeation known in the art). "Elimination enhancer" as used herein, means an agent that enhances/increases the elimination rate of memantine in various embodiments of compositions of the present invention relative to the elimination rate of memantine in compositions comprising memantine lacking such elimination enhancers (using methods for measuring elimination rate known in the art). In some embodiments, the "absorption enhancer" or "permeation enhancer" or the "elimination enhancer" decreases the Tmax of memantine, for example to less than about 6 hours, 5 hours or 4 hours. These agents can be any agent known in the skill of art.

In the compositions of the present invention, memantine can be used in the form of the free-base, or in the form of a pharmaceutically acceptable salt. Suitable salts of memantine include, but are not limited to, the acid addition salts disclosed herein. In a particular embodiment, the salt is memantine hydrochloride. All of these salts (or other similar salts) may be prepared by conventional means. All such salts are acceptable provided that they are non-toxic and do not substantially interfere with the desired pharmacological activity.

The following description includes information that may be useful in understanding the present invention. It is not an admission that any of the information provided herein is prior art or relevant to the presently claimed inventions, or that any publication specifically or implicitly referenced is prior art.

Memantine Anti-Tussive Effects

Cough can be a symptom of a specific disease/disorder. When the specific disease is known, symptomatic cough can be treated with specific agents that treat the disease. However, in most instances, the underlying pathophysiology of cough is not known. In such instances, the symptomatic cough can be reduced by using non-specific cough suppressants that are intended to reduce coughing regardless of etiology.

In particular, the use of cough suppressants is typically for a short-term basis for symptomatic relief of cough. The use of these drugs is most appropriate when (1) the etiology of cough is unknown (precluding the use of specific therapy), (2) the specific therapy requires a period of time before it can become effective, or (3) the specific therapy will be ineffective, such as in patients with inoperable lung cancer. As such, the majority of cough episodes require the use of non-specific cough suppressants that reduce the cough frequency regardless of the underlying disease.

It is highly desirable to develop cough suppressants that give rapid cough relief with minimum or no side effects, less patient variability, and no abuse potential/addictive properties. None of the currently available cough therapies can achieve these results. For example, the relatively few drugs that suppress cough by action on mucociliary factors cannot suppress cough consistently. In fact, a relatively few drugs, albeit with various side effects, are effective for the non-specific suppression of cough (Bolser, D. C. *Chest* 2006, 129; 238S-249S).

The present inventors have found that memantine is an extremely effective antitussive, as demonstrated herein, for example, in animal models of cough, and is believed to act by suppressing the cough reflex in the medulla. In particular, the present inventors have found that, surprisingly and unexpectedly, orally administered memantine is more potent than parenterally administered memantine in its antitussive effects. The $T_{max}$ for conventional oral tablets of memantine (i.e., Namenda®) ranges from 4-6 hours in healthy volunteers, while the terminal elimination half life is 60 hours. Linear pharmacokinetics are observed over the therapeutic dose range. At steady state, plasma memantine concentrations of conventional memantine dosage forms range from 70-150 ng/mL, with large inter-individual differences. The mean volume of distribution is about 10 L/kg, and about 45% of the drug is bound to plasma proteins. Memantine and its three active metabolites are primarily excreted by the kidneys. Total renal clearance in healthy volunteers is approximately 170 mL/min/1.70 m². With urine acidification, the renal clearance of memantine exceeds the glomerular filtration rate.

While it has been suggested that the NMDA receptor antagonist memantine might be effective as an antitussive (Canning, *Pulm Pharmacol Ther.* 2009 April; 22(2): 75-81), until the present invention, this suggestion has remained entirely hypothetical, and there has not been any demonstration that memantine does, in fact, have antitussive properties, nor has there been any disclosure of compositions comprising memantine formulated for treating cough, doses of memantine suitable for antitussive applications, methods of administration (e.g., oral, buccal, parenteral, etc.), or methods of treating cough using memantine. Furthermore, since it is known that not all NMDA receptor antagonists have antitussive properties, without the experimental demonstration of antitussive activity, it is not possible to infer that a particular NMDA receptor antagonist would, in fact, be useful as an antitussive, at any dose. For example, the potent NMDA receptor antagonist ketamine was reported to be ineffective in chronic cough patients (Young et al., *Am J Respir Crit. Care Med* 181; 2010: A5906, *COUGH, PFT AND INTERESTING CASE REPORTS IN AIRWAY DISEASE*, "Does Central Up-regulation Of The N-Methyl-D-Aspartate Receptor Contribute To Cough Reflex Hypersensitivity?"). Similarly, the NMDA receptor blocker dextromethorphan was found to be ineffective in treating cough associated with upper respiratory tract infections (Bolser, D. C. *Chest* 2006, 129; 238S-249S).

The present inventors have found that when administered systemically, memantine (MMT) is a surprisingly, and unexpectedly extremely effective antitussive, unlike other NMDA antagonists. As demonstrated in animal models of cough, the present inventors believe that memantine appears to act centrally by suppressing the cough reflex in the medullary brainstem. Memantine acts in a manner distinct from that of opioids (e.g., codeine), to elevate the threshold for coughing, likely via inhibition of cation flux across the activated NMDA receptor. When compared to the currently approved antitussive dextromethorphan, codeine, and first generation antihistamines, the present inventors have found that memantine provides an unexpectedly and very significantly improved antitussive effect, with tolerability and less potential for abuse. In particular, the present inventors have found that memantine is significantly and unexpectedly more potent than dextromethorphan, yet does not inhibit NMDA receptors at low levels of glutamate activity, like dextromethorphan (Lipton, *Nat Rev Neurosci.*, 2007 October; 8 (10): 803-8. Review. Erratum in: *Nat Rev Neurosci.*, 2007 November; 8 (11): 2p following 903. Chen et al., *J Neurochem.*, 2006 June; 97 (6): 1611-26). Furthermore, and unlike conventional antitussives such as dextromethorphan, memantine is effective as an antitussive at doses at which dextromethorphan is not only ineffective, but is also highly sedating (see FIG. 20).

In addition, the present inventors have found that combinations of memantine with other antitussives such as guaifenesin, diphenhydramine, ambroxol, and benzonatate provide synergistic antitussive effects. Treatment with the compositions of the present invention relieves cough frequency without abolishing the protective cough reflex.

Thus, as disclosed herein, the present inventors have found that memantine unexpectedly provides superior potency and efficacy compared to conventional antitussives such as dextromethorphan, diphenhydramine, menthol, guaifenesin, ambroxol, and benzonatate, particularly in view of the lack of antitussives activity found for, e.g. dextromethorphan. In addition, as disclosed herein the present inventors have found that memantine surprisingly and unexpectedly provides an antitussive effect at doses that produce no sedation or quantifiable side effects of any kind, whereas conventional NMDA antagonists such as ketamine and dextromethorphan produces substantial side effects at doses that actually fail to inhibit cough. Furthermore, conventional memantine formulations (such as Namenda®) provide insufficiently rapid cough relief, due to a relatively long memantine Tmax of nearly 8 hours. As described herein, the compositions of the present invention provide much shorter memantine Tmax values (e.g., less than about 3 hours), which is optimal for antitussive therapy. In addition, the present inventors have found that combining memantine with one or more additional active agents, such as diphenhydramine, ambroxol, guaifenesin, and benzonatate provide synergistic antitussives affects, providing greater antitussive efficacy at sufficiently low doses of the additional active agents, whereby side effects are substantially reduced or eliminated.

Given the ~100% bioavailability of memantine, one would not expect that improved clinical efficacy would be provided by increasing the already high rate of uptake of memantine. However, the present inventors have found that providing higher $C_{max}$ and lower exposure (AUC) of memantine compared to conventional memantine formulations, such as Namenda®, is desirable for treating cough. This is an unexpected finding, as generally, formulations with higher $C_{max}$ generally provide higher exposure (i.e., higher AUC values). Furthermore, higher exposure is generally associated with greater clinical effect. However, in various embodiments, the memantine-containing compositions of the present invention include one or more absorption enhancers (to provide a higher $C_{max}$) and/or one or more elimination enhancers (to reduce exposure), and provide rapid and effective treatment of cough. In one embodiment, the compositions of the present invention provide rapid cough relief, e.g., for acute cough. Rapid cough relief can be provided by increasing the rate of absorption of memantine (e.g., by decreasing the $T_{max}$) compared to conventional memantine compositions. One aspect of the present invention is to provide memantine compositions wherein the $T_{max}$ for memantine after administration of the compositions of the present invention is less than 8 hours, less than 7 hours, less than 6 hours, less than 5 hours, less than 4 hours, less than 3 hours, less than 2 hours, less than 1 hour, less than 45 minutes, less than 30 minutes, or less than 15 minutes, inclusive of all ranges therebetween. In some other embodiments, the $T_{max}$ of memantine is about 15 min, about 30 min, about 45 min, about 1 hour, about 2 hours, about 3 hours, about 4 hours, about 5 hours, about 6 hours, about 7 hours, or about 8 hours, inclusive of all ranges therebetween.

In particular embodiments, the $T_{max}$ of memantine after administration of the compositions of the present invention ranges from about 15 minutes to about 2 hours, about 15 minutes to about 1 hour, about 30 minutes to about 2 hours, about 45 minutes to about 2 hours, about 1 hour to about 2 hours, about 1 hour to about 2.5 hours, about 1 hour to about 3 hours, about 1 hour to about 4 hours, or about 1 hour to about 6 hours. etc. In some other embodiments, the $T_{max}$ of memantine after administration of the compositions of the present invention ranges from about 2 hours to 2.5 hours, about 2 hours to about 3 hours, about 2 hours to about 3.5 hours, about 2 hours to about 4 hours, about 2 hours to about 4.5 hours, about 2 hours to about 5 hours, about 2 hours to about 5.5 hours, about 2 hours to about 6 hours. In other embodiments, $T_{max}$ of memantine after administration of the compositions of the present invention ranges from about 2.5 hours to about 3 hours, about 2.5 hours to about 3.5 hours, about 2.5 hours to about 4 hours, about 2.5 hours to about 4.5 hours, about 2.5 hours to about 5 hours, about 2.5 hours to about 5.5 hours, about 2.5 hours to about 6 hours. In one embodiment of the invention, the $T_{max}$ of memantine after administration of the compositions of the present invention ranges from about 3 hours to about 3.5 hours, about 3 hours to about 4 hours, about 3 hours to about 4.5 hours, about 3 hours to about 5 hours, about 3 hours to about 5.5 hours, or about 3 hours to about 6 hours. In another embodiment of the invention, the $T_{max}$ of memantine after administration of the compositions of the present invention ranges from about 3.5 hours to about 4 hours, 3.5 hours to about 4.5 hours, about 3.5 hours to about 5 hours, about 3.5 hours to about 5.5 hours, or about 3.5 hours to about 6 hours. In some embodiments of the invention, the $T_{max}$ of memantine after administration of the compositions of the present invention ranges from about 4 hours to about 4.5 hours, about 4 hours to about 5 hours, about 4 hours to about 5.5 hours, or about 4 hours to about 6 hours.

In a particular embodiment of the invention, the $T_{max}$ of memantine ranges between about 15 minutes to 30 minutes, about 15 minutes to about 45 minutes, about 15 minutes to about 1 hour, about 15 minutes to about 1.5 hours, about 15 minutes to about 2 hours or about 15 minutes to about 2.5 hours.

In some embodiments of the invention, the elimination half-life ($t_{1/2}$) of the memantine in the present compositions is less than about 80 hours, less than about 70 hours, less than about 65 hours, less than about 60 hours, less than about 55 hours, less than about 50 hours, less than about 45 hours, less than about 40 hours, less than about 35 hours, less than about 30 hours, less than about 25 hours, less than about 24 hours, less than about 22 hours, less than about 20 hours, less than about 18 hours, less than about 16 hours, or less than about 12 hours, inclusive of all ranges and subranges therebetween.

In some embodiments of the invention, total clearance of the memantine in present compositions is more than about 180 mL/min, more than about 185 mL/min, more than about 190 mL/min, more than about 195 mL/min, or more than about 200 mL/min.

In another embodiment, after administration the compositions of the present invention provide an $AUC_\infty$ for memantine of about 120 to 18,000 ng-hr/mL, for example about 120, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, about 2000, about 2200, about 2400, about 2600, about 2800, about 3000, about 3200, about 3400, about 3600, about 3800, about 4000, about 4200, about 4400, about 4600, about 4800, about 5000, about 5200, about 5400, about 5600, about 5800, about 6000, about 6200, about 6400, about 6600, about 6800, about 7000, about 7200, about 7400, about 7600, about 7800, about 8000, about 8200, about 8400, about 8600, about 8800, about 9000, about 9200, about 9400, about 9600, about 9800, about 10,000, about 10,500, about 11,000, about 11,500, about 12,000, about 12,500, about 13,000, about 13,500, about 14,000, about 14,500, about 15,000, about 15,500, about 16,000, about 16,500, about 17,000, about 17,500, or about 18,000 ng-hr/mL, inclusive of all ranges and subranges therebetween.

In various embodiments, after administration of the memantine-containing compositions of the present invention, the $C_{max}$ of memantine ranges (after single administration) from about 10 ng/mL to about 50 ng/mL, for example about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, about 26 ng/mL, about 27 ng/mL, about 28 ng/mL, about 29 ng/mL, about 30 ng/mL, about 31 ng/mL, about 32 ng/mL, about 33 ng/mL, about 34 ng/mL, about 35 ng/mL, about 36 ng/mL, about 37 ng/mL, about 38 ng/mL, about 39 ng/mL, about 40 ng/mL, about 41 ng/m, about 42 ng/mL, about 43 ng/mL, about 44 ng/mL, about 45 ng/mL, about 46 ng/mL, about 47 ng/mL, about 48 ng/mL, about 49 ng/mL, or about 50 ng/mL, inclusive of all ranges therebetween.

The present inventors have found that in the compositions of the present invention, both $C_{max}$ and AUC are dose proportional. Thus, in some embodiments, for memantine compositions of the present invention, the dose normalized oral or buccal $C_{max}$ (normalized to a 1 mg dose) ranges from about 1 ng/mL to about 2 ng/mL, for example about 1, about 1.1, about 1.2, about 1.3, about 1.4, about 1.5, about 1.6, about 1.7, about 1.8, about 1.9, or about 2 ng/mL (per 1 mg dose), inclusive of all ranges and subranges therebetween; and the $T_{max}$ ranges from about 3.5 to about 9.5 hours, for example about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about a six, about 6.1, about 6.2, about 6.3, about 6.4, about 6.5, about 6.6, about 6.7, about 6.8, about 6.9, about seven, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, about 9, about 9.1, about 9.2, about 9.3, about 9.4, or about 9.5 hours, inclusive of all ranges and subranges therebetween.

In other embodiments, the combination of memantine and a permeation enhancer increase the buccal or oral $C_{max}$ and decreases the $T_{max}$. For example, the combination of memantine, a permeation enhancer, and optionally a urinary acidifying agent reduces the $T_{max}$ to about 0.5 to about 1.5 hours, including about 0.5, about 0.6, about 0.7, about 0.8, about 0.9, about 1, about 1.1, about 1.2, about 1.3, about 1.4, or about 1.5 hours inclusive of all ranges and subranges therebetween; and the dose normalized $C_{max}$ increases to a range of about 2.5 to about 4.5 ng/mL (normalized to a 1 mg dose), including about 2.5, about 2.6, about 2.7, about 2.8, about 2.9, about 3, about 3.1, about 3.2, about 3.3, about 3.4, or about 3.5 ng/mL, inclusive of all ranges and subranges therebetween.

In still other embodiments, the addition of a permeation enhancer and an optional urinary acidifying agent to memantine-containing compositions reduces the dose-normalized $AUC_\infty$ from about 80-150 ng-hr/mL (per 1 mg dose for memantine-containing compositions without a permeation enhancer and an optional urinary acidifying agent) to about 30-60 ng-hr/mL (per 1 mg dose), for example an $AUC_\infty$ of about 30, about 35, about 40, about 45, about 50, about 55, or about 60 ng-hr/mL (per 1 mg dose), inclusive of all ranges and subranges therebetween.

NMDARs are involved in many diverse roles in the central nervous system including synaptic transmission, synaptic plasticity, neuronal protection and survival. NMDARs are glutamate gated ion channels, consisting of four subunits, typically two NR1 subunits and two NR2 subunits, surrounding a central channel pore. The NR1 subunits are obligatory for functionality and can combine with four different NR2 (A-D) and two different NR3 (A and B) subunits. Subunit expression varies during development and with location. In the inactive state, the channel pore is blocked by $Mg^{2+}$. Partial membrane depolarization is sufficient to relieve this blockade, allowing the influx of $Na^+$ and also $Ca^{2+}$. NMDARs possess multiple extracellular binding sites, allowing a variety of molecules to modulate their function.

Like dextromethorphan, memantine (used clinically to treat moderate to severe Alzheimer's disease) is a low affinity, uncompetitive NMDAR blocker, binding preferentially to open NMDA receptor channels. However, memantine blocks only activated receptors, providing higher levels of blockade in the presence of high concentrations of glutamate and lower levels of blockade during normal physiological transmission.

This mode of action may explain why memantine treatment is well tolerated by patients; a recent review suggested adverse effects were reported in <10% of those treated for dementia. Unlike dextromethorphan, memantine does not interact with the enigmatic sigma receptor, an interaction that is known to cause hallucinogenic effects in humans.

The results presented in the present application provide the first evidence that memantine has antitussive activity with significant inhibition of both citric acid and bradykinin induced cough in guinea pigs. The degree of inhibition provided by memantine was similar to that seen with baclofen but without the associated sedation, and comparably was significantly more effective than high doses of other NMDAR antagonists. Receptor subunit expression suggested the presence of NMDARs in both the central and peripheral tissues involved in the cough reflex.

Coughing is known to be initiated by activation of vagal afferent fibers in the larynx and large airways, via acid and mechanically sensitive M fibers, and by activation of capsaicin-sensitive C fibers that are also responsive to acid (via the TRPV1 channels) and bradykinin. These fibers terminate in the nucleus Tractus Solitarius (nTS), where microinjection of NMDAR antagonists has been shown to significantly inhibit coughing in response to citric acid. The effect of memantine on both bradykinin and citric acid evoked cough is consistent with inhibition of the C-fiber pathway but an additional effect on Aδ-fibers cannot be excluded.

NMDAR subunit gene expression was detected in the nTS, the primary site of vagal afferent termination in the brainstem, but also in vagal ganglia. The latter finding supports the notion that NMDARs may be present in the airway nerve terminals and/or may modulate neurotransmitter release presynaptically in the CNS.

Figure 20:
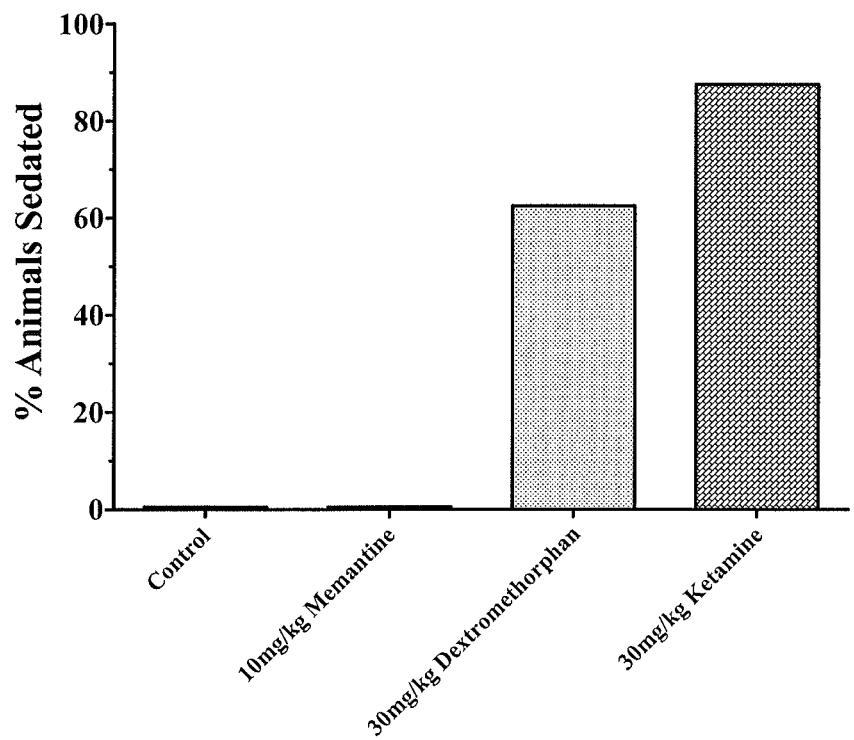
FIG. 20: At doses that failed to inhibit citric acid evoked coughing (see FIG. 19), both dextromethorphan and ketamine produced moderate to severe sedation in the majority of animals studied. By contrast, memantine administered at one-third the dose of dextromethorphan and ketamine (10 mg/kg) inhibited citric acid evoked coughing (FIG. 19) but induced no sedation.

Although NMDARs are reported to be mechanically sensitive and PCR studies are consistent with a peripheral expression of NMDARs by vagal afferents, a central site of action for memantine seems most likely, especially as the antitussive effects of dextromethorphan are absent when delivered to the airway. Nevertheless, memantine treatment did not obviously cause sedation or suppress respiration at doses that almost completely inhibited coughing. This may be a consequence of the use-dependent action of memantine and NMDAR specificity at the doses used in this study. The selective effects of memantine on cough might also be explained by its greater affinity for NMDAR subtypes or effects at extra-synaptic NMDARs. In contrast, high doses of dextromethorphan and ketamine, did not suppress coughing as effectively as memantine, despite clear evidence of sedation (FIG. 20). Perhaps the relative lack of side effects seen with memantine treatment is attributable to its inability to interact with the additional targets for dextromethorphan and ketamine (e.g. Sigma-1 receptors, HCN1 channels).

Other properties of NMDARs provide circumstantial evidence for a role in modulating the cough reflex. Females have a more sensitive cough reflex than males when challenged with inhaled irritants and have higher frequency of coughing when suffering from chronic cough. Estrogens have significant influence on NMDARs. In the hippocampus, elevated estradiol levels are associated with increased synaptic receptor density, increased transmission and an enhanced long term potentiation. Furthermore, cross-organ sensitization between the uterus and urethra is mediated by phosphorylation of NR2B subunits and modulated significantly by the estrous cycle. Such NMDAR dependent interactions between organs may be analogous to the coughing associated with extrapulmonary disorders such as gastrooesophageal reflux disease.

In Vivo Reduction of Citric Acid or Bradykinin Challenged Cough

Memantine is effective in suppressing/reducing cough. Intraparenteral administration of memantine (10 mg/kg) was found to be effective in reducing cumulative coughs evoked by citric acid in guinea pigs (Table 1). Table 1 shows that the antitussive effect was observed when memantine was given 0.5-2.0 hr prior to the citric acid challenge. Antitussive effect was no longer observed when the guinea pigs were treated 4 hrs prior to the citric acid challenge. This is consistent with known pharmacokinetics of memantine administered intraparenterally to animals, where reduced plasma levels are observed at 4 hrs.

TABLE 1

Cumulative coughs evoked by citric acid in control and MMT pre-treated animals - intraperitoneal administration

| Treatment | 0.1M Citric Acid | 0.3M Citric Acid | n |
| --- | --- | --- | --- |
| Control (saline) | 7 ± 3 | 16 ± 5 | 12 |
| MMT pre-challenge timing | | | |
| 0.5 hr | 2 ± 2 | 5 ± 3 | 8 |
| 1 hr | 1 ± 1 | 7 ± 3 | 6 |
| 2 hr | 0 ± 0 | 7 ± 4 | 3 |
| 4 hr | 6 ± 5 | 15 ± 6 | 4 |

Table 2 shows the dose-response data of orally administered memantine (0.01, 0.1, 1, 3, 10, and 30 mg/kg) to conscious guinea pigs at 1 hour pre-citric acid cough challenge. In the control group, 6 out of 16 guinea pigs had ≧15 cumulative coughs. With the increase in memantine dose from 0.01 to 30 mg/kg, none of the guinea pigs had ≧15 cumulative coughs. The mean cumulative coughs were reduced from 12±2 (control) to 5±1 (memantine 10 mg/kg). Surprisingly and unexpectedly, Table 2 shows that orally administered memantine appears to be more potent than parenterally administered memantine (i.e., Tables 1, 3).

TABLE 2

Dose response data of orally administered memantine to conscious guinea pigs

| Dose (po) | ≧15 Cumulative coughs/total number of guinea pigs |
| --- | --- |
| Control (saline) | 6/16 |
| 0.01 mg/kg MMT | 2/5 |
| 0.1 mg/kg MMT | 1/5 |
| 1 mg/kg MMT | 2/7 |
| 3 mg/kg MMT | 0/5 |
| 10 mg/kg MMT | 0/7 |
| 30 mg/kg MMT | 0/4 |

The antitussive effect of intraparenteral administration of memantine was similar in citric acid-induced cough in the guinea pig cough model (Table 3). Mean cumulative cough was reduced to 1.3±0.8 (10 mg/kg) from 15±4 (control).

TABLE 3

Antitussive effects of intraperitoneally-administered MMT (i.p. 1 hour pre-bradykinin challenge) in conscious guinea pigs challenged with bradykinin

| Treatment | 0.3M bradykinin challenge | n |
|---|---|---|
| Control (saline, i.p.) | 15 ± 4 | 12 |
| MMT 10 mg/kg | 1.3 ± 0.8 | 5 |
| MMT 3 mg/kg | 20 ± 5 | 6 |

It is also possible to combine memantine with other cough suppressants to exert a synergistic cough reduction effect. Table 4 shows the cough reduction effects of potential synergistic agents on citric acid-induced cough in the guinea pig cough model. The study demonstrated that orally administered menthol (100 mg/kg) and diphenhydramine (30 and 100 mg/kg) reduced coughs in a citric acid-induced cough model in guinea pigs. Orally administered ambroxol (100 mg/kg) and benzonatate (30 mg/kg) were also effective in reducing coughs while no apparent effect on cough was observed with orally administered guaifenesin at 50 or 100 mg/kg. Unlike memantine, none of these cough suppressants were effective at dosages around 10 mg/kg. Menthol was effective only at 100 mg/kg (mean cumulative cough reduction of 11±2 from 20±3 (control)).

TABLE 4

Evaluation of potentially synergistic agents on citric acid-induced cough in the guinea pig cough model

| Dose (po) | ≧15 Cumulative coughs/total number of guinea pigs | Mean ± sem cumulative coughs |
|---|---|---|
| Control (saline) | 7/10 | 20 ± 3 |
| Ambroxol 100 mg/kg | 2/6 | 13 ± 4 |
| Diphenhydramine 10 mg/kg | 3/3 | 25 ± 5 |
| Diphenhydramine 30 mg/kg | 2/6 | 12 ± 2 |
| Diphenhydramine 100 mg/kg | 0/5 | 5 ± 1 |
| Benzonatate 10 mg/kg | 3/3 | 24 ± 4 |
| Benzonatate 30 mg/kg | 2/5 | 13 ± 4 |
| Guaifenesin 50 mg/kg | 3/3 | 30 ± 1 |
| Guaifenesin 100 mg/kg | 3/4 | 20 ± 5 |
| Menthol 30 mg/kg | 3/3 | 21 ± 3 |
| Menthol 100 mg/kg | 1/7 | 11 ± 2 |

Although conventional memantine compositions have oral bioavailability of greater than 100%, in order to effectively treat cough, it would be desirable to reach maximum plasma concentration of memantine in a much shorter time (i.e., reduce $T_{max}$) to provide an immediate reduction in cough frequency, while dose proportionally reducing exposure in order to prevent side effects and maximize safety. In contrast to conventional memantine formulations, the memantine compositions of the present invention increase the absorption of memantine at local absorption sites and thereby effectively decrease the $T_{max}$, resulting in systemic exposures less than or equal to exposure from conventional memantine compositions.

As described herein, for the treatment of cough in a patient, the present invention in various embodiments is directed to compositions comprising, consisting of, or consisting essentially of memantine, and methods of treating cough with such compositions. In other embodiments, the compositions of the present invention further comprise, consist of, or consist essentially of memantine in combination with one or more absorption or permeation enhancing agents (e.g., one or more of the absorption or permeation enhancing agents disclosed herein) and methods of treating cough with such compositions. In still other embodiments, the compositions of the present invention further comprise, consist of, or consist essentially of memantine in combination with one or more urinary acidifying agents (e.g., one or more of the urinary acidifying agents disclosed herein) and methods of treating cough with such compositions. In still other embodiments, the compositions of the present invention further comprise, consist of, or consist essentially of memantine in combination with one or more absorption or permeation enhancing agents (e.g., one or more of the absorption or permeation enhancing agents disclosed herein) and one or more urinary acidifying agents (e.g., one or more of the urinary acidifying agents disclosed herein) and methods of treating cough with such compositions.

In various embodiments, formulations of the present invention that accelerate memantine absorption, uptake or elimination are advantageous. Conventional memantine formulations are not suitable for such treatments because they are designed to delay memantine release and elimination because of the specific pharmacokinetic profile of memantine (for example 100% bioavailability). In contrast, the various embodiments of formulations of the present invention that accelerate the absorption of memantine would enable its use as an antitussive agent and also in other acute indications. In some embodiments of the present invention, the inventive memantine compositions provide faster attainment of therapeutic blood levels of memantine (shorter time to peak blood levels, $T_{max}$, of memantine) compared to conventional memantine formulations (e.g., Namenda®). In other embodiments, the compositions of the present invention provide more rapid terminal elimination of memantine (shorter $t_{1/2}$), compared to conventional memantine compositions. In still other embodiments, the compositions of the present invention provide both shorter $T_{max}$ and shorter $t_{1/2}$ for memantine compared to conventional memantine formulations. Faster attainment of therapeutic blood levels of memantine (shorter $T_{max}$) and shorter terminal elimination ($t_{1/2}$) of memantine can be achieved using various formulations of the present invention as described herein.

Absorption/Elimination Enhancing Excipients

1. Alkalization of Local pH in Upper GI Tract or Buccal Mucosa

In the compositions of the present invention, specific excipients are provided that enhance the absorption of memantine at the site of absorption. These excipients act by manipulating the microenvironment of the site of absorption. In particular embodiments, these excipients include agents that can increase the concentration of the non-ionized form of memantine by increasing the local pH at the site of absorption. In the compositions of the present invention, agents that increase local pH can be added or administered in quantities sufficient to achieve at least pH of 7 at the site of absorption, or advantageously sufficient to achieve a pH of 10 or more within the microenvironment of the site of absorption.

Figure 10:
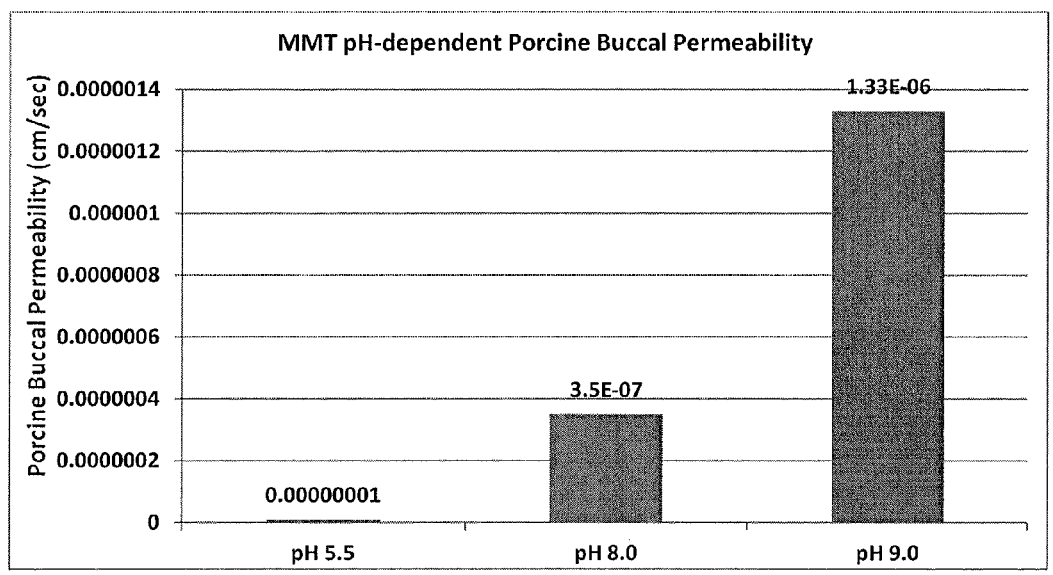
FIG. 10: Memantine-pH dependent ex vivo buccal permeability (porcine buccal mucosa).

Memantine is completely ionized at around pH 6.0. Increasing the pH (alkalization) should reduce the level of ionization of memantine, thus increasing its permeability through the epithelium of the digestive tract, as shown by its permeability through Caco-2 cells. The permeability of memantine in Caco-2 cells gradually increases with an increase in pH from pH 5.0 to 10.5. Similarly, it was found that an increase in pH from 5.5 to 9.0 resulted in an over 100-fold increase in permeability of memantine in porcine buccal mucosa (FIG. 10).

In one embodiment, the memantine-containing compositions of the present invention comprise alkalizing agents to increase the local pH in the microenvironment of the memantine absorption site, thereby increasing the rate of uptake of memantine. A non-limiting list of suitable alkalizing agents includes magnesium oxide, sodium hydroxide, sodium carbonate, monoethanolamine, potassium hydroxide, diethanolamine, ammonium carbonate, tromethane, sodium phosphate tribasic, triethanolamine, sodium phosphate dibasic, sodium acetate, sodium citrate, ammonium solution, sodium bicarbonate, sodium phosphate monobasic calcium carbonate, potassium carbonate, potassium bicarbonate, potassium citrate, calcium phosphate, magnesium hydroxide, magnesium carbonate, magnesium trisilicate, aluminum carbonate and aluminum hydroxide and combinations thereof. In one particular embodiment of the invention, the alkalization agent is one or more of magnesium oxide, sodium hydroxide, sodium carbonate, potassium hydroxide, sodium phosphate tribasic, ammonium carbonate, or sodium phosphate dibasic.

Buffering agents can be used to effect pH change in the microenvironment of the absorption site in order to increase the concentration of non-ionized memantine. In some embodiments, basic buffering agents such as alkali carbonates rapidly elevate the pH of a microenvironment. It also possible to use a binary or ternary buffer system to maintain the pH above 8.5. For example, U.S. Pat. No. 7,658,945, which is incorporated herein by reference in its entirety for all purposes, discloses compositions for increasing the delivery of a hypnotic agent (zolpidem, which is less than 70% orally bioavailable) across the oral mucosa with a buffer system that produces a final pH independent of the initial pH, and sustains that final pH for a given period of time. The memantine compositions of the present invention contemplate the use of a buffer system as similar to that disclosed in U.S. Pat. No. 7,658,945 which produces and maintains a final pH above 8.5. Such buffered compositions have hitherto not been contemplated for memantine-containing compositions, since conventional formulations and indications requiring treatment with memantine have not required rapid absorption of memantine, which is known to be completely absorbed and have an absolute bioavailability of ~100%. In addition, the effects of alkalinizing agents or buffers differs depending on the specific characteristics of the drug, and moderate elevation of pH (e.g., to a pH of about 8.5) would not be expected to have as significant effect on the extent of ionization of memantine as it would for other drugs such as zolpidem In various embodiments, the compositions of the present invention include one or more buffering agents which provide at least about 25%, 30%, 35%, 40%, 45%, 50%, 55%, 60%, 65%, 70%, 75%, 80%, 85%, 90%, 95%, or 100% of the memantine in the form of a free-base (un-ionized) during administration.

2. Permeation Enhancers

Memantine is a Biopharmaceutics Classification System (BCS) class I drug (highly soluble/highly permeable). Memantine is highly soluble at all physiological pHs (>30 mg/mL), and its bioavailability is >100%. The mechanism of absorption of memantine is most likely a combination of passive paracellular and passive transcellular absorption.

Figure 11:
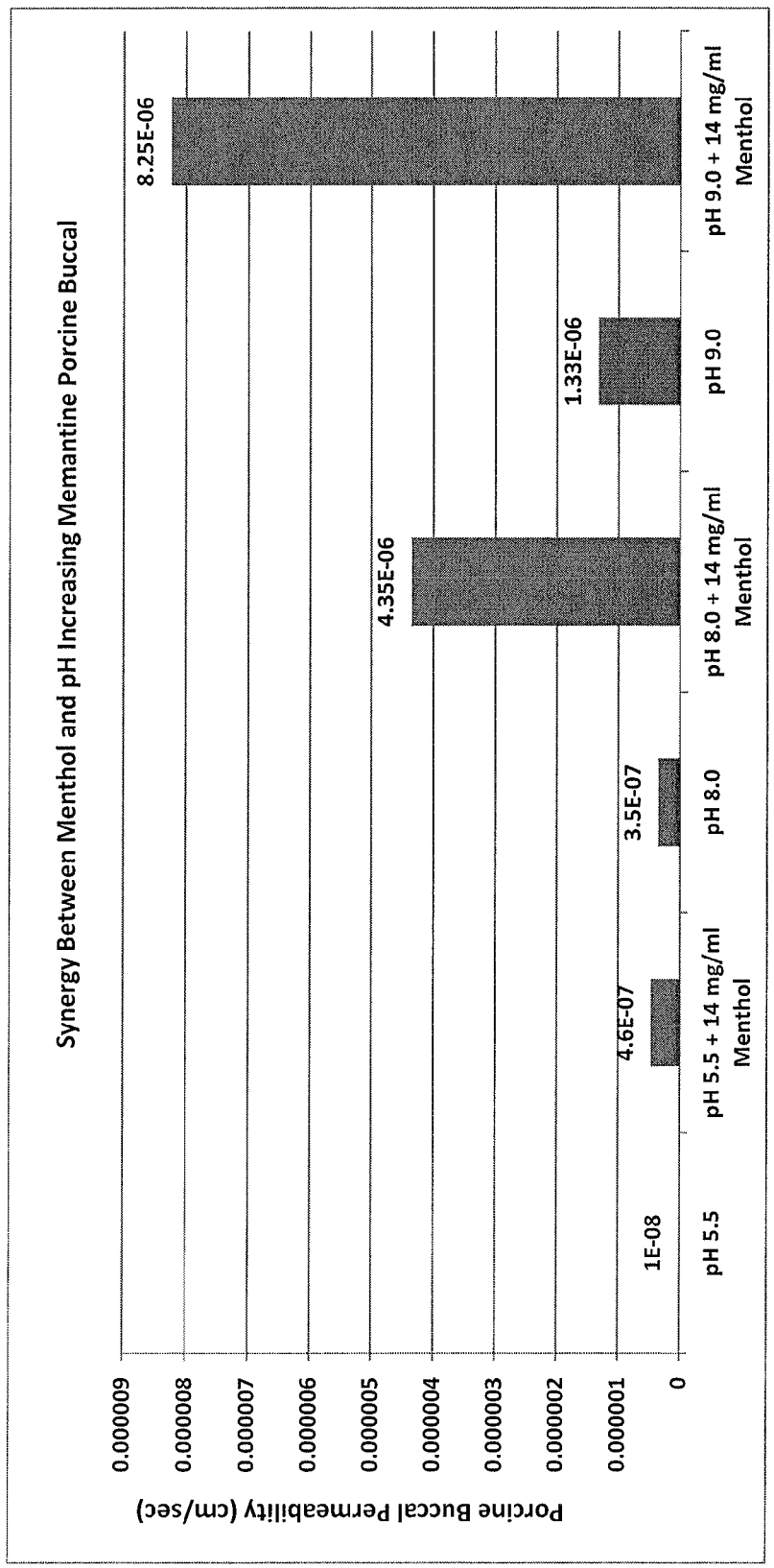
FIG. 11: Synergistic effect of increasing pH and concurrent use of a permeation enhancer on the rate of permeability of memantine in porcine buccal mucosa.

As disclosed herein, an increase in pH was found to increase the rate of permeability of memantine in porcine buccal mucosal tissue. Surprisingly and unexpectedly, it was found that the addition of particular permeation enhancers (e.g., menthol) in combination with an alkalizing agent or buffer resulted in a significant and synergistic increase in the rate of permeability of memantine (FIG. 11). FIG. 11 shows that an increase in pH from 8.0 to 9.0 resulted in about 3.8 fold increase in permeability. Surprisingly, addition of menthol (14 mg/mL) resulted in about a 6 fold increase at pH 8.0 and about a 12 fold increase at pH 9.0. Such an increased rate of permeability substantially increases the rate of absorption of memantine. Accordingly, one embodiment of the present invention is a memantine-containing composition comprising at least one alkalization agent and at least one permeation enhancer. In one particular aspect of the invention, the permeation enhancer is menthol.

Thus, in some embodiments of the invention, the inventive compositions include permeation enhancers which enhance permeation of memantine across epithelial layers. Such permeation enhancers can be included in combination with agents that increase local pH (e g alkalizing agents and/or buffers). In one specific embodiment, the present compositions may include menthol and another permeation enhancer. Suitable permeation enhancers for use in the compositions of the present invention also include chitosan which increases mucosal transcellular and/or paracellular permeability independent of pKa and logP, thereby facilitating immediate local absorption. Other suitable permeation enhancers include resorcinol, surfactants, polyethylene glycol or bioacids such as citric acid, lactic acid, etc. Alternatively, microencapsulation of memantine with liposomes, polysaccharides could also be used to limit enzymatic degradation as well as enhance permeability. Other permeation enhancers suitable for use in the invention include peptide transport agents such as those disclosed in U.S. Pat. No. 7,176,185 which is incorporated herein by reference in its entirety for all purposes. In addition, suitable permeation enhancers may include, but are not limited to, dimethylsulfoxide ("DMSO"), dimethyl formamide ("DMF"), N,N-dimethylacetamide ("DMA"), decylmethylsulfoxide ("CIOMSO"), polyethylene glycol monolaurate ("PEGMLIt), glycerol monolaurate, lecithin, 1-substituted azacycloheptan-2-ones such as 1-n-dodecylcyclazacycloheptan-2-one (available under the trademark Azone® from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and surfactants such as Tergitol®, Nonoxynol-9® and TWEEN-80®. In a particular embodiment, the permeation enhancer is menthol (typically the naturally occurring stereoisomer 1R,2S, 5R-menthol, although any other stereoisomer or combination of menthol stereoisomers can be used).

Figure 12:
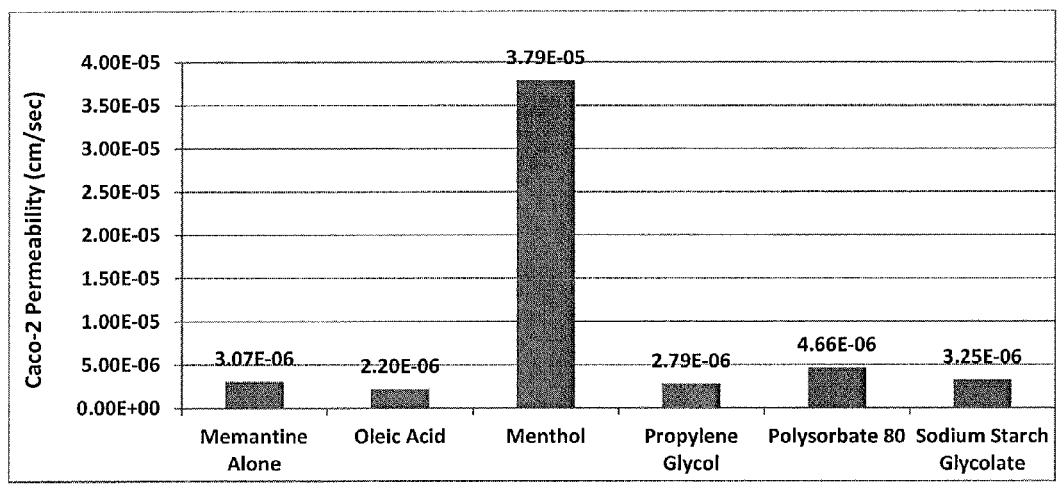
FIG. 12: Comparison of Memantine Caco-2 permeability in the presence of various potential permeation enhancers.

Various permeation (or penetration) enhancers have been proposed to increase the permeability of drugs through the oral mucosa, for example those disclosed in U.S. Pat. No. 7,682,628 for use with zolpidem compositions. However, the present inventors have found that various permeation enhancers which are effective for zolpidem or other drugs are not effective for memantine, and thus appear to have drug-specific activity for enhancing drug permeation. See, for example FIG. 12, which shows that oleic acid, propylene glycol, polysorbate 80, and sodium starch glycolate are ineffective as permeation enhancers, while menthol unexpectedly provides an approximately 10-fold increase in the permeability of memantine.

3. Urine Acidification

In other embodiments, the compositions of the present invention include excipients which increase the rate of elimination of memantine, for example excipients which provide urinary acidification can be included in the compositions of the present invention. These urine acidification agents can be used alone or in combination with agents that increase local pH (e.g. alkalizing agents or buffers), used in combination with permeation enhancing agents, or used in combination with both agents that increase local pH and permeation enhancing agents. Urine acidification leads to rapid terminal elimination of drugs, including memantine. Decrease in urine pH (urine acidification) increases the excretion of memantine. (Freudenthaler et al. *Br. J. Clin. Pharmacol.* 1998, 46(6): 541-546). However, urine acidification agents have not been conventionally used in combination with active agents in pharmaceutical formulations (e.g. because it is typically desirable to maintain therapeutic levels of the active agent as long as possible).

A non-limiting list of suitable urinary acidification agents includes calcium chloride, ammonium chloride, sodium biphosphate, sodium acid phosphate, ammonium phosphate, glutamic acid hydrochloride, methionine and other amino acids. If the urinary acidification agents do not have a desirable taste profile or are incompatible with those agents that facilitate rapid absorption (e.g., alkalizing agents or buffers) such urinary acidification agents can be encapsulated, for example encased within various resins. In one example the solubility of the resins may be pH independent. In one specific embodiment, the resin may be ethylcellulose. In another example, the resin may be enteric resins. These enteric resins may have pKa values that enable distal GI release. In this fashion, the formulations of the present invention containing urinary acidification agents are designed in such a way that the release of urinary acidification agents is delayed until they reach the distal small intestine. In one specific embodiment of the invention, alkalizing agents can be released in the proximal intestine to intentionally increase the pH as a means to maintain memantine in a non-ionized state thereby increasing absorption, and encapsulated urinary acidification agents are released in the distal GI tract (to avoid the release of urinary acidification agents in the proximal GI tract with the alkalizing agent).

Figure 13:
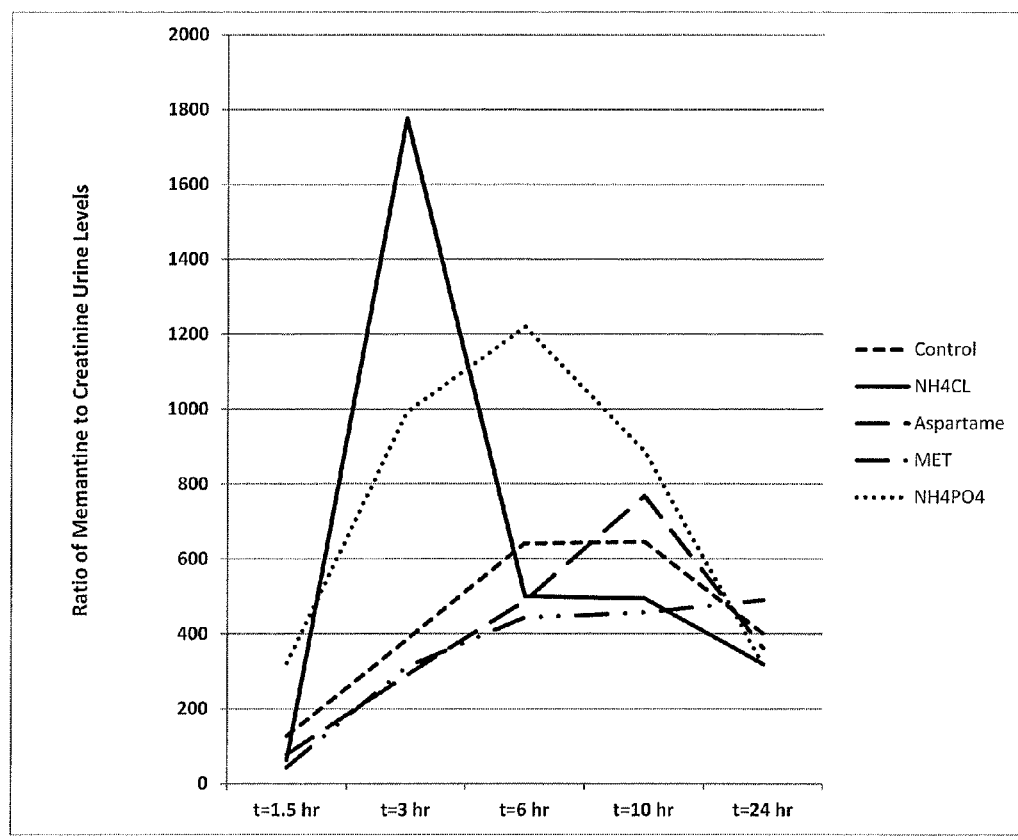
FIG. 13: Memantine excretion (relative to creatinine) for various urinary acidifying agents. Ammonium Chloride (25 mg/kg) & Ammonium Phosphate (50 mg/kg) accelerated memantine excretion rate while methionine and aspartame did not.

As shown in FIG. 13, urinary acidifying agents are effective in increasing the rate of excretion of memantine (expressed relative to creatinine). In particular embodiments, ammonium chloride ($NH_4Cl$), ammonium phosphate (($NH_4$)$_3PO_4$), and aspartame are urinary acidifying agents effective in increasing the rate of elimination of memantine. Other suitable urinary acidifying agents include ammonium ascorbate, ammonium glycrrhizate, glutamic acid hydrochloride, sodium biphosphate, dibasic sodium phosphate, dibasic potassium biphosphate, sodium acid phosphate, ascorbic acid, calcium chloride, etc.

Memantine Dose

Suitable doses of memantine may depend in part with the characteristics of the patient and the type of cough treated. In some embodiments, the patient is a human over about 12 years of age and the composition of the present invention may be administered in about one dose at least once a day, at least twice a day, once a day, or twice a day. In other embodiments, the patient is human from about 6 to about 12 years of age, and the composition of the invention is administered in about ½ dose (relative to patients over about 12 years of age) once a day or twice a day. In another embodiment, the patient is a human from about 2 to about 6 years of age, and the composition of the invention is administered in an about ¼ dose (relative to patients over about 12 years of age) once a day or twice a day.

The total dosage per day of the active compounds may be a factor in determining the criteria for administering the composition of the invention. For example, compositions with a higher concentration of active compounds may be taken in smaller dosages and/or less frequently, and compositions with lower concentrations of the active compounds may be taken in larger volume dosages and/or more frequently.

In various embodiments, the memantine dose ranges from about 1 mg/dose to about 35 mg/dose, including about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 mg/dose, about 31 mg/dose, about 32 mg/dose, about 33 mg/dose, about 34 mg/dose, or about 35 mg/dose, inclusive of all ranges and subranges therebetween.

In certain other embodiments, the memantine dose is about 0.01 mg/kg to about 0.5 mg/kg, including about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.12 mg/kg, about 0.14 mg/kg, about 0.16 mg/kg, about 0.18 mg/kg, about 0.2 mg/kg, about 0.22 mg/kg, about 0.24 mg/kg, about 0.26 mg/kg, about 0.28 mg/kg, about 0.30 mg/kg, about 0.32 mg/kg, about 0.34 mg/kg, about 0.36 mg/kg, about 0.38 mg/kg, about 0.4 mg/kg, about 0.42 mg/kg, about 0.44 mg/kg, about 0.46 mg/kg, about 0.48 mg/kg, or about 0.5 mg/kg, inclusive of all ranges and subranges therebetween. As discussed above, younger patients may require doses which are ½ or ¼ of the doses described above.

Combinations with Other Active Agents

In other embodiments of the present invention, memantine can be advantageously combined with other active agents in order to more effectively inhibit, treat, or ameliorate cough in a patient.

In addition to being a potent NMDA receptor antagonist, Motawaj et al. recently postulated that a central histaminergic effect may be responsible for the enhancement of cognition by memantine in Alzheimer's patients (Motawaj et al., *J Pharmacol Exp Ther.* 2010 Nov. 5). They observed increases in rodent brain t-MeHA levels after acute or repeated administration of therapeutic doses of memantine. In-vitro, memantine antagonized native NMDA receptors with a micromolar potency, but had no effect at recombinant human histamine receptors. In-vivo, acute administration of memantine increased histamine neuron activity, as shown by the 60% increase of tele-methylhistamine (t-MeHA) levels observed in the brain of mice. This increase occurred with an ED50 of 0.3±0.1 mg/kg, similar to that found on inhibition of ex vivo [3H]MK-801 binding (1.8±1.3 mg/kg). Two days after pre-treatment of mice with memantine at 5 mg/kg twice daily for 5 days, t-MeHA levels were enhanced by 50±7% (p<0.001), indicating a long-lasting activation of histamine neurons. Quantitative PCR analysis was used to explore genes involved in this persistent effect. H3-receptor mRNAs were strongly increased, but the density of H3-receptor binding sites was increased solely in hypothalamus (by 141±24%). Up-regulations of BDNF and NMDA-receptor 1 subunit mRNAs were also found, but were restricted to hippocampus. mRNA expression of alpha7-nicotinic receptors remained unchanged in any region.

First generation antihistamines such as diphenhydramine, chlorpheniramine, doxylamine and brompheniramine are very commonly used in combination antitussive preparations (*SDI Vector One* 2010). They are usually combined with codeine or dextromethorphan to provide decongestion, reduction of post-nasal drip (via the peripheral effects of anti-histamines) and additional cough suppression (via central effects). For patients that cannot tolerate the sedation, amphetamines and alpha adrenergic agonists that have decongestant effects such as pseudoephedrine and neosynephrine are frequently added to the combination preparation, or used in lieu of the antihistamine. However, given the preponderance of cardiovascular side effects of amphetamines and adrenergic agonists and their abuse liability, better alternatives are needed. Accordingly, memantine can be advantageously combined with such active agents in the compositions of the present invention to antagonize the sedating effects of centrally acting antihistaminic agents (e.g., mepyramine, antazoline, diphenhydramine, carbinoxamine, doxylamine, clemastine, dimenhydrinate, pheniramine, chlorpheniramine, dexchlorpheniramine, brompheniramine, triprolidine, dimetindene, cyclizine, chlorcyclizine, hydroxyzine, meclizine, promethazine, trimeprazine, cyproheptadine, azatadine and ketotifen), and thereby provide substantially more effective antitussive compositions. For example, the combination of therapeutically effective doses of memantine with therapeutically effective doses of first generation antihistamines will provide for antitussive effect without the sedating effects of the antihistamine.

Such combinations of memantine and other pharmaceutically active agents such as first generation antihistamines (e.g., diphenhydramine) or ambroxol, benzonatate or guaifenesin are synergistic in treating cough, as shown in FIGS. 15-18. Either memantine alone, or diphenhydramine alone provide are ineffective at reducing cough (relative to controls; see FIG. 16). However, in combination memantine and diphenhydramine are surprisingly synergistic in their effects, as the combination provides a substantial and unexpected increase in antitussive effect (decrease in cumulative number of coughs compared to controls (FIG. 16)).

The antitussive compositions of the present invention comprising memantine may also include an antihistamine in some of the embodiments. Such antihistamines may include first generation antihistamines as disclosed herein, mepyramine, antazoline, diphenhydramine, carbinoxamine, doxylamine, clemastine, dimenhydrinate, pheniramine, chlorpheniramine, dexchlorpheniramine, brompheniramine, triprolidine, dimetindene, cyclizine, chlorcyclizine, hydroxyzine, meclizine, promethazine, trimeprazine, cyproheptadine, azatadine and ketotifen. The composition may further comprise other pharmaceutically active ingredients such as other antitussives, decongestants, nasal decongestants, expectorants, analgesics, and opioid analgesics. In some of the embodiments, the antihistamines may be provided in the form of an immediate release component. Alternatively, in other embodiments, the antihistamine may be provided as a controlled release component.

In other embodiments, the antitussive compositions of the present invention include antipyretics (and/or antipyretic/analgesics) such as aspirin, acetaminophen, naproxen sodium, ketoprofen, aspirin, salicylates, choline salicylate, magnesium salicylate, sodium salicylate, metamizole, nabumetone, nimesulide, phenazone, quinine, etc.

In one embodiment, memantine may be used to prevent or inhibit or reduce unwanted side effects of an active agent. In a specific embodiment, the unwanted side effects may be those that impair cognition of a patient. In another specific embodiment, the impaired cognition may be due to sedation. In one embodiment, the antitussive compositions of the present invention comprising memantine may also include an active agent. In a specific embodiment, the added active agent may be an antihistamine, such as a first generation antihistamine. Specifically, memantine may prevent or inhibit sedation or similar side effects caused by an antihistamine which impair cognition of a patient. For example, FIG. 14 demonstrates that the administration of memantine before the administration of the antihistamine diphenhydramine prevents or inhibits the cognitive impairment caused by diphenhydramine. Accordingly, in a specific embodiment, the antitussive composition may comprise memantine and an antihistamine. In a specific embodiment, the composition may also include the antihistamine diphenhydramine.

In another embodiment, the composition may comprise memantine, which is administered before or after the administration of another active agent. In a specific embodiment, the active agent may be an antihistamine. In one embodiment, the administration of a composition comprising memantine may be within about one hour (before or after) the administration of an antihistamine. In another embodiment, the administration may be within about 2 hrs, about 3 hrs or about 4 hrs. The following examples are particular embodiments of the invention. It should be appreciated by those of skill in the art that these examples are suitable in the practice of the present invention, and thus can be considered to constitute particularly suitable embodiments for its practice. However, those of skill in the art should, in light of the present disclosure, appreciate that many changes can be made in these specific embodiments which would obtain a like or similar result without departing from the spirit and scope of the invention.

Memantine Compositions Comprising Guaifenesin and Phenylephrine

In some other embodiments, memantine compositions of the present invention additionally comprise guaifenesin and phenylephrine. Guaifenesin is an expectorant which increases the output of phlegm (sputum) and bronchial secretions by reducing adhesiveness and surface tension. The increased flow of less viscid secretions promotes ciliary action and changes a dry, unproductive cough to one that is more productive and less frequent. Phenylephrine is a sympathomimetic nasal decongestant which acts predominantly on alpha adrenergic receptors in the mucosa of the respiratory tract, producing vasoconstriction with minimal action on beta receptors. It functions as an oral nasal decongestant with minimal central nervous system (CNS) stimulation and promotes sinus drainage.

In certain embodiments, memantine compositions may comprise other pharmaceutically active agents. In certain embodiments, the other pharmaceutically active agents may comprise nasal decongestant(s) and expectorant(s). In certain specific embodiments the nasal decongestant is phenylephrine and the expectorant is guaifenesin.

Phenylephrine ((S)-3-hydroxy-α-[(methylamino)methyl] benzene-methanol) is a sympathomimetic amine. It acts as an oral nasal decongestant and laryngeal mucous membrane decongestant, with minimal central nervous stimulation, by stimulating alpha-adrenergic receptors to produce pronounced vasoconstriction in the skin, mucous membranes and the mucosa. In a specific embodiment, phenylephrine may be in the form of phenylephrine tannate. In a specific embodiments of the compositions and methods of the present invention, phenylephrine may be included in amounts ranging from about 5 mg/dose to about 15 mg/dose, including about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, inclusive of all ranges and subranges there between.

Viscous secretion exists in the airway of the human body. This secretion has an important role in imparting suitable temperature and humidity to inhaled air. When its amount is moderate, the secretion in the airway is unconsciously swallowed or expelled with the breath, but usually never is expectorated. Thus, any expectoration suggests that there is something extraordinary in the respiratory system. On the other hand, accumulation of this secretion in the airway is liable to cause an infection via the airway. From this point of view, the removal of the secretion is a matter of great significance in the medical treatment of patients who suffer with a disease in the airway.

In order to facilitate expectoration, medicines referred to as "expectorants" have been used. Most expectorants serve to remove the secretion by diluting it through an increase in secretion by the mucosa of the airway, promotion of separation from the mucosa and enhancement of ciliary beat. Guaifenesin (3-(2-methoxyphenoxy)-1,2-propanediol), also known as glyceryl guaiacolate, is an expectorant. It is readily absorbed from the intestinal tract and is thought to enter airway secretions unmetabolized and to have a direct effect either on the mucus secretion itself or the epithelium (Rubin, CHEST 1999, 116, 195-200). For example, guaifenesin is thought to reduce the thickness of mucus and phlegm secretions by increasing the production of fluids in the respiratory tract thus helping to liquefy and thin airway secretions. The increased flow of less viscid secretions promotes ciliary action and further facilitates the removal of airway secretions. Guaifenesin also may inhibit cough peripherally in the airway, by hydrating airway mucus so that it shields the cough receptors from cough-inducing irritants. (Dicpinigaitis et al., CHEST 2003, 124, 2178-2181). These peripheral actions of guaifenesin aid in the removal of accumulated secretions from the trachea, bronchi and lungs, thus changing a dry, non-productive cough to a cough that is more productive and less frequent. Guaifenesin also may act to suppress cough through an effect in the central nervous system (Rubin, supra.) The exact mechanism by which guaifenesin inhibits cough in some patients is unknown.

Figure 15:
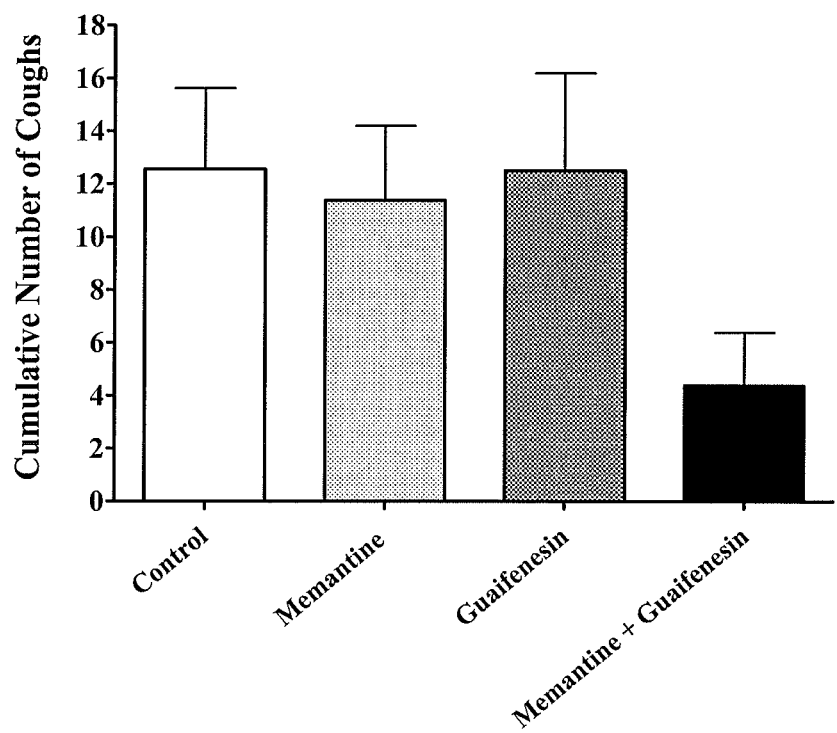
FIG. 15: Comparison of cough responses evoked by citric acid in control animals and animals treated with 3 mg/kg of memantine alone, 100 mg/kg of guaifenesin alone, and the synergistic effects of the combination of memantine and guaifenesin, both administered orally.
Figure 16:
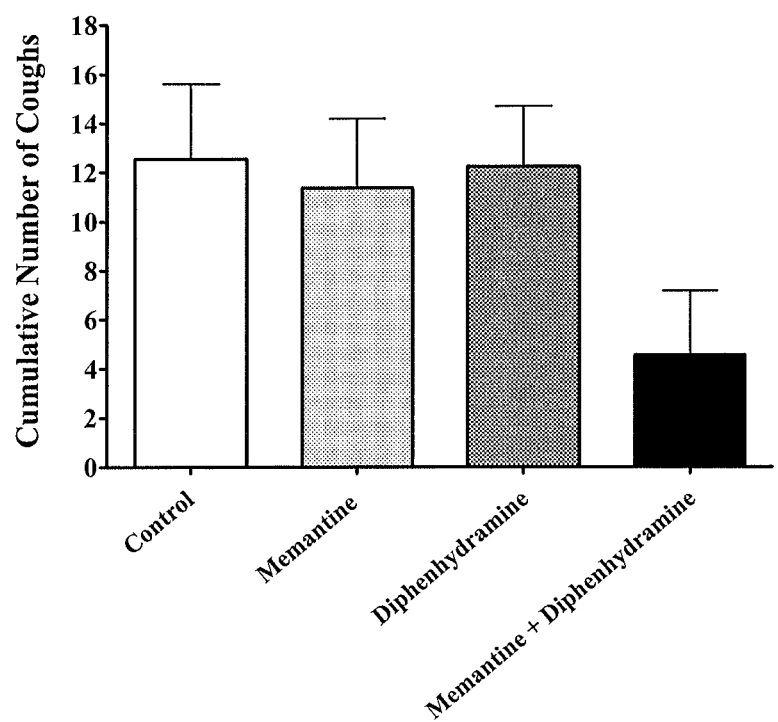
FIG. 16: Comparison of cough responses evoked by citric acid in control animals and animals treated with 3 mg/kg of memantine alone, 10 mg/kg of diphenhydramine alone, and the synergistic effect of the combination of memantine and diphenhydramine, both administered orally.
Figure 17:
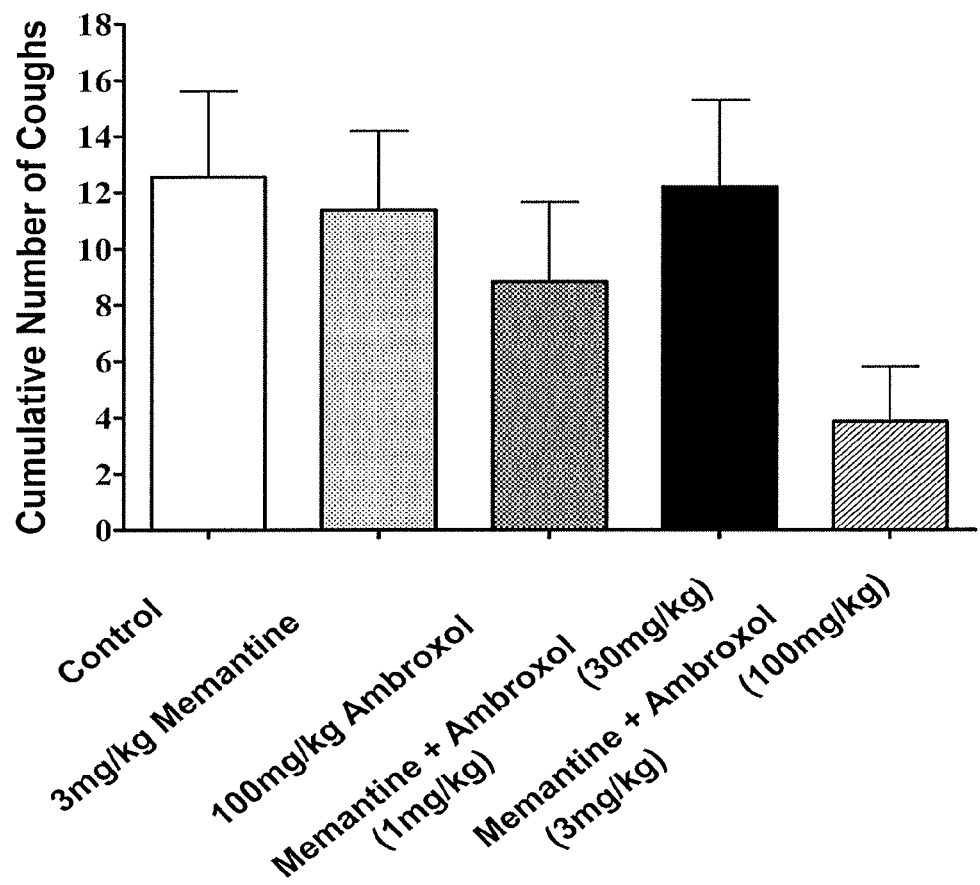
FIG. 17: Comparison of cough responses evoked by citric acid in control animals and animals treated with 3 mg/kg of memantine alone, 100 mg/kg of ambroxol alone, and the synergistic effect of the combination of memantine and ambroxol, both administered orally.
Figure 18:
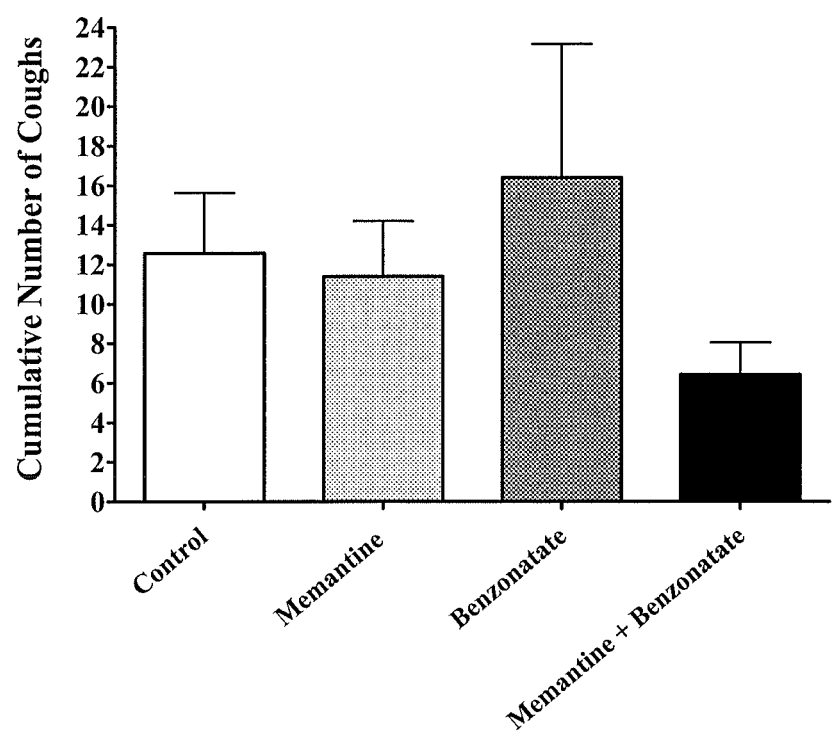
FIG. 18: Comparison of cough responses evoked by citric acid in control animals and animals treated with 3 mg/kg memantine alone, 30 mg/kg benzonatate alone, and the synergistic effect of the combination of memantine and benzonatate, both administered orally.

As is shown in FIG. 15, combinations of memantine and guaifenesin provide synergistic effects in treating cough compared to either memantine or guaifenesin alone.

In a specific embodiment of the compositions and methods of the present invention, guaifenesin may be present in amounts ranging from about 50 mg/dose to about 150 mg/dose, including about 50, about 55, about 60, about 65, about 70, about 75, about 80, about 85, about 90, about 95, about 100, about 105, about 110, about 115, about 120, about 125, about 130, about 135, about 140, about 145, or about 150 mg/dose, inclusive of all ranges and subranges therebetween.

In some embodiments of the present invention, the compositions may be substantially free of active ingredients other than guaifenesin, phenylephrine, and memantine. In some embodiments, the compositions may be substantially free of extended release forms of phenylephrine. In one embodiment, the compositions of the present invention may be substantially free of at least one other added antitussive. In another embodiment of the present invention, the compositions may be substantially free of at least one other added decongestant. In another embodiment of the present invention, the compositions may be substantially free of at least one other added nasal decongestant. In another embodiment of the present invention, the compositions may be substantially free of at least one other added opioid analgesic. In another embodiment of the present invention, the compositions may be substantially free of at least one other expectorant. In other embodiments of the present invention, the compositions may be substantially free of one or more other active ingredient, such as, but not limited to, antitussives, decongestants, nasal decongestants, opioid analgesics, and/or expectorants.

In other embodiments of the present invention, the compositions may additionally comprise one or more added active ingredients in addition to guaifenesin, phenylephrine, and memantine. For example, in one embodiment, the compositions of the present invention may comprise at least one other added antitussive. In another embodiment of the present invention, the compositions may comprise at least one other added decongestant. In another embodiment of the present invention, the compositions may comprise at least one other added nasal decongestant. In another embodiment of the present invention, the compositions may comprise at least one other opioid analgesic. In another embodiment of the present invention, the compositions may comprise at least one other expectorant. In other embodiments of the present invention, the compositions may comprise one or more other active ingredient, such as, but not limited to, antitussives, decongestants, nasal decongestants, opioid analgesics, and/or expectorants.

Additional antitussives suitable for use in the compositions of the present invention include, but are not limited to, dextromethorphan, dextromethorphan hydrobromide, codeine, codeine phosphate, codeine sulfate, hydrocodone, morphine, morphine sulfate, hydromorphone hydrochloride, levorphanol tartrate, fentanyl, fentanyl citrate, oxycodone hydrochloride, oxymorphone hydrochloride, methadone hydrochloride, apomorphine hydrochloride, beechwood creosote, benzonatate, camphor ethanedisulfonate, diphenhydramine, diphenhydramine hydrochloride, chlophendianol hydrochloride, carbetapentane citrate, caramiphen edisylate, noscapine, noscapine hydrochloride, and menthol.

Decongestants suitable for use in the compositions of the present invention include, but are not limited to, ephedrine, ephedrine sulfate, ephedrine hydrochloride, pseudoephedrine hydrochloride, phenylephrine hydrochloride, epinephrine bitartrate, hydroxyamphetamine hydrobromide, propylhexedrine, phenylpropanolamine hydrochloride, mephentermine sulfate, methoxamine hydrochloride, naphazoline hydrochloride, oxymetalozine hydrochloride, tetrahydrozoline hydrochloride, and xylometazoline hydrochloride.

Opioid analgesics suitable for use in the compositions of the present invention include, but are not limited to, such as, codeine, morphine, hydromorphone, hydrocodone, oxymorphone, levorphanol, fentanyl, propoxyphene, diphenoxylate, meperidine, methadone, oxycodone, butorphanol, and morphine.

Expectorants suitable for use in the compositions of the present invention include, but are not limited to ammonium chloride, ammonium carbonate, acetylcysteine, antimony potassium tartrate, glycerin, potassium iodide, sodium citrate, terpin hydrate, and tolu balsam.

Mucolytics include, for example, acetylcysteine, ambroxol, bromhexine, carbocisteine, domiodol, dornase alfa, eprazinone, erdosteine, letosteine, mesna, neltenexine, sobrerol, stepronin, tiopronin, etc.

In some embodiments of the present invention, the compositions may substitute one or more other active agents for guaifenesin and phenylephrine. For example, in one embodiment, the compositions of the present invention may substitute another expectorant for guaifenesin. In another embodiment of the present invention, the compositions may substitute another decongestant for phenylephrine.

Substitute decongestants suitable for use in the compositions of the present invention include, but are not limited to, ephedrine, ephedrine sulfate, ephedrine hydrochloride, pseudoephedrine hydrochloride, epinephrine bitartrate, hydroxyamphetamine hydrobromide, propylhexedrine, phenylpropanolamine hydrochloride, mephentermine sulfate, methoxamine hydrochloride, naphazoline hydrochloride, oxymetalozine hydrochloride, tetrahydrozoline hydrochloride, and xylometazoline hydrochloride, and functional variants and derivatives thereof.

Substitute expectorants suitable for use in the compositions of the present invention include, but are not limited to ammonium chloride, ammonium carbonate, acetylcysteine, antimony potassium tartrate, glycerin, potassium iodide, sodium citrate, terpin hydrate, and tolu balsam.

In one embodiment, the compositions of the present invention (e.g., comprising memantine, phenylephrine and guaifenesin) can include a caloric sweetener (e.g., a sugar) or can be sugar free. In another embodiment, the compositions of the present invention (e.g., comprising memantine, phenylephrine and guaifenesin) can include (ethyl) alcohol or can be alcohol free. In another embodiment, the compositions of the present invention (e.g., comprising memantine, phenylephrine and guaifenesin) can be both sugar and alcohol free. In some instances, sugar-free versions of products may be manufactured using sugar replacements, such as, for example and without limitation, isomalt, saccharin sodium, maltodextrin, aspartame, potassium acesulfame, neohesperidin dihydrochalcone, cyclamate, stevia, sucralose, monoammonium glycyrrhizinate, and mixtures thereof. These "sugar replacements" have the advantage that they do not decompose to form products that attack the dental enamel as a result of the bacterial flora present in the mouth during metabolism, even if the teeth are not cleaned properly. The "sugar replacements" also are suitable for consumption by diabetics and do not add unneeded or unwanted calories to products such as medications. Thus, in a specific embodiment of the compositions and methods of the present invention, the compositions may be free of any added sugar, and instead, may contain a sugar substitute, such as for example and without limitation, one or more of the sugar replacements described above.

Oral Formulations

The present invention provides an antitussive composition comprising memantine or pharmaceutically acceptable salts thereof. The antitussive composition provided herein is in most embodiments an oral dosage form. Such an oral dosage form can be in the form of a liquid (e.g., solutions or suspensions such as a syrup or elixir) intended for oral administration. In addition to the oral administration, liquid dosage forms can also be administered as buccally or sublingually absorbed sprays (e.g., using a metered pump of aerosol device). In such embodiments, the liquid formulation comprises discrete droplets comprising memantine, or memantine in combination with other agents as described herein.

In certain embodiments of the present invention, the composition containing memantine, phenylephrine and guaifenesin can be administered as a liquid form. Such a liquid form can be, but is not limited to an elixir in a sweetened aromatic solution of alcohol and water. In the present invention, however, syrups and other liquid vehicles may also be used. The preparation may or may not be a suspension. As used herein, the term "syrup" refers to a concentrated, aqueous preparation of a sugar or sugar substitute with or without an added flavoring agent. As used herein, the term "elixir" refers to a clear, sweetened, hydroalcoholic solution intended for oral use, and may or may not have an added flavoring agent. As used herein, a "suspension" is a preparation containing finely divided drug particles distributed somewhat uniformly throughout a vehicle in which the drug exhibits a minimum degree of solubility. Although water itself may make up the entire carrier, typical cough formulations may contain a co-solvent, for example and without limitation, propylene glycol and/or glycerin, to assist solubilization and incorporation of water insoluble ingredients, flavorants and the like into the composition. Any such ingredients may be included as desired or needed within the compositions and methods of the present invention as long as they are consistent with the objectives herein defined. For example, it is contemplated that when desirable, flavoring, preserving, suspending, thickening and/or emulsifying agents may be included in the compositions and methods of the present invention. Formulations for orally administered medications are well known in the art. Descriptions of suitable formulations may be found in (Remington, *The Science and Practice of Pharmacy* A. Gennaro ed., 20.sup.th ed., Lippincott, Williams & Wilkins, 2000).

Compositions containing memantine, phenylephrine and guaifenesin may also include flavorants that are known to those skilled in the art. These flavorants may include, for example and without limitation, natural, artificial and synthetic flavor oils and flavoring aromatic and/or oils, oleoresins and extracts derived from plants, animals, leaves, flowers, fruits, and so forth, and combinations thereof. Non-limiting representative flavor oils include anise oil, cinnamon oil, peppermint oil, spearmint oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, and grape oil. Also useful flavorants include fruit essences including apple essence, pear essence, peach essence, berry essence, wildberry essence, date essence, blueberry essence, kiwi essence, strawberry essence, raspberry essence, cherry essence, black cherry essence, plum essence, pineapple essence, and apricot essence. Other useful flavorants include aldehydes and esters such as benzaldehyde (cherry, almond), citral, i.e., α-citral (lemon, lime), neral, i.e., β-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), mixtures thereof and the like. Honey and artificial honey flavor, as well as natural mixed berry flavor, citric acid, malic acid, vanilla, vanillin, cocoa, chocolate, and menthol may also be used in accordance with the present invention. Flavorants appealing to non-human patients may also be included in the composition of the invention, including but not limited to, yeast extract, meat extract, fish extract, poultry extract, cheese and other dairy flavors, and the like.

Another aspect of the invention are methods of administering to a patient the composition of the invention, comprising memantine and extended release forms of guaifenesin and phenylephrine. In some embodiments, the composition comprises memantine and the tannate salts of phenylephrine and guaifenesin. In some embodiments, the composition is administered to the patient orally. The compositions of the invention may be administered in varying volumes and at varying frequencies. In specific embodiments, the dose unit is from about 1 to about 10 mL, or from about 0.1 to 100 mL. Specific dose units include, but are not limited to, 1.25 mL, 2.5 mL, 5.0 mL, and 10 mL. The frequency of the dose may vary from every other day to several times a day. In specific embodiments, the frequency of the dose may be once a day or twice a day.

Memantine (optionally in combination with other active agents as described herein) can also be formulated as a solid oral dosage form, for example as a tablet (including bi- and multi-layered tablets, orally disintegrating tablets, rapid dissolve tablets, chewable tablets) capsules, orally dissolving films, sachets, transdermal patches, etc.

Orally Disintegrating Dosage Forms

Orally disintegrating or dissolving dosage forms include orally disintegrating tablets (ODTs), fast dissolve tablets, orally dissolving films, lozenges, etc., which allow oral administration of the dosage form without the need to swallow the dosage form whole (i.e., as for conventional tablets). A fast orally disintegrating tablet, orally dispersible tablet, or lozenge is a drug dosage form available for a limited number of over-the-counter (OTC) and prescription medications. Such dosage forms differ from traditional tablets in that they are designed to disintegrate or dissolve on the tongue rather than be swallowed whole. The ODT or lozenge serves as an alternative dosage form for where compliance is a known issue and therefore an easier dosage form to take ensures that medication is taken. During the last decade, ODTs and lozenges have become available in a variety of therapeutic markets, both OTC and by prescription. An additional reason to use an ODT or lozenge is the convenience of a dosage form that can be taken without water.

The use of an orally disintegrating tablet (ODT) to administer pharmaceutical agents has been disclosed. See, e.g., U.S. Pat. Nos. 3,784,390, 5,411,945, 5,980,882 and 6,001,392, the disclosures of which are hereby incorporated by reference in their entirety for all purposes. Typically, such ODTs contain a water soluble polymer and other conventional excipients such as plasticizers and emulsifiers. However, the ODT composition will depend on the particular pharmaceutical agent and the desired formulation properties. For example, the formulation must be compatible with the pharmaceutical agent, and also must provide the necessary mechanical strength, taste-masking and dissolution properties. In further embodiments, the ODT should meet the FDA guidelines for disintegration (See e.g., Food and Drug Administration, Center for Drug Evaluation and Research, Guidance for Industry Orally Disintegrating Tablets April 2007) and provide a desired bioavailability. For example, the ODTs of the present invention disintegrate within about 10 seconds to 120 seconds, for example within about 10 seconds, 20 seconds, 30 seconds, 40 seconds, 50 seconds, 60 seconds, 70 seconds, 80 seconds, 90 seconds, 100 seconds, 110 seconds, or 120 seconds (inclusive of all ranges and subranges therebetween) and are bioequivalent to immediate release conventional tablet and liquid formulations of memantine.

In some embodiments, the ODT of the present invention includes a water-soluble polymer, a combination of two or more water-soluble polymers or a combination of a water-soluble polymer and a water-insoluble or poorly-soluble polymer. Water soluble polymers that may be used in the orally dissolving formulations of the present invention include, but are not limited to, cellulose derivatives, synthetic polymers polyacrylates and natural gums. For example, the water soluble polymers used in the orally dissolving formulations of the present invention may include, but are not limited to, methyl cellulose, hydroxypropyl cellulose, hydroxypropylmethyl cellulose, ethyl cellulose, hydroxyethyl cellulose, hydroxypropyl cellulose, carboxymethyl cellulose, cellulose acetate phthalate, cellulose acetate butyrate, amylose, dextran, casein, pullulan, gelatin, pectin, agar, carrageenan, xanthan gum, tragacanth, guar gum, acacia gum, arabic gum, polyethylene glycol, polyethylene oxide, polyvinyl pyrrolidone, polyvinyl alcohol, cyclodextrin, carboxyvinyl polymers, sodium alginate, polyacrylic acid, methylmethacrylate or mixtures thereof. In particular embodiments, the concentration of the water-soluble polymer in the formulation may be about 20% to about 90% (by weight), or between about 40% to about 80% (by weight). The above polymers can be used to coat the ODT. The coating can function as a taste-masking barrier (i.e., over particles of the drug contained within the ODT), and also can protect components from atmospheric degradation and improve appearance. In the instance where this coating may retard the disintegration, rapid disintegration agents can also be included in the composition. The use of disintegrating agents such as dried starch, sodium alginate, lactose, sodium bicarbonate, calcium carbonate, polyvinyl pyrrolidone, microcrystalline cellulose and the like in the tablet core or granulation mixture of a swallowable tablet formulation is known. For example, U.S. Pat. No. 4,965,072 discloses the use of a mixture of magnesium sulphate heptahydrate and sodium hexametaphosphate to prepare a granulating composition with an active ingredient, which, when formulated into a swallowable tablet, exhibits rapid disintegration or dispersion. U.S. Pat. No. 6,413,549 to R. P. Sheerer Corporation discloses a rapidly disintegrating, freeze-dried dosage form comprising coarse particles of active coated with a polymer or lipid material. U.S. Pat. No. 7,125,562 to SmithKline Beecham Corporation discloses disintegrating methylcellulose tablets. This patent discloses that the tablets have a first phase and a second phase blended with the first phase and that each phase may contain a disintegrant and a polymer. European Patent No. 878189 B1 to Hercules Incorporated discloses the use of hydrophobically modified polysaccharides, including hydroxypropylcellulose, in personal care products. All of these technologies can be used in combination with polymeric coatings to enhance the disintegration. In addition, any of the disintegration agents known in the skill of art can be used to improve the disintegration of ODTs when they are coated with polymers.

Memantine hydrochloride is a white, odorless substance that exists as needle-shaped crystals with a characteristic bitter taste. When provided as orally disintegrating formulations, e.g., tablets (ODTs), lozenges, and orally dissolving films (ODFs), the composition may be formulated so that the taste of memantine is masked.

In some embodiments, the orally disintegrating formulations of the present invention may comprise a sweetening or flavoring agent to mask the taste of memantine. Generally, any natural or synthetic flavoring agent or sweetening agent known in the art may be used in the orally disintegrating or dissolving formulations of the present invention. For example, sweetening or flavoring agents include, but are not limited to, essential oils, water soluble extracts, sugar, monosaccharides, oligosaccharides, aldose, ketose, dextrose, maltose, lactose, glucose, fructose, sucrose, mannitol xylitol, D-sorbitol, erythritol, pentitol, hexitol, malitol, acesulfame potassium, talin, glycyrrhizin, sucralose, aspartame, saccharin, sodium saccharin, sodium cyclamate, eugenyl formate aldehyde flavorings and combinations thereof.

Particular aldehyde flavorings that may be used in the compositions of the present invention include, but are not limited to acetaldehyde (apple); benzaldehyde (cherry, almond); cinnamic aldehyde (cinnamon); citral, i.e., a-citral (lemon, lime); neral, i.e., β-citral (lemon, lime); decanal (orange, lemon); ethyl vanillin (vanilla, cream); heliotropine, i.e., piperonal (vanilla, cream); vanillin (vanilla, cream); α-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12

(citrus fruits); 2-ethyl butyraldehyde (berry fruits); hexenal, i.e., trans-2 (berry fruits); tolyl aldehyde (cherry, black cherry, almond); veratraldehyde (vanilla); 2,6-dimethyl-5-heptenal, i.e., melonal (melon); 2-6-dimethyloctanal (green fruit); and 2-dodecenal (citrus, mandarin). In some embodiments, the taste-masking agents may include combination of acesulfame potassium and flavors. In other embodiments, the flavoring can be an ester such as ethyl or methyl anthanilate (grape).

One skilled in the art with the benefit of the present disclosure will appreciate that other and further ingredients may be included in the orally dissolving formulations of the present invention. For example, a matrix-forming polymer permeation enhancer, substance for imparting mucoadhesive properties, or other auxiliary substances disclosed, for example, in U.S. Patent Publication No. 2005/0163830, the disclosure of which is hereby incorporated by reference in its entirety.

In some embodiments, the orally dissolving formulations of the present invention may comprise particles of memantine (e.g., crystals of memantine, granulates comprising memantine, memantine layered beads, etc.) that have been coated with a taste-masking coating. The taste-masking coating masks the taste of the memantine by preventing dissolution of memantine in the mouth. Any coating suitable for use in pharmaceutical formulations may be used. See, e.g., R. C. Rowe in Materials used in Pharmaceutical Formulation, Blackwell Scientific Publications, Oxford, 1, 36 (1984), the disclosure of which is incorporated by reference herein in its entirety. Examples of suitable coating materials include polyethylene glycol, ethyl cellulose, methyl cellulose, hydroxypropyl methyl cellulose, acrylic resins, silicone elastomers, wax, fatty acids, polymethacrylate copolymers, shellac, etc. In some embodiments, the coating may include between about 1% to about 75% of the formulation, for example between about 10% to about 50% of the formulation. In some cases the taste-masking coating can include a water insoluble polymer such as ethyl cellulose or insoluble acrylic ester copolymers such as Eudragit NE30D, optionally combined with pore formers such as water soluble polymers such as PVP, hydroxypropyl methyl cellulose, water soluble particulates such as saccharides or sugar alcohols, NaCl, etc., gastrosoluble polymers such as amine-functional acrylates (e.g., Eudragit E100, EPO), or gastrosoluble particulates such as calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium oxide, magnesium phosphate and mixtures thereof.

In some embodiments, the orally dissolving formulations according to the present invention may include surfactants including, but not limited to, sodium docusate, polyoxyethylene ether, poloxamer, polysorbates (Tween), polyoxyethylene stearates, sodium lauryl sulfate, sorbitan esters and combinations thereof. If present, the surfactant may be included in the formulation from about 0.1% to about 10%, for example between about 1% to about 5% (by weight). In some embodiments, the surfactants may be included in the coating. In some other embodiments, the surfactants can be used as a compressibility augmenting agent. One skilled in the art, with the benefit of this disclosure, will understand that other components may be included to enhance one or more properties of the formulation. For example, the orally dissolving formulations according to the present invention may include disintegrating agents, antifoaming agents, antioxidants, buffering agents or coloring agents.

The present invention provides a formulation that when administered orally will disintegrate to release (coated and/or uncoated) particles of memantine, which are then swallowed. After swallowing, the rate of release of memantine is determined by a number of different factors, including the size of the memantine particles, the thickness and porosity of the taste-masking coating (if present), the presence of absorption enhancing agents (e.g., pH adjusting agents). In some embodiments, a water soluble inert filler may be used in the formulation to increase the solubility of the memantine.

In certain embodiments, the orally disintegrating formulations of the present invention disintegrate in the oral cavity within about 60 seconds, or within about 30 seconds, or within about 15 seconds.

In some embodiments, the orally dissolving formulations of the present invention may comprise a coating that comprises a plasticizer. In some embodiments, the coating helps in controlled release of active ingredients. Suitable plasticizers include, but are not limited to, polyethylene glycol, propylene glycol, glycerin, glycerol, monoacetin, diacetin, triacetin, dimethyl phthalate, diethyl phthalate, dibutyl phthalate, dibutyl sebacate, triethyl titrate, tributyl citrate, triethyl citrate, triethyl acetyl citrate, castor oil, acetylated monoglycerides, sorbitol or combinations thereof. In particular embodiments, the concentration of the plasticizer in the formulation may be about 0 to about 30 wt %, for example about 0 to about 10 wt % and in other embodiments about 0 to about 4 wt %.

In some embodiments, the orally dissolving formulations of the present invention may comprise an emulsifying agent as an excipient. As used herein, emulsifying agents include both solubilizers and wetting agents. Suitable emulsifying agents include, but are not limited to, polyvinyl alcohol, sorbitan esters, cyclodextrins, benzyl benzoate, glyceryl monostearate, polyoxyethylene alkyl ethers, polyoxyethylene stearates, poloxamer, polyoxyethylene castor oil derivatives (Cremophor), hydrogenated-vegetable oils, bile salts, polysorbates; ethanol or combinations thereof. The emulsifying agent can improve the compressibility during wet granulation process during manufacture.

In some alternative embodiments, the compositions of the present invention can be in the form of a freeze-dried or lyophilized dosage form. Freeze-dried or lyophilized dosage forms are generally known to dissolve rapidly or disintegrate when they come in contact with water or any aqueous fluids. These dosage forms include an open matrix network of water-soluble or water dispersible carrier material, which is impregnated with a unit dose of the pharmaceutical active agent, in this case memantine or a pharmaceutically acceptable salt thereof. These dosage forms are prepared by first adding the pharmaceutical active (memantine alone, or memantine combined with one or more additional active agents as described herein) to a solution comprising the carrier material and a suitable solvent, typically water. The resulting composition is then subjected to a freeze-drying procedure whereby the solvent sublimes under high vacuum.

Conventional Tablet Formulations

Alternatively, the oral dosage form of the present invention comprising memantine or a pharmaceutically acceptable salt thereof can be formulated as a tablet, pill, lozenge or a multiparticulate oral preparation.

In various embodiments of the present invention, the oral dosage forms of the present invention additionally comprise one or more pharmaceutically acceptable excipients, such as fillers, binders, disintegrants, lubricants, glidants, etc. known in the art.

Suitable fillers include, but are not limited to include lactose (e.g. spray-dried lactose, α-lactose, β-lactose, Tabletose®, various grades of Pharmatose®, Microtose® or Fast-Flo®), microcrystalline cellulose (various grades of Avicel®, Ceolus®, Elcema®, Vivacel®, Ming Tai® or Solka-Floc®), hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc. Certain embodiments may comprise a water insoluble filler, water soluble filler, and combinations thereof. The filler may be a water insoluble filler, such as silicon dioxide, titanium dioxide, talc, alumina, starch, kaolin, polacrilin potassium, powdered cellulose, microcrystalline cellulose, and combinations comprising one or more of the foregoing fillers. Particular water-soluble fillers include water soluble sugars and sugar alcohols, in certain embodiments, lactose, glucose, fructose, sucrose, mannose, dextrose, galactose, the corresponding sugar alcohols and other sugar alcohols, such as mannitol, sorbitol, xylitol, and combinations comprising one or more of the foregoing fillers.

Suitable binders include, but are not limited to starch, gelatin, and sugars such as sucrose, glucose, dextrose, molasses, and lactose. Natural and synthetic gums that have been used include acacia, sodium alginate, extract of Irish moss, panwar gum, ghatti gum, mucilage of isapol husks, carbomethoxycellulose, methylcellulose, polyvinylpyrrolidone, Veegum, and larch arabogalactan. Other agents that may be considered binders under certain circumstances are polyethylene glycol, ethylcellulose, waxes, water and alcohol. Suitable polymeric binders include for example, polymers selected from the group consisting of hydroxypropylcellulose, povidone, methylcellulose, hydroxypropyl methylcellulose, carboxyalkylcelluloses, polyethylene oxides, polysaccharides, acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch, etc.

Non-limiting examples of suitable disintegrants include dibasic calcium phosphate, dibasic calcium phosphate dihydrate, tribasic calcium phosphate, alginic acid, hydroxypropylcellulose, carboxymethylcellulose calcium, carboxymethylcellulose sodium, cross-linked carboxymethylcellulose sodium, swellable ion exchange resins, alginates, formaldehyde-casein, cellulose, croscarmellose sodium, crospovidone (e.g., cross-linked polyvinyl pyrrolidone), microcrystalline cellulose, sodium carboxymethyl starch, sodium starch glycolate, starches (corn starch, rice starch), and mixtures thereof.

Non-limiting examples of suitable lubricants include calcium stearate, magnesium stearate, sodium stearyl fumarate, stearic acid, zinc stearate, talc, waxes, Sterotex®, Stearowet®, and mixtures thereof. Non-limiting examples of suitable glidants include colloidal silicon dioxide, talc, and mixtures thereof. Non-limiting examples of suitable diluents include mannitol, sucrose, anhydrous dibasic calcium phosphate, anhydrous dibasic calcium phosphate dihydrate, tribasic calcium phosphate, cellulose, lactose, magnesium carbonate, microcrystalline cellulose, and mixtures thereof. Non-limiting examples of suitable glidants include colloidal silicon dioxide, talc, and mixtures thereof.

Suitable excipients include, but are not limited to, microcrystalline cellulose, colloidal silicon dioxide, talc, starch, sorbitol, cyclodextrin or combinations thereof. In some embodiments, the excipient may include talc as anti-adhering agent. In some embodiments, the anti-adhering agent is included in the coating. In some other embodiments, such an agent is mixed with other excipients and dispersed within the tablet composition.

In other embodiments, one or more excipients is selected to limit or avoid the formation of memantine adducts. As used herein, "adduct formation" refers to the formation of a compound with a particular formulation of a composition by a solid phase reaction. The general term "adduct" for a compound, also called an addition compound, results from the direct combination of two or more different compounds. For example, in the present invention, adduct formation may occur with formulations containing, for example, lactose (or other reducing sugars). Such adduct formation detracts from the efficacy of the product and increases the risks of other side effects. For example, the memantine adducts can have other physiological effects (e.g., lactose-memantine adduct has an antibiotic activity).

The tablets of the present invention can prepared by various methods known in the art, such as dry or wet granulation of the memantine with one or more excipients as described herein, by combining particles comprising memantine, such as granulates, memantine layered beads, etc., with extra-particular excipients as described herein. The microgranules or beads of memantine can be microencapsulated or coated using methods well-known in the art. In certain embodiments, some of the microgranules may comprise the pharmaceutically active agents while the other microgranules may aid in dispersing the active agents to increase the rate of absorption at the site of the absorption. In some embodiments, the solid oral dosage form can comprise a matrix which facilitates the dispersion of pharmaceutically active agents embedded therein.

Rapid/Fast Release Formulations of Memantine

The dosage form of present invention may provide a rapid release or immediate release of memantine. This means that the dosage form releases at least about 60% wt of memantine initially present in the dosage form within 30 minutes of administering the dosage form to a patient in need thereof. In particular embodiments, the dosage form releases at least about 75% wt of memantine at 30 minutes after administration to a patient in need thereof; or at least about 85% wt of the memantine at 30 minutes after administration to a patient in need thereof.

In addition to the methods described herein, immediate or rapid release of memantine may be accomplished by any means known in the pharmaceutical arts. Particular methods include immediate release coatings, immediate release layers, immediate release multiparticulates or granules, and immediate release tablets, capsules, or pills. Virtually any means for providing immediate or rapid release of pharmaceutical ingredients known in the pharmaceutical arts can be used with the dosage form of the present invention.

In some aspects of the present invention, the immediate or rapid release memantine can be presented in the form of an immediate release coating over a core. This core could be either inert or may contain other pharmaceutically active agents. "Inert" in this instance means that the core is substantially free of other pharmaceutically active agents but may contain pharmaceutically acceptable excipients. The excipients may include, but not limited to binders, dispersants, disintegrants, taste-masking agents, flavorants, sweeteners and the like. The core may further comprise agents that facilitate the immediate release of memantine.

When incorporated into an immediate release coating, memantine can be combined with a water soluble or water-dispersible polymer. Water soluble polymers that may be used in the orally dissolving formulations of the present invention include, but are not limited to, cellulose derivatives, synthetic polymers polyacrylates and natural gums. For example, the water soluble polymers used in the orally dissolving formulations of the present invention may include, but are not limited to, methyl cellulose, hydroxypropyl cellulose, hydroxypropylmethyl cellulose, hydroxyethyl cellulose, hydroxypropyl cellulose, carboxymethyl cellulose, amylose, dextran, casein, pullulan, gelatin, pectin, agar, carrageenan, xanthan gum, tragacanth, guar gum, acacia gum, arabic gum, polyethylene glycol, polyethylene oxide, polyvinyl pyrrolidone, polyvinyl alcohol, cyclodextrin, carboxyvinyl polymers, sodium alginate, polyacrylic acid, methylmethacrylate or mixtures thereof. In particular embodiments, the concentration of the water-soluble polymer in the formulation may be about 20% to about 90% (by weight), for example between about 40% to about 80% (by weight), or about 20%, about 25%, about 30%, about 35%, about 40%, up 45%, 50%, about 55%, 60%, about 65%, about 70%, about 75%, 90%, 95%, or about 95%, including all ranges and subranges therebetween.

Multilayered Tablets

In one embodiment of the invention, the invention relates to multi-layer tablets, such as bi-layer tablets. In one embodiment, the multilayer tablet is a bi-layer. In one embodiment, the bi-layer tablet comprises: (a) an immediate-release layer, e.g., containing memantine; and (b) a controlled-release layer, e.g., containing one or more additional active agents as disclosed herein.

In one embodiment, a bilayer tablet of the invention has a hardness of about 7, 7.5, 8, 8.5, 9, 9.5, 10, 10.5, 11, 11.5, 12, 12.5, 13, 13.5, 14, 14.5 or 15 kilaponds (kp). In one embodiment, the bilayer tablet has a hardness of about 9.5 kp. In a further embodiment, a bilayer tablet of the invention has a thickness of about 5, 5.5, 6, 6.5, 7, 7.5, 8, 8.5, 9, 9.5 or 10 mm. It will be understood that as to the kilapond and thickness measurements, increments of 0.1 decimal points are within the scope of the invention.

In certain aspects of the invention, the multi layer or bilayer tablet comprises an immediate release layer incorporating memantine alone or with other pharmaceutically active agents. In one embodiment, the immediate release layer is capable of releasing about 70 to about 80% of the one or more pharmaceutically active agent contained therein in the stomach of a subject in about 5 to about 10 minutes following oral administration. In one embodiment, the immediate release layer is capable of releasing about 90 to about 100% of one or more pharmaceutically active agent contained therein in the stomach of a subject in about 40 minutes.

In some embodiments, the immediate release layer comprises one or more excipients, including but not limited to silicified microcrystalline cellulose (e.g., HD90), croscarmellose sodium (AC-Di-Sol), and magnesium stearate. In one embodiment, the total layer weight of the immediate release layer is from about 100 to about 300 mg, such as about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg.

In one embodiment, the immediate layer comprising memantine and one or more pharmaceutically active agents a composition comprising an effective amount of each of hydrocodone bitartrate, acetaminophen and promethazine HCl is capable of dissolving in the stomach of a subject so that an effective plasma concentration of each of pharmaceutically active ingredient is present in a subject in from about 5 minutes to about 30 minutes.

In one embodiment, the immediate release layer comprises about 12.5 mg memantine HCl, about 121.5 mg silicified microcrystalline cellulose, about 15 mg croscarmellose sodium, and about 1 mg magnesium stearate.

A variety of known methods and materials may be used to bring about the immediate release. For instance, placement of the agent along an exterior of a tablet (e.g., coating the exterior or formulating the outer layer with the agent) and/or combined with forming a tablet by compressing the powder using low compaction can produce immediate release of the agent from the composition.

In a specific embodiment, an effective amount of the memantine or a salt thereof in immediate release form may be coated onto a substrate. For example, where the extended release of one or more other active pharmaceutical agents from a formulation is via a controlled release coating, an immediate release layer comprising memantine or a salt thereof can overcoat the controlled release coating. In another example, an immediate release layer can be coated onto the surface of a substrate wherein another pharmaceutically active agent is incorporated in a controlled release matrix. Where a plurality of controlled release substrates (e.g., multiparticulate systems including pellets, spheres, beads and the like) are incorporated into a hard gelatin capsule, a side-effect reducing compound can be incorporated into the gelatin capsule via inclusion of an amount of immediate release memantine or a salt thereof, e.g., as a powder or granulate within the capsule. Alternatively, the gelatin capsule itself can be coated with an immediate release layer of memantine. One skilled in the art recognizes still other alternative means of incorporating an immediate release side-effect-reducing compound into the unit dose. By including an effective amount of immediate release side effect-reducing compound in the unit dose, the experience of adverse effects including nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression in subjects can be significantly reduced.

In certain aspect of the invention, the multilayer or bilayer tablet may comprise an immediate release layer comprising memantine and a controlled release layer comprising other pharmaceutically active agents. In one embodiment, the controlled release layer is capable of releasing about 30 to about 40% of the one or more pharmaceutically active agent contained therein in the stomach of a subject in about 5 to about 10 minutes following oral administration. In another embodiment, the controlled release layer is capable of releasing about 90% of the one or more pharmaceutically active agents are released in about 40 minutes after oral administration.

In one embodiment, a controlled release layer comprises from about 75 mg to about 250 mg of silicified microcrystalline cellulose, from about 10 mg to about 40 mg hydroxylmethylpropyl cellulose, from about 0.5 mg to 5 mg magnesium stearate, and from about 0.5 mg to about 5 mg stearic acid. The controlled release layer may comprise about 5 mg to 15 mg of phenylephrine, or about 7.5 mg to 12.5 mg of phenylephrine, or about 9.0 mg to about 11 mg of phenylephrine, or about 9.5 mg to about 10.5 mg of phenylephrine, or about 10 mg of phenylephrine. The controlled release layer may comprise about 50 mg to about 150 mg of guaifenesin, or about 75 mg to about 125 mg of guaifenesin or about 90 mg to about 110 mg of guaifenesin, or about 95 mg to about 105 mg of guaifenesin or about 100 mg of guaifenesin.

Controlled release formulations can comprise one or more combination of excipients that slow the release of the agents by coating or temporarily bonding or decreasing their solubility of the active agents. Examples of these excipients include cellulose ethers such as hydroxypropylmethylcellulose (e.g., Methocel K4M) or silicified microcrystalline cellulose, polyvinylacetate-based excipients such as, e.g., Kollidon SR, and polymers and copolymers based on methacrylates and methacrylic acid such as, e.g., Eudragit NE30D.

In a further embodiment, at least one pharmaceutically active agent in a controlled release form is antihistamine. In one embodiment of the invention, compositions comprise one or more carriers that protect the agents against rapid elimination from the body, such as time release formulations or coatings. Such carriers include controlled release formulations, including, for example, microencapsulated delivery systems. The active agents can be included in the pharmaceutically acceptable carrier in amounts sufficient to treat a subject's pain, with reduced adverse effects.

In certain embodiments the compositions are an oral dosage form and comprise a matrix that includes, for example, a controlled release material and another pharmaceutically active agent (e.g., to provide controlled release of the other pharmaceutically active agent). In certain embodiments, the matrix is compressible into a tablet and can be optionally overcoated with a coating that can control the release of the other pharmaceutically active agent from the composition. In this embodiment blood levels of other pharmaceutically active agent are maintained within a therapeutic range over an extended period of time. In certain alternate embodiments, the matrix is encapsulated.

Tablets or capsules containing a composition described herein can be coated or otherwise compounded to provide a dosage form affording the advantage of prolonged action. For example, the tablet or capsule can contain an inner dosage and an outer dosage component, the latter being in the form of an envelope over the former. The two components can be separated by an enteric layer that serves to resist disintegration in the stomach and permit the inner component to pass intact into the duodenum or to be controlled in release. For controlled extended release, the capsule can also have micro drilled holes.

A coating comprising a side-effect reducing compound, in immediate release form, can be added to the outside of a controlled release tablet core to produce a final dosage form. Such a coating can be prepared by admixing memantine with polyvinylpyrrolidone (PVP) 29/32 or hydroxypropylmethylcellulose (HPMC) and water/isopropyl alcohol and triethyl acetate. Such an immediate release coating can be spray coated onto the tablet cores. The immediate-release coating can also be applied using a press-coating process with a blend consisting of 80% by weight memantine and 20% by weight of lactose and hydroxypropyl methylcellulose type 2910. Press-coating techniques are known in the art and are described in U.S. Pat. No. 6,372,254, which is herein incorporated by reference in its entirety for all purposes.

The immediate release or controlled release dosage forms described herein can also take the form of a bi-layered tablet, which comprises a first layer and a second layer. The first layer comprises a first drug that is an NMDA receptor antagonist, for example, memantine. The second layer comprises a second drug that is an analgesic (for example an opiate), antitussive, antihistamine, expectorant, decongestant or a nasal decongestant. The bi-layered tablet can provide a plasma concentration within the therapeutic range of the second drug over a period which is coextensive with at least about 70% of the period (e.g., 12 hours) within which the bi-layered tablet provides a plasma concentration within the therapeutic range of the first drug.

Lozenge

In another embodiment, the compositions of the present invention are in the form of a hard lozenge or a buccal tablet containing sufficient flavorants, pH modifiers, permeation enhancers, and/or urinary acidification agents, etc. that will maintain acceptable flavor while maximizing the uptake of memantine (and optionally decreasing the elimination half-life) and other actives within the pregastric GI tract. The pH of such solid dosage forms can be determined by dissolving the solid dosage in artificial saliva at a concentration of 10% of the solid composition and determining the pH of the resulting solution or suspension. (See Fusayema et al., infra, which is incorporated herein by reference in its entirety for all purposes). A particular embodiment may include a throat lozenge or a cough drop.

A throat lozenge or cough drop is a small, medicated sweet intended to be dissolved slowly in the mouth to lubricate and soothe irritated tissues of the throat (usually due to a sore throat), possibly from the common cold or influenza. Cough tablets have taken the name lozenge, based on their original shape. Conventional lozenges intended for treating cough may contain benzocaine, an anesthetic, or eucalyptus oil. Non-menthol throat lozenges generally use either zinc gluconate, glycine or pectin as an oral demulcent. Several brands of throat lozenges contain dextromethorphan. Still other varieties, such as Halls®, contain menthol, peppermint oil and/or spearmint as their active ingredient(s). Honey lozenges are also available. Most throat lozenges should be taken in moderation, due to the fact that some active ingredients could be hazardous to the health if consumed in large amounts. Because of their antibacterial properties, some throat lozenges can double as breath fresheners, eliminating odor-causing bacteria in the mouth.

In a certain embodiments, the composition according to the invention further comprises microcrystalline cellulose ("mcc"). Certain specific embodiments may also utilize other forms of carriers, in addition to or including mcc, such as but not limited to fibrous material or carbohydrates including cellulose (including hemicellulose, celluloses with different crystallinities and structures {e.g., varying structures including solid fibers, and addition or including fibers or the like in various structures such as web-like structures and/or other structures}, including naturally occurring celluloses including *Cladophora* sp. Algae cellulose or the like), dextran, agarose, agar, pectin, alginate, xanthan, chitosan, starch (including potato starch, shoti starch) etc. or mixtures thereof. Suitable carriers are also disclosed in WO 2004/064811, which is hereby incorporated by reference. More specifically, it is contemplated that a relatively high surface area may be of importance for a carrier that is suitable for use. Accordingly, the specific surface area of suitable carriers is normally at least 0.7 $m^2/g$ such as, e.g., 1 $m^2/g$. In certain uses, the specific surface area may range between about 0.7 $m^2/g$ and at least about 100 $m^2/g$ and/or may be anything within this range and/or may be any mixture of sizes within this range. For example, in certain embodiments, the surface area may be about 0.7 m²/g, about 1 m²/g, about 1.5 m²/g, about 2.0 m²/g, about 3.0 m²/g, about 5 m²/g, about 7 m²/g, about 10 m²/g, about 15 m²/g, about 20 m²/g, about 25 m²/g, about 35 m²/g, about 45 m²/g, about 50 m²/g, about 75 m²/g, about 100 m²/g and above about 100 m²/g, or combinations thereof. Such carriers having such suitable surface areas may include any of the carriers described herein.

The lozenges of the present invention comprise memantine in a candy base, including absorption enhancing agents (e.g., alkalizing agents, pH adjusting agents, permeation enhancing agents, or any combination thereof, etc.) and optionally additional pharmaceutically active agents. The candy (or lozenge) base can include sweeteners such as isomalt, glucose, corn syrup, sorbitol, maltitol, etc. or artificial sweeteners such as acesulfame potassium, sucralose, aspartame, etc. in which the active ingredient(s) (memantine, optionally other pharmaceutically active ingredients as described herein) and excipients are dispersed or dissolved. In another embodiment the dosage form can be in a candy form (e.g., matrix), such as a lollipop or lozenge. In one embodiment one or more pharmaceutically active agents is dispersed within a candy matrix. In one embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose may be utilized, or sugar alcohols suitable for use with diabetic patients, such as sorbitol or mannitol might be employed. Other sweeteners, such as the aspartames, sucralose, or potassium acesulfame can also be easily incorporated into a composition in accordance with compositions described herein. The candy base may be very soft and fast dissolving, or may be hard and slower dissolving.

In particular embodiments, the lozenges of the present invention comprise, in addition to memantine and other optional pharmaceutically active ingredients, a carrier such as acacia, alginic acid, carbomer, carboxymethylcellulose, calcium, carboxymethylcellulose sodium, microcrystalline cellulose, cellulose, dextrates, dextrin, dextrose, ethylcellulose, fructose, gelatin, guar gum, hydroxyethyl cellulose, hydroxypropyl cellulose, hydroxypropyl methylcellulose, lactitol, lactose, lecithin, maltodextrin, mannitol, methylcellulose, poloxamer, polyethylene glycol, polymethacrylates, polyoxyethylene alkyl ethers, polyvinyl alcohol, povidone, propylene glycol alginate, sodium alginate, sodium ascorbate, sodium starch glycolate, sorbitol, starch, starch (pregelatinized), sucrose, tragacanth, trimethylglycine, xanthan gum, xylitol, zein and combinations thereof. The memantine (and other optional pharmaceutically active ingredients) is typically mixed with the carrier to form a dispersion therein, using methods known in the art for forming lozenges. Additional excipients, as described herein, can also be added. For example such additional excipients can include permeation enhancers and/or elimination enhancers (as described herein) as well as other excipients known in the art such as absorbents, colorants (dyes such as FD&C Red 40, FD&C Yellow 5, FD&C Yellow 6, FD&C Blue 1, FD&C Blue 2, etc.), flavoring agents (such as black cherry, lemon, menthol, etc.), solvents and co-solvents, coating agents, direct compression excipients, disintegrants, glidants, lubricants, opaquants, polishing agents, suspending agents, sweetening agents, antiadherents, binders, preservatives, clarifying agents, emulsifying agents, antioxidants, plasticizers, surfactants, tonicity agents, and viscosity increasing agents.

When the lozenge includes a urinary acidification agent (such as e.g., ammonium chloride), the urinary acidification agent can be coated with a polymeric taste-masking coating or layer as described herein, for example a water insoluble polymer such as ethyl cellulose or Eudragit NE30D, or reverse enteric polymers such as Eudragit E100 or EPO, enteric polymer such as Eudragit L100 or S100. The polymeric taste-masking coating can optionally include pore forming agents such as hydroxypropyl methylcellulose, hydroxypropyl cellulose, etc., and plasticizers such as triethyl citrate, polyethylene glycol, dibutyl sebacate, etc.

Liquid Dosage Forms

Another embodiment of the present invention comprises a liquid containing safe and effective amount of memantine, and an orally acceptable pharmaceutical carrier, the composition having pH about 8 to about 11, for example from about 8.4 to about 10, or from about 8.5 to about 9.5 or about 8, about 8.2, about 8.4, about 8.6, about 8.8, about 9.0, about 9.2, abut 9.4, about 9.6, about 9.8, about 10.0, about 10.2, about 10.4, about 10.6, about 10.8, or about 11.0, inclusive of all ranges and subranges therebetween. The compositions of the present invention can include menthol, ethanol and other alcohols to enhance flavor to maximize permeability. The compositions of the subject invention will optimally have a basic buffering strength sufficient to overcome that provided by the saliva and mucus membranes of the mouth and throat, such that the composition mixed with the saliva is retained in the above pH ranges during the period that it is in the mouth and throat. Consequently, the compositions of the subject invention will have a basic buffer strength of at least about 0.01 milliequivalents (mEq) base per unit dose, from about 0.05 mEq to about 2.5 mEq per unit dose, or from about 0.1 mEq to about 1.5 mEq per unit dose. The compositions of the present invention may comprise a pharmaceutically-acceptable carrier comprising a pharmaceutically-acceptable buffer system. Examples of pharmaceutically-acceptable buffer systems useful in the compositions of the present invention include, but are not limited to, phosphate buffer systems which are a mixture of salts of monohydrogen and dihydrogen phosphate, sodium hydroxide/glycine buffer systems, and carbonate and hydrogen carbonate buffer systems. Particularly useful buffer systems for the compositions of the present invention are phosphate buffer systems. Other ingredients of the subject invention include the urine acidifying agents calcium chloride, ammonium chloride, sodium biphosphate, sodium acid phosphate, glutamic acid hydrochloride, methionine and other amino acids, encased within a polymeric coating such as ethyl cellulose or hydroxypropylmethyl cellulose to protect taste and reduce chemical reactivity with the basic agents described above. One of the particular embodiments may be elixir/syrup.

An elixir is a hydro-alcoholic solution of at least one active ingredient. The alcohol is mainly used to solubilize the active ingredient(s) and some excipients, retard the crystallization of sugar, preserve the finished product, provide a certain sharpness to the taste, aid in masking the unpleasant taste of the active ingredient(s), and enhance the flavor.

The lowest alcoholic quantity that will dissolve completely the active ingredient(s) and give a clear solution is generally chosen. High concentrations of alcohol give burning taste to the final product.

An elixir may also contain the following excipients:
Sugar and/or sugar substitutes like the sugar polyols glycerol and sorbitol.
Preservatives like parabens and bezoates and antioxidants like butylated hydroxytoluene (BHT) and sodium metabisulfite.

Buffering agents

Chelating agents like sodium ethylenediaminetetraacetic acid (EDTA)

Flavoring agents and flavor enhancers

Coloring agents

Liquid compositions of the present invention can for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrin derivatives, sorbitan monolaurate, triethanolamine sodium acetate, triethanolamine oleate, and the other such agents. Methods of preparation such dosage forms are known, or will be apparent, to those skilled in the art; for example, see Remington's Pharmaceutical Sciences, Mack Publishing Company, Easton, Pa., 15$^{th}$ edition, 1975.

In various embodiments, the liquid compositions of the present invention can be in the form of elixirs, syrups, sprays (nasal, buccal, sublingual, etc.).

Compositions Comprising Buffer Systems

Some ionized drugs, including ionized memantine are poorly soluble in aqueous media. These drugs can be delivered as oral dosages. Oral administration, however, has several disadvantages, such as drug losses during hepatic first pass metabolism, during enzymatic degradation within the GI tract, and during absorption. Accordingly, other routes of drug administration have been investigated, including those involving transport across the mucous membranes. The extent of drug delivery is dependent on the properties of drugs being delivered through these membranes. The ability of a molecule to pass through any mucous membrane is dependent upon its size, its lipid solubility, and the extent to which it is ionized, among other factors. The extent to which a drug is ionized has further been investigated with respect to drug delivery across the mucous membranes. Ionization is dependent on the dissociation constant (pKa), and the pH of the molecule's surrounding environment. In its un-ionized form, a drug is sufficiently lipophilic to traverse a membrane via passive diffusion. In fact, according to the pH partition hypothesis, only un-ionized, non-polar drugs will penetrate a lipid membrane.

At equilibrium, the concentrations of the un-ionized form of the drug are equal on both sides of the membrane. As the concentration gradient drives passive diffusion, an increase in the percentage of the un-ionized form of a drug correspondingly increases the transmucosal absorption of the drug. Maximum absorption across the membrane is thought to occur when a drug is 100% in its un-ionized form. Similarly, absorption across the membrane decreases as the extent of ionization increases. Therefore, one may influence the extent of drug absorption across the mucous membranes of the oral cavity by altering the pH of the local mucous membranes.

Altering the pH of the saliva can be done by using buffer systems. U.S. Pat. No. 7,658,945, which is incorporated herein for its entirety, discloses a binary buffering system which is capable of achieving and sustaining a final pH independent of the initial pH in order to increase transmucosal absorption. U.S. Pat. No. 7,658,945 discloses compositions for delivering agents across the oral mucosa with a buffer system that produces a final pH independent of the initial pH, and sustains that final pH for a given period of time. In addition, these compositions are capable of rapidly facilitating substantially complete conversion of an active agent from its ionized form to its un-ionized form.

In particular, the buffer system in the compositions of the present invention can raise the pH of the local absorption sites to a pH greater than about 7.8, thereby facilitating the substantially complete conversion of memantine from its ionized to its un-ionized form. As a result, the dose of memantine is rapidly and efficiently absorbed through the membranes with surprisingly low inter-subject variability.

As used herein, the phrase "substantially complete conversion of an agent from its ionized to its un-ionized form" refers to greater than about 50% conversion of the agent from its ionized form into its un-ionized form. For example, the buffer system may favor at least about 50%, 55%, 60%, 65%, 70%, 75%, 80%, 85%, 90%, 95%, or 99% conversion of the agent from its ionized form into its un-ionized form. In some embodiments, the conversion can occur within about 10 minutes following administration. The term "administration" here refers to administration of the aforementioned compositions comprising buffer systems to the mucous membranes of the oral cavity (i.e., oral mucosa). Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. In particular embodiments, the aforementioned compositions comprising buffer systems are administered to the sublingual mucosa, buccal mucosa, or a combination thereof.

In one aspect, the present invention can be a solid composition for delivery of memantine across the oral mucosa, the composition comprising:

(a) memantine, and a pharmaceutically acceptable salt thereof, (b) a carrier that provides complete buccal or sublingual disintegration in about 5 minutes or less following administration to the mouth; and (c) a binary buffer system comprising a carbonate salt and a bicarbonate salt, wherein the binary buffer system raises the pH of saliva to a pH greater than about 7.8, irrespective of the starting pH of saliva.

In certain instances, the binary buffer system can raise the pH of saliva to a pH greater than about 8.5 irrespective of the starting pH of saliva. In certain other instances, the binary buffer system can raise the pH of saliva to a pH greater than about 9 (e.g., about 9-11), irrespective of the starting pH of saliva. Any form of memantine is suitable for use in the compositions described herein, e.g., a salt form of memantine (memantine hydrochloride), a free base form of memantine, or a mixture thereof.

The buffer systems of the compositions described herein are capable of raising the pH of saliva to a pH greater than about 7.8, irrespective of the starting pH of saliva. In this way, the buffer system helps convert substantially all of the memantine from its ionized form to its un-ionized form. Alternatively, the buffer system helps ensure that memantine, initially in an un-ionized form, remains in an un-ionized form. Although basic buffering agents are typically used in the buffer systems of the present invention, one skilled in the art will appreciate that acidic agents can also be used to adjust the pH of the buffer system as long as the buffer system as a whole raises the pH of saliva to a pH greater than about 7.8.

In one embodiment, the present invention provides binary buffer systems comprising a carbonate salt and a bicarbonate salt. The concentration of each buffer system component is tailored such that the final salivary pH is achieved and sustained for a period of time, e.g., for at least about 2 minutes, at least about 5 minutes, at least about 10 minutes, at least about 20 minutes, or at least about 60 minutes. This typically involves a sensory and safety trial and error type of procedure of adding various amounts of each buffer system component and then measuring the final pH over time. In this way, selection of an appropriate weight ratio for each buffer system component can be easily determined in just a few trials. For example, the weight ratio of carbonate salt to bicarbonate salt can be from about 1:10 to about 10:1, or from about 1:5 to about 5:1, more preferably from about 1:3 to about 3:1, and in other embodiments from about 1:2 to about 2:1.

The carbonate salt is generally selected from sodium carbonate, potassium carbonate, calcium carbonate, ammonium carbonate, and magnesium carbonate. In some embodiments, the carbonate salt is sodium carbonate or potassium carbonate. In particular embodiments, the carbonate salt is sodium carbonate. Similarly, the bicarbonate salt is generally selected from sodium bicarbonate, potassium bicarbonate, calcium bicarbonate, ammonium bicarbonate, and magnesium bicarbonate. In some embodiments, the bicarbonate salt is sodium bicarbonate or potassium bicarbonate. In particular embodiments, the bicarbonate salt is sodium bicarbonate. In some embodiments, a dessicant-coated sodium bicarbonate can be used. The amount of carbonate salt and bicarbonate salt used in the binary buffer system is an amount that is sufficient to raise salivary pH to a pH of about 7.8 or more, for example about 8.5 or more, and in other embodiments about 9 or more (e.g., about 9-11), irrespective of the starting pH. In certain instances, the amount of bicarbonate salt is greater than or equal to the amount of carbonate salt, and the weight ratio of carbonate salt to bicarbonate salt is from about 1:1 to about 1:10, for example from about 1:1 to about 1:5, and in other embodiments from about 1:1 to about 1:2, e.g., 1:1, 1:1.1, 1:1.2, 1:1.3, 1:1.4, 1:1.5, 1:1.6, 1:1.7, 1:1.8, 1:1.9, or 1:2. Alternatively, the amount of bicarbonate salt is less than or equal to the amount of carbonate salt, and the weight ratio of carbonate salt to bicarbonate salt is from about 1:1 to about 10:1, for example from about 1:1 to about 5:1, and in other embodiments from about 1:1 to about 2:1, e.g., 1:1, 1.1:1, 1.2:1, 1.3:1, 1.4:1, 1.5:1, 1.6:1, 1.7:1, 1.8:1, 1.9:1, or 2:1. In certain other instances, the combined amount of carbonate salt and bicarbonate salt is greater than or equal to the amount of memantine, and the weight ratio of carbonate salt and bicarbonate salt to memantine is from about 1:1 to about 10:1, e.g., 1:1, 2:1, 3:1, 4:1, 5:1, 6:1, 7:1, 8:1, 9:1, or 10:1. Alternatively, the combined amount of carbonate salt and bicarbonate salt is less than or equal to the amount of memantine, and the weight ratio of carbonate salt and bicarbonate salt to memantine is from about 1:1 to about 1:10, e.g., 1:1, 1:2, 1:3, 1:4, 1:5, 1:6, 1:7, 1:8, 1:9, or 1:10.

In view of the above, the buffer systems of the present invention are binary buffer systems containing sodium carbonate and sodium bicarbonate.

Alternatively, in another embodiment, the buffer systems of the present invention are binary buffer systems comprising a carbonate salt or a bicarbonate salt and a second buffering agent. The concentration of each buffer system component is tailored such that the final salivary pH is achieved and sustained for a period of time, e.g., for at least about 2 minutes, at least about 5 minutes, at least about 10 minutes, at least about 20 minutes, or at least about 60 minutes.

The second buffering agent is generally selected from a metal oxide such as magnesium oxide or aluminum oxide; a citrate salt such as sodium citrate, potassium citrate, calcium citrate, magnesium citrate, and ammonium citrate; a phosphate salt such as monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate; a borate salt such as sodium borate, potassium borate, calcium borate, magnesium borate, and ammonium borate; an ascorbate salt such as potassium ascorbate or sodium ascorbate; an acetate salt such as potassium acetate or sodium acetate; and alkaline starch. However, one skilled in the art will appreciate that any metal oxide or salt of citric acid, phosphoric acid, boric acid, ascorbic acid, or acetic acid is suitable for use in the buffer systems of the present invention.

Alternatively, in still yet another embodiment, the buffer systems of the present invention are ternary buffer systems comprising a carbonate salt, a bicarbonate salt, and a third buffering agent. The third buffering agent is generally selected from a metal oxide, a citrate salt, a phosphate salt, a borate salt, an ascorbate salt such as potassium ascorbate or sodium ascorbate, an acetate salt such as potassium acetate or sodium acetate, and alkaline starch. Suitable metal oxides include, without limitation, magnesium oxide and aluminum oxide. Suitable citrate, phosphate, and borate salts include, without limitation, any salt of citric acid, phosphoric acid, or boric acid known in the art such as those described above.

In certain instances, the buffer system comprises a carbonate salt or a bicarbonate salt, a citrate salt, and a borate salt. In certain other instances, the buffer system comprises a carbonate salt or a bicarbonate salt, a phosphate salt, and a borate salt. In some embodiments, the metal oxide is amorphous magnesium oxide.

While the foregoing discussion has focused on the ability of the buffer system to alter salivary pH to favor substantial conversion to the un-ionized form of a therapeutic agent, it is conceivable that the buffer system may also have subsidiary beneficial effects on the extent of absorption across the oral mucosa. For example, the buffer system may create a final salivary pH that in turn affects the molecular configuration of the therapeutic agent in a way in which absorption across the oral mucosa is increased. It is to be understood that these subsidiary beneficial effects of the buffer system are within the general scope of the buffer system and compositions herein described.

The compositions comprising buffer systems can be administered in various dosage forms as described in U.S. Pat. No. 7,658,945 which is incorporated herein for its entirety. The compositions comprising buffer systems can include other active agents disclosed throughout this application, in combination with memantine or a pharmaceutically acceptable salt thereof.

Embodiments

In certain embodiments, the present invention is directed to an antitussive pharmaceutical composition comprising memantine, optionally in combination with other pharmaceutically active agents.

In some other embodiments, the antitussive composition of the present invention is substantially free of sugar.

In some embodiments, the antitussive composition of the present invention is substantially free of alcohol.

In some other embodiments, the antitussive composition of the present invention is substantially free of both sugar and alcohol.

In some other embodiments, the antitussive composition of the present invention comprises a non-sugar sweetening agent.

In some embodiments, the non-sugar sweetening agent comprising saccharin sodium, maltodextrin, aspartame, potassium acesulfame, neohesperidin dihydrochalcone, sucralose, monoammonium glycyrrhizinate, and mixtures thereof.

In some other embodiments, the antitussive composition of the present invention comprises therapeutically effective amounts of phenylephrine and therapeutically effective amounts of guaifenesin.

In certain other embodiments, the antitussive composition of the present invention comprises about 1 mg/dose to about 35 mg/dose memantine; about 5 mg/dose to about 15 mg/dose phenylephrine; and/or about 50 mg/dose to about 150 mg/dose guaifenesin.

In some other embodiments, the antitussive composition of the present invention comprises about 4 mg/dose to about 25 mg/dose of memantine; about 7.5 mg/dose to about 25 mg/dose memantine; about 7.5 mg/dose to about 12.5 mg/dose phenylephrine; and/or about 75 mg/dose to about 125 mg/dose guaifenesin.

In some other embodiments, the antitussive composition of the present invention comprises about 15 mg/dose to about 22 mg/dose memantine; about 9 mg/dose to about 11 mg/dose phenylephrine; and/or about 90 mg/dose to about 110 mg/dose guaifenesin.

In some other embodiments, the antitussive composition of the present invention comprises about 19 mg/dose to about 21 mg/dose memantine; about 9.5 mg/dose to about 11.5 mg/dose phenylephrine; and/or about 95 mg/dose to about 105 mg/dose guaifenesin. In some other embodiments, the antitussive composition of the present invention comprises about 20 mg/dose memantine; about 10 mg/dose phenylephrine; and/or about 100 mg/dose guaifenesin.

In particular embodiments the antitussive compositions of the present invention comprise about 7.5 mg/dose, about 15 mg/dose, or about 25 mg/dose of memantine.

In certain other embodiments of the present invention, the antitussive composition of the present invention comprises memantine in combination with one or more of the group consisting of codeine, codeine phosphate, codeine sulfate, hydrocodone, morphine, morphine sulfate, hydromorphone hydrochloride, levorphanol tartrate, fentanyl, fentanyl citrate, oxycodone hydrochloride, oxymorphone hydrochloride, methadone hydrochloride, apomorphine hydrochloride, beechwood creosote, benzonatate, camphor ethanedisulfonate, diphenhydramine, diphenhydramine hydrochloride, dextromethorphan, dextromethorphan hydrobromide, chlophendianol hydrochloride, carbetapentane citrate, caramiphen edisylate, noscapine, noscapine hydrochloride, or menthol.

In some embodiments of the antitussive composition of the present invention memantine is used in combination with any of the antitussives, expectorants, decongestants, nasal decongestants and opioid analgesics as described herein.

In some embodiments, the nasal decongestant comprises one or more of the group consisting of ephedrine, ephedrine sulfate, ephedrine hydrochloride, pseudoephedrine hydrochloride, epinephrine bitartrate, hydroxyamphetamine hydrobromide, propylhexedrine, phenylpropanolamine hydrochloride, mephentermine sulfate, methoxamine hydrochloride, naphazoline hydrochloride, oxymetalozine hydrochloride, tetrahydrozoline hydrochloride, or xylometazoline hydrochloride.

In certain other embodiments of the invention, the opioid analgesic comprises one or more of the group consisting of codeine, morphine, hydromorphone, hydrocodone, oxymorphone, levorphanol, fentanyl, propoxyphene, diphenoxylate, meperidine, methadone, and oxycodone.

In some embodiments of the present invention, the expectorant comprises one or more of the group consisting of ammonium chloride, ammonium carbonate, acetylcysteine, antimony potassium tartrate, glycerin, potassium iodide, sodium citrate, terpin hydrate, and tolu balsam.

In some embodiments of the present invention, the mucolytic comprises one or more of the groups consisting of acetylcysteine, ambroxol, bromhexine, carbocisteine, domiodol, dornase alfa, eprazinone, erdosteine, letosteine, mesna, neltenexine, sobrerol, stepronin, tiopronin, and combinations thereof.

In some other embodiments of the present invention, the composition further comprises a flavorant, and wherein the flavorant can be a natural flavorant or an artificial flavorant.

In certain embodiments of the present invention, the expectorant comprises one or more of the group consisting of anise oil, cinnamon oil, peppermint oil, spearmint oil, oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, and grape oil.

In some embodiments, the flavorant further comprises one or more of the fruit essence selected from apple essence, pear essence, peach essence, berry essence, wildberry essence, date essence, blueberry essence, kiwi essence, strawberry essence, raspberry essence, cherry essence, black cherry essence, plum essence, pineapple essence, and apricot essence.

In certain other embodiments of the present invention, the antitussive composition comprising memantine is an oral dosage form. In some other embodiments, the oral dosage form includes but is not limited to pills, tablets, capsules or lozenges. In some embodiments, the oral dosage form is an orally disintegrating tablet (ODT). In some other embodiments, the oral dosage form is an orally dissolving film (ODF). In other embodiments, the oral dosage form is a lozenge. In some other embodiments, the oral dosage form is a tablet. In some embodiments of the present invention, the tablet is a bi-layered or multi-layered tablet. In some other embodiments the oral tablet comprises therapeutically effective amounts of other pharmaceutically active agents. In certain other embodiments of the invention, the oral tablet comprises an immediate release layer comprising memantine and a controlled release layer comprising other pharmaceutically active agents. In yet another embodiment of the present invention the oral tablet comprises an immediate release layer comprising memantine and a controlled release layer comprising other pharmaceutically active agents. In some embodiments of the invention, the immediate release layer of the oral tablet further comprises other pharmaceutically active agents in addition to memantine. In some other embodiments, the immediate release layer of the oral tablet comprises guaifenesin. In certain other embodiments, the immediate release layer comprises phenylephrine. In some other embodiments, the oral tablet comprises an immediate release layer comprising memantine and a controlled release layer comprising guaifenesin. In some other embodiments, the oral tablet comprises an immediate release layer comprising memantine and a controlled release layer comprising phenylephrine. In some other embodiments, the oral tablet comprises an immediate release layer comprising memantine and a controlled release layer comprising phenylephrine and guaifenesin.

In one embodiment, the composition is in the form of a multi-layered tablet having at least one immediate-release layer comprising memantine and at least one controlled-release layer comprising one or more other pharmaceutically active agents.

In other embodiments of the present invention, is provided a method of administering any of the compositions disclosed herein to treat cough of a patient in need thereof. In one embodiment, the cough may be acute. In another embodiment, the cough may be chronic. In another embodiment, the cough may include both an acute cough and a chronic cough.

In some other embodiments of the present invention, the compositions disclosed herein are liquid dosage forms administered in a dose unit from about 0.1 mL to about 100 mL.

In certain other embodiments of the present invention, the disclosed compositions which are administered to a patient in need thereof, are substantially free of one or more of another antitussive, another decongestant, another nasal decongestant, another opioid analgesic or another expectorant.

In some other embodiments of the present invention, the compositions administered are comprised of one or more of another active ingredient selected from the group consisting of another antitussive, another decongestant, another nasal decongestant, another opioid analgesic or another expectorant.

In certain other embodiments, the method of administration comprises administering a composition comprising another antitussive, and that another antitussive comprising one or more of the group consisting of codeine, codeine phosphate, codeine sulfate, hydrocodone, morphine, morphine sulfate, hydromorphone hydrochloride, levorphanol tartrate, fentanyl, fentanyl citrate, oxycodone hydrochloride, oxymorphone hydrochloride, methadone hydrochloride, apomorphine hydrochloride, beechwood creosote, benzonatate, camphor ethanedisulfonate, diphenhydramine, diphenhydramine hydrochloride, dextromethorphan, dextromethorphan hydrobromide, chlophendianol hydrochloride, carbetapentane citrate, caramiphen edisylate, noscapine, noscapine hydrochloride, or menthol.

In certain other embodiments, the method of administration comprises administering a composition comprising another nasal decongestant, and that another nasal decongestant comprising one or more of the group consisting of ephedrine, ephedrine sulfate, ephedrine hydrochloride, pseudoephedrine hydrochloride, epinephrine bitartrate, hydroxyamphetamine hydrobromide, propylhexedrine, phenylpropanolamine hydrochloride, mephentermine sulfate, methoxamine hydrochloride, naphazoline hydrochloride, oxymetalozine hydrochloride, tetrahydrozoline hydrochloride, or xylometazoline hydrochloride.

In certain other embodiments, the method of administration comprises administering a composition comprising another opioid analgesic, and that another opioid analgesic comprising one or more of the group consisting of codeine, morphine, hydromorphone, hydrocodone, oxymorphone, levorphanol, fentanyl, propoxyphene, diphenoxylate, meperidine, methadone, and oxycodone.

In certain other embodiments, the method of administration comprises administering a composition comprising another expectorant, and that another expectorant comprising one or more of the group consisting of ammonium chloride, ammonium carbonate, acetylcysteine, antimony potassium tartrate, glycerin, potassium iodide, sodium citrate, terpin hydrate, and tolu balsam.

Some embodiments of the present invention include the method of administration of the compositions of the present invention to a patient in need thereof. In some embodiments, such compositions are substantially free of sugar. In other embodiments, such compositions include sugar. In yet other embodiments, such compositions are substantially free of alcohol. In some embodiments, such compositions are substantially free of both sugar and alcohol.

In certain other embodiments, the present invention includes a method of administration of disclosed compositions to a patient in need thereof, wherein such compositions comprising non-sugar sweetening agent. In certain other embodiments, the non-sugar sweetening agent comprises one or more of the group selected from saccharin sodium, maltodextrin, aspartame, potassium acesulfame, neohesperidin dihydrochalcone, sucralose, monoammonium glycyrrhizinate, and mixtures thereof.

In some other embodiments, the present invention includes a method of administration of disclosed compositions to a patient in need thereof, wherein such compositions comprising citric acid, edetate disodium, glycerin, methylparaben, propylparaben, propylene glycol, saccharin sodium, sodium citrate, sorbitol, water, FD&C red 40, and artificial cherry flavor.

In certain other embodiments, the present invention includes a method of administration of disclosed compositions to a patient in need thereof, wherein such compositions comprising therapeutically effective amounts of phenylephrine and therapeutically effective amounts of guaifenesin. In some embodiments, such compositions comprising about 1 mg/dose to about 35 mg/dose memantine; about 5 mg/dose to about 15 mg/dose phenylephrine; and/or about 50 mg/dose to about 150 mg/dose guaifenesin. In some other embodiments, such compositions comprising about 7.5 mg/dose to about 25 mg/dose memantine; about 7.5 mg/dose to about 12.5 mg/dose phenylephrine; and/or about 75 mg/dose to about 125 mg/dose guaifenesin. In yet another embodiments, such compositions comprising about 15 mg/dose to about 22 mg/dose memantine; about 9 mg/dose to about 11 mg/dose phenylephrine; and/or about 90 mg/dose to about 110 mg/dose guaifenesin. In certain other embodiments, such compositions comprising about 9 mg/dose to about 21 mg/dose memantine; about 9.5 mg/dose to about 10.5 mg/dose phenylephrine; and/or about 95 mg/dose to about 105 mg/dose guaifenesin. In yet another embodiment, such compositions comprise about 20 mg/dose memantine; about 10 mg/dose phenylephrine; and/or about 100 mg/dose guaifenesin.

In some embodiments, the present invention includes administering the disclosed compositions to a patient in need thereof, wherein the compositions are administered as a liquid dosage form. In other embodiments, the dosage form is a tablet, caplet, lozenge, and wafer. In some other embodiments, the dosage form is in the form of a vapor or an inhalant. In some other embodiments, the compositions disclosed herein are administered as a spray. In some other embodiments, the compositions disclosed herein are administered as a buccal or sublingual formulation. In some other embodiments, such sublingual or buccal formulations are in the form of discrete droplets containing memantine and optionally other active agents as described herein. In some other embodiments, the droplet size of such discrete droplets is at least 10 microns.

In certain embodiments, the present invention comprises an antitussive composition for treatment of cough, said antitussive composition comprising memantine, wherein memantine is released rapidly at the site of absorption to achieve therapeutically effective blood levels in a patient in need thereof.

Another embodiment is an antitussive composition for treatment of cough, wherein memantine is released rapidly at the site of absorption and wherein the composition is administered as an oral dosage form. In some other embodiments, such oral dosage form is an enterically coated tablet. In certain other embodiments, the enterically coated tablet is a multi-layered tablet. In some other embodiments, the multi-layered enterically coated tablet comprises,

- a pH dependent polymeric outermost layer;
    - a first inner layer adjacent to the outermost layer comprising one or more of the agents selected from the group consisting of pH modifiers and permeation enhancers;
    - a second inner layer adjacent to the first inner layer comprising memantine and other actives; and
    - an innermost layer consisting of encased urine acidifying agents.

In certain other embodiments, the pH dependent outermost layer of the enterically coated tablet comprises Eudragit L30 D-55. In some embodiments, the innermost layer of the enterically coated tablet comprises Ammonium Chloride, Calcium Chloride, Sodium Phosphate Dibasic Anhydrous, Potassium Phosphate dibasic, Ascorbic acid, Ammonium Dihydrogen Phosphate, Glutamic acid, aspartame, ammonium phosphate monobasic and Methionine.

In some other embodiments, the present invention comprises an antitussive composition in the form of an oral dosage form. In some embodiments such oral dosage form is a fast dissolving tablet. In some other embodiments, the fast dissolving tablet comprises binders, disintegrants, lubricants, glidants, flavorants, sweeteners and colorants, and further comprising one or more of the agents selected from the group consisting of buffering agents, absorption enhancers, and urine acidification agents.

In some other embodiments, the oral dosage form of the present invention is a lozenge. In some other embodiments, the lozenge comprises binders, disintegrants, lubricants, glidants, flavorants, sweeteners and colorants, and further comprising one or more of the agents selected from the group consisting of buffering agents, absorption enhancers, and urine acidification agents.

In certain other embodiments, the oral dosage form of the present invention is an elixir or syrup. In some other embodiments, the elixir or syrup comprises sugar and sugar substitutes, preservatives, antioxidants, buffering agents, chelating agents, flavoring agents, and coloring agents, and further comprising one or more of the agents selected from the group consisting of buffering agents, absorption enhancers, and urine acidification agents.

In certain embodiments, the present invention includes a method of treating chronic cough in a patient in need thereof, which method comprises administering any of the disclosed compositions disclosed herein.

In certain other embodiments, the present invention includes a method of treating chronic cough in a patient in need thereof, which method comprises administering any of the disclosed compositions disclosed herein, wherein such composition is a rapid release memantine composition.

In certain other embodiments, the present invention is a composition comprising a therapeutically effective amount of first generation antihistamine and a therapeutically effective amount of memantine, wherein upon administration to a patient in need thereof, the composition is substantially devoid of sedating effects such as cognitive impairment and/or drowsiness. By substantially devoid of sedating effects, we mean that less than about 30%, or less than about 20%, or less than about 10% of the subjects administered a combination of memantine and a first-generation an antihistamine exhibit signs of sedation such as drowsiness. For example, the compositions of the present invention comprise a combination of a pharmaceutically effective amount of memantine and a pharmaceutically effective amount of diphenhydramine, wherein said combination is substantially devoid of sedating effects.

In some other embodiments, the composition further comprises decongestants, mucolytics and expectorants, antipyretics, analgesics and other antitussives. In certain other embodiments, the decongestants include second generation antihistamines, third generation antihistamines, derivatives of second generation antihistamines, and their delayed release forms, and amphetamines and adrenergic agents and their delayed release forms. In some embodiments, the mucolytics and the expectorants include guaifenesin and acetyl cysteine and their delayed release forms. In certain other embodiments, the antipyretics and the analgesics include acetaminophen, phenacetin, and mixed Cox-1 and Cox-2 inhibitors such as ibuprofen. In some embodiments, the other antitussive agents include menthol, dextromethorphan, hydrocodone, diphenhydramine and chlorphenhydramine, codeine and ambroxol.

In certain other embodiments, the present invention includes a method of treating acute cough of a patient in need thereof, which method comprises administering any of the compositions disclosed herein which comprises therapeutically effective amount of first generation antihistamine and a therapeutically effective amount of memantine. In certain other embodiments, such compositions are administered as an oral dosage form. In some embodiments such oral dosage form is an orally dissolving tablet, a sublingual tablet, lozenge, buccal tablet. In certain other embodiments, such oral dosage form in a syrup or elixir.

In various embodiments, the composition is in the form of any oral dosage form disclosed herein, including but not limited to a syrup, elixir, pill, tablet, or capsule.

One aspect of the present invention is an antitussive composition comprising memantine, an absorption enhancer and/or elimination enhancer. Another such embodiment further comprises one or more additional pharmaceutically active ingredients selected from the group consisting of antitussives other than memantine, expectorants, decongestants, nasal decongestants, and opioid analgesics. In such compositions, the one or more additional pharmaceutically active ingredients are in the form of an extended-release preparation.

In another embodiment, the antitussive composition is substantially free of pharmaceutically active ingredients other than memantine.

In another embodiment, the antitussive composition further comprises phenylephrine.

In one embodiment, the antitussive composition further comprises guaifenesin.

In another embodiment, the antitussive composition further comprises phenylephrine and guaifenesin. In one such embodiment, phenylephrine and guaifenesin are in the form of an extended-release preparation. In another such embodiment, the antitussive composition comprises about 1 mg/dose to about 30 mg/dose memantine; about 5 mg/dose to about 15 mg/dose phenylephrine; and/or about 50 mg/dose to about 150 mg/dose guaifenesin.

In one embodiment of the antitussive composition, the antitussive is selected from the group consisting of codeine, codeine phosphate, codeine sulfate, hydrocodone, morphine, morphine sulfate, hydromorphone hydrochloride, levorphanol tartrate, fentanyl, fentanyl citrate, oxycodone hydrochloride, oxymorphone hydrochloride, methadone hydrochloride, apomorphine hydrochloride, beechwood creosote, benzonatate, camphor ethanedisulfonate, diphenhydramine, diphenhydramine hydrochloride, dextromethorphan, dextromethorphan hydrobromide, chlophendianol hydrochloride, carbetapentane citrate, caramiphen edisylate, noscapine, noscapine hydrochloride, and menthol.

In another embodiment of the antitussive composition, the nasal decongestant is selected from the group consisting of ephedrine, ephedrine sulfate, ephedrine hydrochloride, pseudoephedrine, pseudoephedrine hydrochloride, epinephrine bitartrate, hydroxyamphetamine hydrobromide, propylhexedrine, phenylpropanolamine hydrochloride, mephentermine sulfate, methoxamine hydrochloride, naphazoline hydrochloride, oxymetalozine hydrochloride, tetrahydrozoline hydrochloride, and xylometazoline hydrochloride.

In another embodiment of the antitussive composition, the opioid analgesic is selected from the group consisting of codeine, morphine, hydromorphone, hydrocodone, oxymorphone, levorphanol, fentanyl, propoxyphene, diphenoxylate, meperidine, methadone, and oxycodone.

In another embodiment of the antitussive composition, the expectorant is selected from the group consisting of ammonium chloride, ammonium carbonate, acetylcysteine, antimony potassium tartrate, glycerin, potassium iodide, sodium citrate, terpin hydrate, and tolu balsam.

In another embodiment of the antitussive composition, the composition further comprises a flavorant.

In one particular embodiment, the antitussive composition comprises memantine and at least one absorption enhancer, and the absorption enhancer is a buffering agent or a permeation enhancer. In one such embodiment, the absorption enhancer is a buffering agent which maintains the memantine substantially in the form of a free-base during administration.

In another embodiment of the antitussive composition, the composition comprises memantine and at least one elimination enhancer, and the elimination enhancer is a urinary acidification agent.

In another embodiment, the absorption enhancer is a permeation enhancer, and the permeation enhancer is chitosan.

In another embodiment, the absorption enhancer is a permeation enhancer, and the permeation enhancer is menthol.

In one another embodiment of the antitussive composition, the urinary acidification agent is selected from the group consisting of calcium chloride, ammonium chloride, sodium biphosphate, sodium acid phosphate, glutamic acid hydrochloride, methionine and other amino acids.

In another embodiment of the antitussive composition, after administration, the memantine plasma concentration is 70-150 ng/mL at a $T_{max}$ of no more than about 2 hours. In another embodiment of the antitussive composition, after administration, the memantine plasma concentration is 70-150 ng/mL at a $T_{max}$ of no more than about 3 hours.

In another embodiment of the antitussive composition, after administration, the $C_{max}$ of memantine is about 20-30 ng/mL and the $T_{max}$ is no more than about 2 hours.

Another embodiment is a pharmaceutical composition of the present invention comprising the antitussive composition in combination with one or more excipients. In one such embodiment, the pharmaceutical composition of claim is in the form of a tablet, an ODT, a hard lozenge, an elixir, or a syrup.

In another embodiment of the antitussive composition, the composition comprises memantine and at least one absorption enhancer, and the absorption enhancer is an alkalizing agent or a permeation enhancer. In one such embodiment, the alkalizing agent is magnesium oxide, sodium hydroxide, sodium carbonate, potassium hydroxide, ammonium carbonate, sodium phosphate tribasic or sodium phosphate dibasic.

Another embodiment of the present invention is a method of treating acute cough in a patient in need thereof, comprising administering the antitussive compositions of the present invention. In one such embodiment, the antitussive composition is administered once a day. In another such embodiment, the antitussive composition is administered twice a day.

In one embodiment, the method of the present invention comprises administering a composition or dosage form of the present invention to a patient in need thereof, wherein the patient may be suffering from a cough which is a symptom of or results from one or more conditions selected from the group consisting of coughing, sneezing, rhinorrhea, nasal obstruction, nasal congestion, nasal pruritus, rhinorrhea, allergies, allergic vasomotor rhinitis (hay fever), seasonal allergic vasomotor rhinitis, perennial allergic vasomotor rhinitis, a respiratory disease, a cold, acute bronchitis, chronic bronchitis, asthmatic bronchitis, bronchiectasis, pneumonia, lung tuberculosis, silicosis, silicotuberculosis, pulmonary cancer, upper respiratory inflammation, pharyngitis, laryngitis, nasal catarrh, asthma, bronchial asthma, infantile asthma, pulmonary emphysema, pneumoconiosis, pulmonary fibrosis, pulmonary silicosis, pulmonary suppuration, pleuritis, tonsillitis, cough hives, post-viral cough, gastroesophageal reflux disease, sinusitis and whooping cough. In another embodiment, the patient may be suffering from cough resulting from one or more procedures selected from the group consisting of a bronchography and a bronchoscopy.

In other embodiments, the method of the present invention further comprises a step of diagnosing or evaluating a patient for coughing or sneezing, or one of the conditions disclosed herein in which coughing is a symptom or results from the condition.

This invention is further illustrated by the following examples that should not be construed as limiting. Those of skill in the art should, in light of the present disclosure, appreciate that many changes can be made to the specific embodiments which are disclosed and still obtain a like or similar result without departing from the spirit or scope of the invention.

Memantine Formulations

In some specific embodiments, the present formulations can be presented as follows:
a) Enterically-Coated Tablet A multilayer enterically-coated tablet comprising memantine, which is optimized to rapid small bowel release of memantine by coating with enteric polymers including acid functional cellulosics such as cellulose acetate phthalate, cellulose acetate succinate, hydroxypropylmethyl cellulose phthalate, hydroxypropylmethyl cellulose acetate succinate; non-cellulosics such as polyvinyl acetate phthalate, sodium alginate, Eudragit L or S, etc. comprising the outermost layer. Subsequent layers may have an outer layer containing pH modifiers and/or permeation enhancers. The middle layer may contain memantine and other pharmaceutically active agents. The innermost layer may contain encased urine acidification agents.

The tablet formulation may include standard excipients such as binders, disintegrants, lubricants, and glidants, and additionally include some or all of the following:
1. Buffering agents as described herein to neutralize/alkalinize the local pH in the upper small intestine to promote an increased rate of oral memantine absorption ($T_{max}$).
2. Absorption enhancers as described herein to promote an increased rate of oral memantine absorption ($T_{max}$).
3. Urinary acidification agents as described herein loaded into a carrier (enteric resin or film coated core) designed to delay the release to the lower small intestine, spacially and temporally released well after memantine absorption is completed.

A particular formulation comprises:

Outer coating: a pH dependent release polymer such as Eudragit L30 D-55, designed to dissolve in the proximal small bowel
Active: Memantine HCl (20 mg)
Binder: Microcrystalline Cellulose (160 mg)
Disintegrating Agent Crospovidone (340 mg)
Glidant: Talc (91.2 mg)
Lubricant: Magnesium Stearate (10 mg)
Absorption enhancers: Menthol (0.58 mg), polyethylene glycol 1000(1.5 mg), Oleic acid (0.72 mg), Polysorbate 80 (unlimited),
Alkalizing agents: Sodium hydroxide (6.72 mg), Calcium Carbonate (350 mg), Sodium Carbonate (25 mg), Sodium Citrate (275 mg)
Urine acidification agents: Ammonium Chloride (1000 mg), Calcium Chloride (no tablet listed), Sodium Phosphate Dibasic Anhydrous (110 mg), Potassium Phosphate, dibasic (unlimited), Ascorbic acid (28 mg), Ammonium Dihydrogen Phosphate (0.4 mg), Glutamic acid (300 mg) and Methionine (300 mg)

b) Compressed Tablet

The compressed tablets of the present invention can have the form of various ODTs known in the art (e.g., DuraSolv, CIMA Labs, Eden Prairie, Minn.; OraSolv, CIMA Labs, Eden Prairie, Minn.; WOWTAB, Yamanouchi, Norman, Okla.). These tablets can be of sufficient hardness so that they can be easily handled and can be packaged in blister packs or bottles. Alternatively, the ODT of the present invention may be prepared by lyophilization manufacturing processes (e.g., Zydis, Cardinal Health, Dublin, Ohio) to produce fragile freeze-dried tablets and compressed multiparticle tablets that can be packaged only in unit-dose blisters because of their high friability (8, 11 or 12). When such tablets are enterically-coated, the flavorants, pH modifiers and/or permeation enhancers will be released either before or simultaneous to the release of memantine and other pharmaceutically active agents, and the innermost layer consisting of encased urine acidifying agents, will be released only in the distal GI tract.

The pH of the solid dosage form is determined by dissolving the solid dosage form in artificial saliva at a concentration of 10% of the composition and determining the pH of the resulting solution or suspension (Artificial saliva formulation is disclosed in Fusayema et al., *Journal of Dental Research* 1963, 42, 1183-1197 which is incorporated herein by reference for all purposes). In a particular embodiment of the present invention, the compressed tablet is an oral fast dissolving tablet.

The processes used to manufacture orally disintegrating tablets include loose compression tabletting, a process which is not very different than the manufacturing method used for traditional tables and lyophilization processes. In loose compression, ODTs are compressed at much lower forces (4-20 kN) than traditional tablets. However, since ODTs are compressed at very low forces as ODTs need to be soft enough to disintegrate rapidly in the mouth, issues of material sticking to the die walls can be challenging. Typically, as in most tablet blends, lubricants such as magnesium stearate are added to the blend to reduce the amount of material that may stick to the die wall. Differences may be the use of disintegrating aids, such as crospovidone, and binding agents that aid in mouth feel, such as microcrystalline cellulose. Primarily, ODTs contain some form of sugar such as mannitol, which typically serves as the major diluent of the ODTs, and is also the primary contributor to the smooth and creamy mouth feel of most ODTs. Lyophilized ODT formulations that use proprietary technologies can produce a tablet that has a faster disintegration rate: the Zydis ODT typically dissolves in the mouth in less than 5 seconds without water.

ODTs are available in HPDE bottles (Parcopa) or individually sealed in blister packs to protect the tablets from damage, moisture, and oxidation. Because ODTs are soft in nature, the ability to successfully package an ODT in a bottle is difficult. However, CIMA Labs markets their Durasolv ODT as being able to be placed into bottle for commercial sale, while CIMA's Orasolv is marketed for blisters only. Zydis ODT tablets manufactured by Catalent Pharma Solutions are delivered in a blisterpack. The differences between the two CIMA products are proprietary; however, the primary difference is expected to be the use of microcrystalline cellulose (MCC), such as Avicel PH101, in the Durasolv product. MCC serves multiple purposes in an ODT but in the case of CIMA's products, it acts as a binder, increasing the internal strength of the tablet and making it more robust for packaging in bottles.

Examples of fast dissolve ODT formulations of memantine of the present invention include excipients such as binders, disintegrants, lubricants, glidants, flavorants, sweeteners and colorants, as well as some or all of the following additional ingredients:

Active: Memantine HCl (20 mg)
Lubricant: (Magnesium Stearate 10 mg)
Disintegrant: Crospovidone (180 mg)
Glidant: Talc (36 mg)
Binding Agent: Microcrystalline Cellulose (415.92 mg)
Sweeteners: Aspartame (36 mg), Dextrose (115.7 mg)
Colorants: D&C Red 27 Aluminum Lake (1.25 mg), FD&C Blue 1 Aluminum Lake (0.18 mg)
Absorption enhancers: Menthol, natural (10.0 mg), Polysorbate 80 (2.25 mg),
Alkalizing agents: Calcium Carbonate (145.5 mg), Sodium hydroxide (0.15 mg), Sodium Carbonate (30 mg), Sodium Citrate (300 mg)
Urine acidification agents: Ammonium Chloride (1000 mg), Sodium Phosphate Dibasic Anhydrous (110 mg), Potassium Phosphate, dibasic (17 mg), Ascorbic acid (no fast melts listed), Ammonium Dihydrogen Phosphate (0.2 mg), Glutamic acid (300 mg) and Methionine (300 mg)

c) Hard Lozenge or Buccal Tablet

Lozenge compositions of the present invention include lozenge excipients such as lubricants, glidants, binders, flavorants, sweeteners and colorants. A particular hard lozenge formulation comprises:

Glidant: Talc (15 mg)
Binder: Microcrystalline Cellulose (43.2 mg)
Colorants: Colorants: D&C Red 27 Aluminum Lake (1.25 mg), FD&C Blue 1 Aluminum Lake (0.18 mg)
Lubricant: Magnesium Stearate (15 mg)
Sweeteners: Saccharin (0.20 mg)
Sodium Carbonate (30 mg), Sodium Citrate (300 mg)

d) Hard Lozenge or Buccal Tablet

The hard lozenge or buccal tablet may also include one or more buffering agents, one or more absorption enhancers, and/or one or more urine acidification agents. The lozenge compositions of the present invention may include lozenge excipients such as lubricants, glidants, binders, flavorants, sweeteners and colorants. Unique to such compositions of the present invention, however, are the following ingredients:

1. Buffering agents to neutralize/alkalinize the local pH in the upper small intestine to promote an increased rate of oral memantine absorption (Tmax).
2. Absorption enhancers as described herein to promote an increased rate of oral memantine absorption ($T_{max}$).
3. Urine Acidification agents loaded into a carrier (ion exchange resin or film coated core) as described herein designed to delay the release to the lower small intestine, spacially and temporally released well after memantine absorption is completed.

A particular hard lozenge formulation comprises:
Glidant: Talc (15 mg)
Binder: Microcrystalline Cellulose (43.2 mg)
Colorants: Colorants: D&C Red 27 Aluminum Lake (1.25 mg), FD&C Blue 1 Aluminum Lake (0.18 mg)
Lubricant: Magnesium Stearate (15 mg)
Sweeteners: Saccharin (0.20 mg)
Absorption enhancers: Menthol, natural (14.0 mg), Polysorbate 80 (2.25 mg),
Alkalizing agents: Calcium Carbonate (145.5 mg), Sodium hydroxide (0.15 mg), Sodium Carbonate (30 mg), Sodium Citrate (300 mg)
Urine acidification agents: Ammonium Chloride (8 mg), Sodium Phosphate Dibasic Anhydrous (110 mg), Potassium Phosphate, dibasic (17 mg), Ascorbic acid, Ammonium Dihydrogen Phosphate (0.2 mg), Glutamic acid (300 mg) and Methionine (300 mg)

Various embodiments of hard lozenge compositions comprise:
Lozenge base: 95-99 wt %
Memantine HCl: 0.2-1.5 wt %
Artificial sweetener(s): 0.15-0.75 wt %
Colorant(s): 0.1-0.75 wt %
Flavor(s): 0.1-0.75 wt %
Menthol: 0-0.2 wt %
Alkalizing agent: 0-1.5 wt %
or
Lozenge base: about 97 wt %
Memantine HCl: about 0.3 wt %
Artificial sweetener(s): about 0.4 wt %
Colorant: about 0.4 wt %
Flavor(s): about 0.4 wt %
Permeation enhancer: about 0.2 wt %
Alkalizing agent(s): about 1.3 wt %
or
Lozenge base: about 96 wt %
Memantine HCl: about 1 wt %
Artificial sweetener(s): about 0.4 wt %
Colorant: about 0.4 wt %
Flavor(s): about 0.4 wt %
Permeation enhancer: about 0.2 wt %
Alkalizing agent(s): about 1.3 wt %
or
Lozenge base: about 97 wt %
Memantine HCl: about 0.04 wt %
Artificial sweetener(s): about 0.4 wt %
Colorant: about 0.4 wt %
Flavor(s): about 0.4 wt %
Permeation enhancer: about 0.2 wt %
Alkalizing agent(s): about 1.3 wt %
or
Lozenge base: about 60-85 wt %
Memantine HCl: about 0.15-0.8 wt %
Artificial sweetener(s): about 0.1-1 wt %
Colorant: about 0.05-1 wt %
Flavor(s): about 0.05-1 wt %
Permeation enhancer: about 0-0.15 wt %
Alkalizing agent(s): about 0-1 wt %
Urine acidification agent: about 10-30 wt %
Taste-masking coating (urine acidification agent): about 1-10 wt %
or
Lozenge base: about 82 wt %
Memantine HCl: about 0.2 wt %
Artificial sweetener(s): about 0.15 wt %
Colorant: about 0.05 wt %
Flavor(s): about 0.05 wt %
Permeation enhancer: about 0.125 wt %
Alkalizing agent(s): about 0.9 wt %
Urine acidification agent: about 15 wt %
Taste-masking coating (urine acidification agent): abou 1.6 wt %
or
Lozenge base: about 72 wt %
Memantine HCl: about 0.75 wt %
Artificial sweetener(s): about 0.3 wt %
Colorant: about 0.3 wt %
Flavor(s): about 0.3 wt %
Permeation enhancer: about 0.125 wt %
Alkalizing agent(s): about 0.9 wt %
Urine acidification agent: about 20 wt %
Taste-masking coating (urine acidification agent): about 5 wt %
or
Lozenge base: about 82 wt %
Memantine HCl: about 0.2 wt %
Artificial sweetener(s): about 0.15 wt %
Colorant: about 0.05 wt %
Flavor(s): about 0.05 wt %
Permeation enhancer: about 0.125 wt %
Alkalizing agent(s): about 0.9 wt %
Urine acidification agent: about 15 wt %
Taste-masking coating (urine acidification agent): abou 1.6 wt %

The total weight of the lozenges of the present invention, as embodied above, ranges from about 3 to about 4 grams/lozenge. In a particular embodiment, the lozenge weighs about 2.8 grams. In another particular embodiment, the lozenge weighs about 4 grams. In still another particular embodiment, the permeation enhancer comprises menthol. In other particular embodiments, the lozenge base is isomalt. In still other particular embodiments, the artificial sweetener is acesulfame potassium. In still other particular embodiments, the urine acidification agent is ammonium chloride. In still other particular embodiments, the alkalizing agents are sodium carbonate and/or sodium hydroxide.

e) Oral Liquid Formulation

Elixir formulations of the present invention of the present invention include conventional elixir excipients such as alcohol diluents, thickening agents, flavorants, sweeteners and preservatives. Unique to such compositions of the present invention, however, are the following ingredients:

1. Buffering agents to neutralize/alkalinize the local pH in the upper small intestine to promote an increased rate of oral memantine absorption ($T_{max}$).

2. Absorption enhancers to promote an increased rate of oral memantine absorption ($T_{max}$).
3. Urine Acidification agents loaded into a carrier (ion exchange resin or film coated core) designed to delay the release to the lower small intestine, spacially and temporally released well after memantine absorption is completed.

A particular elixir formulation of the present invention comprises:

Active: Memantine HCl (20 mg/10 mL)
Diluent: Propylene Glycol (89.02%)
Thickening Agents Carboxymethycellulose (6.04%), Microcrystalline Cellulose/Sodium CMC (11.25%), Glycerine (50% mg)
Flavorants: Eucalyptus Oil (0.07%), Flavorants (0.05%), Sweeteners: Sucrose (72%), Sodium Saccharin (2.25%)
Preservatives: Methylparaben (1.0%), Propylparaben (0.3%)
Coloring Agents: FD&C Red #40 (0.01%)
Water (q.s)
Absorption enhancers: Menthol (0.07%/Polysorbate 80 (12.5%)
Alkalizing agents, Calcium Carbonate (265.2 mg), Sodium hydroxide 40%), Sodium Carbonate (6.5 mg), Potassium metaphosphate, Sodium acetate (0.72%,) Sodium Citrate (0.05%)
Urine acidification agents: Ammonium Chloride (12.5%), Calcium Chloride (0.05%), Sodium Phosphate Dibasic Anhydrous (0.45% or 110 mg), Ascorbic acid, Ammonium Dihydrogen Phosphate, Glutamic acid, and methionine.

In all five formulations described above, combinations with other active agents acceptable for use in cough medications can also be included, in addition to memantine alone. These active agents can be added to the memantine either individually, sequentially, in aggregate or in combinations thereof. These agents include decongestants, mucolytics and expectorants, antipyretics/analgesics and other antitussives. Decongestants include antihistamines (e.g., diphenhydramine, chlorphenhydramine, and $2^{nd}$ and $3^{rd}$ generation antihistamines) and their delayed release forms, and adrenergic agents (such as pseudoephedrine and neosynephrine) and their delayed release forms. Mucolytics and expectorants include guaifenesin and acetyl cysteine and their delayed release forms. Antipyretics and analgesics include acetaminophen, phenacetin, and mixed Cox-1 and Cox-2 inhibitors such as ibuprofen. Other antitussive agents include menthol, dextromethorphan, diphenhydramine and chlorphenhydramine, codeine and ambroxol.

Unless defined otherwise, all technical and scientific terms herein have the same meaning as commonly understood by one of ordinary skill in the art to which this invention belongs. Any methods and materials, similar or equivalent to those described herein, can be used in the practice or testing of the present invention.

In Vivo Experiments

EXAMPLE 1

Antitussive effects of memantine in Guinea Pigs
Animals

Male Hartley guinea pigs (200-700 g) were studied and all experiments were first approved by the institutional Animal Care and Use Committee.

Citric Acid Induced Cough

Animals were placed in a transparent chamber (Buxco Research Systems, Wilmington, N.C.) with a continuous flow of air and exposed to increasing concentrations of citric acid (0.01 M-0.3 M) is delivered by an ultrasonic nebulizer generating aerosol particles of 3-6 μm diameter. Coughs were counted during a 5 minute nebulization period and over the subsequent 5 minutes with the assistance of sound and pressure monitoring from the chamber. Respiratory rate and tidal volume were monitored throughout via a calibrated pressure transducer (Emka Technologies, Falls Church, Va.).

Bradykinin Induced Cough

Using a similar chamber and nebulizer system, animals were treated first with aerosolized peptidase inhibitors (captopril 0.1 μM and thiorphan 0.1 μM, 5 minutes nebulization) to reduce bradykinin degradation and enhance tussive responses evoked by bradykinin (unpublished observations). Animals were then exposed to increasing concentrations of aerosolized bradykinin (0.1-3 mg/mL), again for 5 minute periods. Coughs are counted during this and the subsequent 5 minutes. Pressure changes within the chamber are used to monitor respiratory rate (Biopac Systems Inc, Goleta, Calif.).

Compounds and Materials

Memantine, citric acid, bradykinin, captopril, and thiorphan were obtained from Sigma-Aldrich (St. Louis, Mo.), dextromethorphan from MP Biomedicals (Solon, Ohio), and ketamine from Vedco Inc (St Joseph, Mo.). All drugs were dissolved in 0.9% saline except citric acid (dissolved in distilled water) and thiorphan (dissolved in ethanol and then diluted in 0.9% saline.

Statistical Analysis

Data were analyzed using SPSS (version 15, SPSS Inc, Chicago, Ill.) and graphs produced using Prism (version 4, Graphpad Ltd). A 5% level of significance was used throughout. Cumulative numbers of coughs to citric acid/bradykinin were expressed as median and inter-quartile ranges as the data was positively skewed. Comparisons of cumulative cough numbers for treatment groups was therefore compared using non-parametric tests (Kruskal Wallis and Mann-Whitney U tests).

Results

Citric Acid Induced Cough

Figure 2:
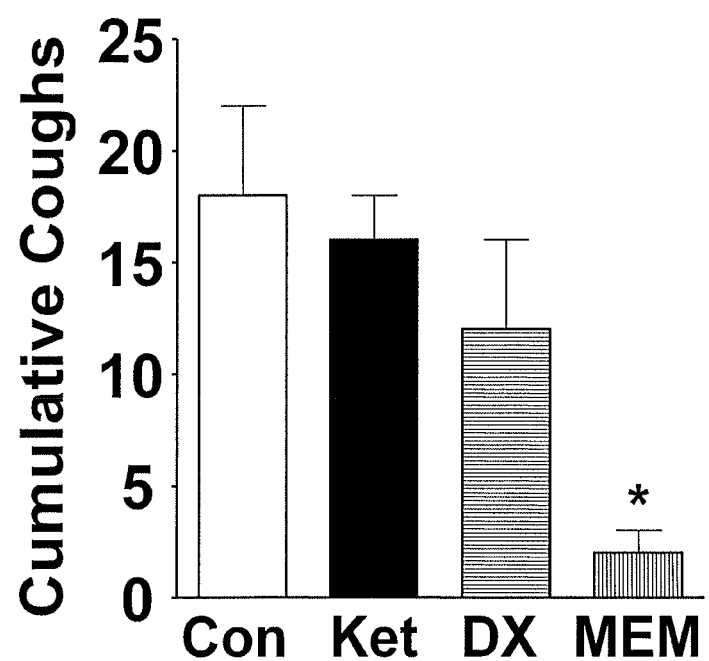
FIG. 2: Cumulative number of coughs (presented as mean±sem) evoked by citric acid aerosols (0.01-0.3M) in control (Con) animals and animals treated with ketamine (Ket), dextromethorphan (DX) or memantine (MEM). Each drug was administered intraperitoneally at a dose of 30 mg/kg. Unlike ketamine or dextromethorphan, memantine reduced the cumulative number of coughs evoked by citric acid ($p<0.02$).
Figure 3:
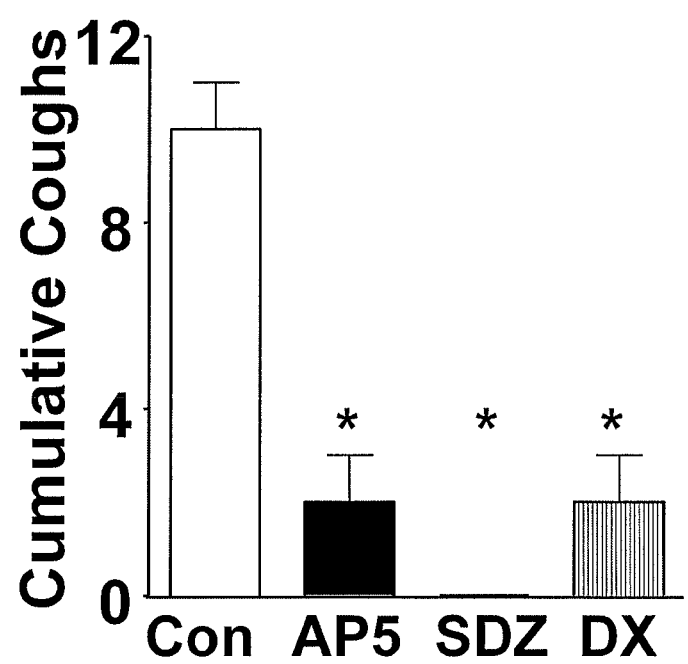
FIG. 3: Microinjection of the NMDA receptor antagonists AP5, SDZ220581, and dextromethorphan (DX) into the central termination sites of the cough receptors prevents citric acid evoked coughing in anesthetized guinea pigs.
Figure 4:
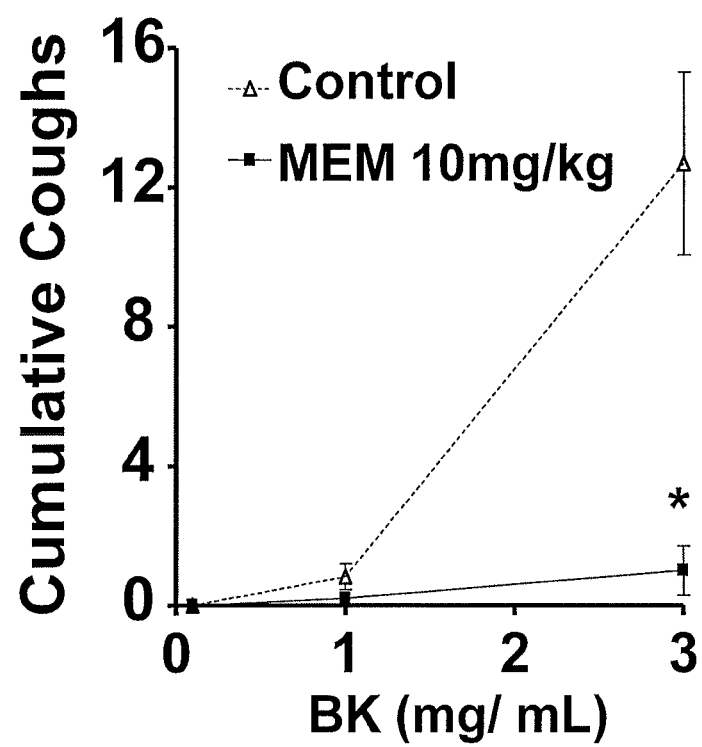
FIG. 4: Cumulative number of coughs (median, IQR) in response to bradykinin aerosols in control and memantine (MEM) treated animals. Compared to control, memantine significantly reduced the number of coughs evoked by bradykinin (*, $p<0.01$).
Figure 5:
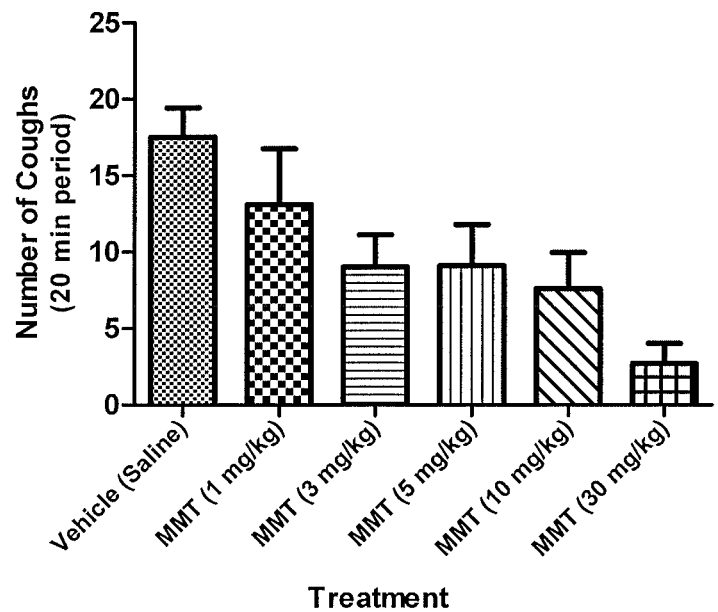
FIG. 5: Effect of different doses of memantine administered orally to guinea pigs on reduction of citric acid-induced cough

In contrast to 10 or 30 mg/kg memantine, dextromethorphan (30 mg/kg; n=8) and ketamine (30 mg/kg; n=8) failed to produce a statistically significant reduction in cumulative coughs evoked by 0.01-0.3 M citric acid (p=0.328 and p=0.645, respectively) (FIG. 2 and Table 5). Dextromethorphan but not ketamine significantly reduced the cumulative number of coughs evoked by lower concentrations of citric acid (0.01-0.1 M) (p=0.038). Mild to moderate sedation is observed in 62.5% of the dextromethorphan-treated animals and 87.5% of the ketamine treated animals. When administered at 30 mg/kg, the sedation produced by dextromethorphan was long-lasting (>2 hours) and persisted throughout the citric acid challenge while ketamine-induced sedation rapidly reversed during the cough challenge (40-50 minutes post-injection).

The 50 mg/kg doses of ketamine and dextromethorphan caused severe sedation, precluding assessment of cough responsiveness even though breathing frequency declined only slightly and insignificantly [controls mean breathing frequency 117.7(±26.3) breaths/min versus ketamine 92.3 (±18.8) breaths/min (p=0.25) and dextromethorphan 90.0(±13.7) breaths/min (p=0.18)] with no significant change in tidal volume (p=0.293) or expiratory time (p=0.14).

Compared with vehicle, 10 mg/kg memantine markedly reduced the number of cumulative coughs evoked by 0.01-0.3 M citric acid (p=0.012) (FIG. 1 and Table 1). At 1 and 3 mg/kg, there is no significant effect of memantine over vehicle. The time to the first cough during the citric acid challenge is shorter for vehicle than memantine 10 mg/kg (p=0.007). No side effects associated with the 10 mg/kg memantine treatment are apparent. As expected, tripling the dose of memantine administered to 30 mg/kg similarly reduced cough responses but produced slight behavioral changes.

TABLE 5

Cumulative numbers of cough with increasing concentrations of citric acid for treatment groups and contemporaneous controls, *indicates a significant difference in cough from controls. Results are presented as a median (intraquartile (25-75) range)

| | | Citric Acid Concentration | | |
|---|---|---|---|---|
| | | 0.01M | 0.1M | 0.3M |
| Controls (n = 20) | | 0.0 (0.0-1.0) | 3.0 (0.5-23.0) | 24.0 (13.0-25.5) |
| Memantine (n = 8) | 1 mg/kg | 0.0 (0.0-1.0) | 5.0 (1.0-20.0) | 14.0 |
| Memantine (n = 8) | 3 mg/kg | 0.0 (0.0-0.0) | 3.0 (1.0-7.0) | 24.5 (18.3-27.3) |
| Memantine (n = 6) | 10 mg/kg | 0.0 (0.0-0.0) | 0.0 (0.0-1.8) | 1.5* (0.3-10.3) |
| Controls (n = 8) | | 0.0 (0.0-0.0) | 16.0 (3.5-26.0) | 19.5 (7.5-26.0) |
| Dextromethorphan (n = 8) | 30 mg/kg | 0.0 (0.0-0.0) | 0.5* (0.0-1.5) | 7.5 (2.5-23.5) |
| Ketamine (n = 8) | 30 mg/kg | 0.0 (0.0-0.0) | 1.5 (0.0-6.3) | 11.0 (11.0-21.0) |
| Memantine (n = 6) | 30 mg/kg | 0.0 (0.0-0.0) | 0.0* (0.0-0.0) | 1.5* (0.0-5.5) |
| Controls (n = 7) | | 0.0 (0.0-1.0) | 14.0 (1.0-23.0) | 24.0 (13.5-25.0) |

Bradykinin Induced Cough

Figure 6:
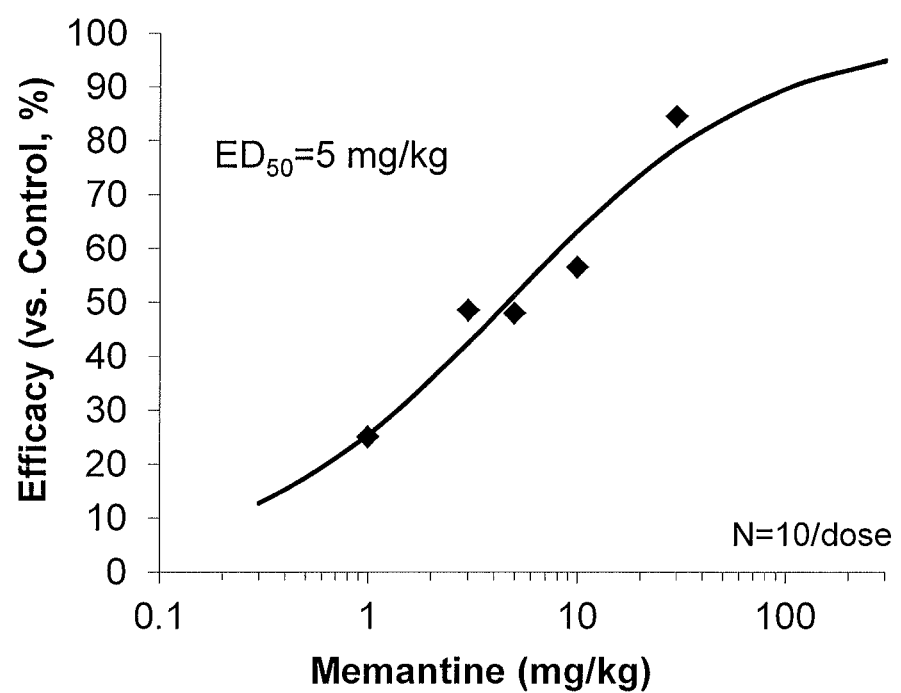
FIG. 6: Dose response—Efficacy of oral administration of memantine relative to vehicle control on citric acid-induced cough in guinea pigs.

Compared to vehicle, memantine (10 mg/kg) substantially reduced the cumulative number of coughs evoked by 0.1-3 mg/mL bradykinin, [memantine median 0.0 coughs (IQRO-0.8) versus controls 16 coughs (IQR9.5—18.5), p=0.002; see FIG. 6].

Respiratory Parameters

None of the treatments studied altered breathing frequency or expiratory times during citric acid challenge. Tidal volume is significantly increased with increasing citric acid concentration in all treatment groups. Bradykinin induced a small reduction in breathing frequency in control animals but a small increase in breathing frequency following 10 mg/kg memantine treatment (p=0.012).

EXAMPLE 2

Pharmacokinetic Evaluation of Memantine After Buccal Administration in Male Beagle Dogs The pharmacokinetics of memantine were evaluated after buccal administration in male beagle dogs. Memantine was formulated in water, 3.3 mg/mL sodium hydroxide in water, or 7.5 mg/mL sodium carbonate in water. All dogs received a 0.4 mg/kg dose of memantine. Plasma levels of memantine were determined by LC-MS/MS. Pharmacokinetic parameters were determined for the memantine plasma data.

For dosing, dogs were anesthetized with an IV injection of ketamine/diazepam, and maintained by isoflurane intubation during the buccal administration. The dosing solution was pipetted into a circular cylinder to concentrate the dosing solution on one area of the mucosa. At just prior to the 15 minute sample time point, the oral cavity was rinsed with 5 mL of water and dried with gauze Immediately after the rinse, the 15 minute sample was collected.

Table 6 provides a summary of pharmacokinetic findings, comparing oral and buccal dosing routes for memantine compositions containing a urinary acidification agent (oral route) or a buffering agent (buccal route) to increase local pH. As shown in Table 6, urinary acidification increases the rate of elimination as shown by the reduced $T_{1/2}$ values relative to controls, and buccal administration increases the rate of absorption (as shown by decreased $T_{max}$ and increased $C_{max}$ values), particularly when alkalizing agents are used to increase the local pH of the buccal environment.

TABLE 6

Summary of PK Findings

| MMT | | | | | | | |
|---|---|---|---|---|---|---|---|
| Dose | 0.4 mg/kg | 0.4 mg/kg | 0.4 mg/kg | 0.4 mg/kg | 0.4 mg/kg | 0.4 mg/kg | 0.4 mg/kg |
| Route | Oral | Oral | Oral | Oral | Buccal | Buccal | Buccal |
| Objective | | ↓ Urine pH | ↓ Urine pH | ↓ Urine pH | | ↑ Buccal pH | ↑ Buccal pH |
| Concomitant agent | Control$_{Ave}$ | 15 mg/kg NH$_4$Cl[2] | 25 mg/kg NH$_4$Cl | 30 mg/kg NH$_4$Cl | Control | 3.3 mg/ml NaOH | 7.5 mg/ml Na$_2$CO$_3$ |
| $C_{max}$ (ng/mL) | 22 | 25 | 20 | 25 | 23 | 52 | 54 |
| $C_{max}$/Dose | 5.2 | 6.8 | 5.2 | 5.4 | 6.7 | 12.9 | |
| $T_{max}$ (h) | 1.7 | 2.0 | 1.5 | 1.1 | 0.75 | 0.25 P < 0.05 vs. C | 0.45 |
| AUC$_{0-t}$ (ng · h/mL) | 190 | 233 | 169 | 163 | 119 | 108 | 179 |
| AUC$_{0-\infty}$ (ng · h/mL) | 210 | 256 | 179 | 168 | 125 | 112 | 184 |
| $T_{1/2}$ (h) | 6.5 | 6.7 | 5.5 | 4.8 P < 0.05 vs. C | 5.2 | 5.2 | 4.5 |

EXAMPLE 3

Pharmacokinetic Evaluation of Memantine After Buccal Administration in Male Beagle Dogs The pharmacokinetics of memantine were evaluated after buccal administration in male beagle dogs using procedures similar to those used in Example 2, except that menthol or menthol and ammonium chloride where co-administered with the sodium hydroxide (Table 7). Table 7 provides a summary of pharmacokinetic findings, comparing memantine compositions containing an alkalinizing agent to increase local pH and a permeation enhancer (menthol), and optionally a urinary acidifying agent. As shown in Table 7, the combination of an alkalinizing agent and permeation enhancer, and substantially increases the $C_{max}$/Dose and substantially decreases $T_{max}$, and significantly reduces $T_{1/2}$ compared to the control. Further addition of a urinary acidifying agent (e.g., NH$_4$Cl) further reduces $T_{1/2}$, indicating more rapid elimination of memantine.

TABLE 7

Summary of PK Findings

| | MMT Dose | | | |
|---|---|---|---|---|
| | 0.4 mg/kg | 0.4 mg/kg | 0.4 mg/kg | 0.4 mg/kg |
| Route | Oral | Oral | Oral | Oral |
| Objective | | ↑ Buccal pH | ↑ Buccal pH ↓ Urine pH | ↑ Buccal pH ↓ Urine pH |
| Concomitant agent | Control | 3.3 mg/ml sodium hydroxide + 5 mg/ml menthol | 3.3 mg/ml sodium hydroxide + 5 mg/ml menthol + 30 mg/kg NH$_4$Cl | 3.3 mg/ml sodium hydroxide + 5 mg/ml menthol + 20 mg/kg NH$_4$Cl |
| $C_{max}$ (ng/mL) | 34.5 | 77.0 | 43.0 | 126 |
| $C_{max}$/Dose | 7.91 | 18.16 | 9.18 | 26.03 |
| $T_{max}$ (h) | 0.75 | 0.20 P < 0.05 vs. C | 0.25 P < 0.05 vs. C | 0.15 P < 0.05 vs. C |
| AUC$_{0-t}$ (ng · h/mL) | 120 | 113 | 103 | 134 |
| AUC$_{0-\infty}$ (ng · h/mL) | 132 | 126 | 125 | 143 |
| $T_{1/2}$ (h) | 7.18 | 5.05 P < 0.05 vs. C | 4.33 P < 0.05 vs. C | 4.60 P < 0.05 vs. C |

EXAMPLE 4

Orally vs. Parenterally Administered Memantine

Figure 7:
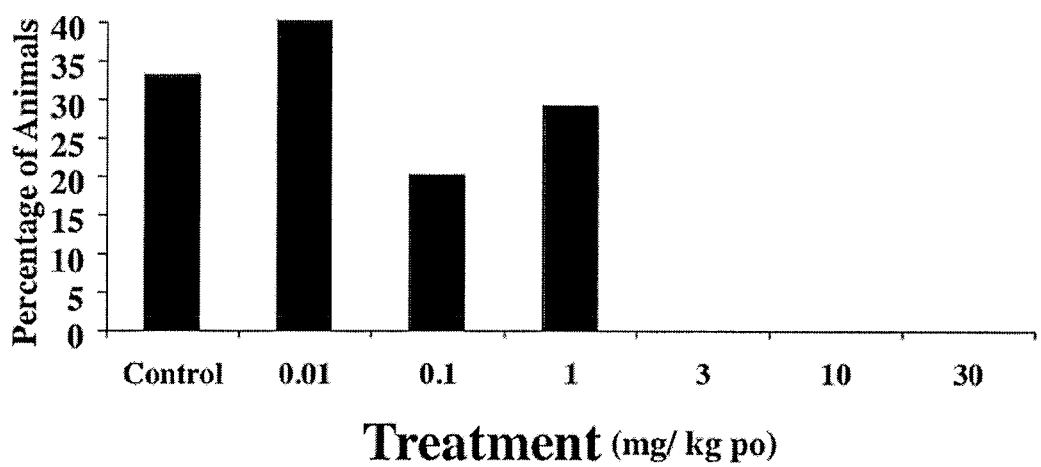
FIG. 7: Effect of memantine on citric acid evoked cough: Percentage of animals coughing $\geq 15$ times.
Figure 8:
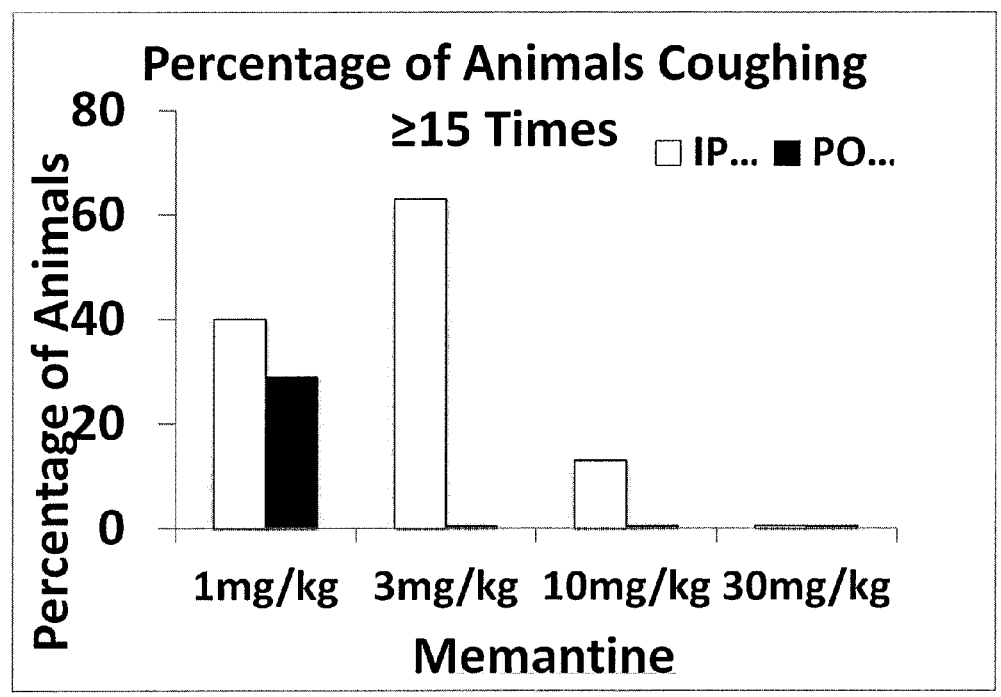
FIG. 8: Comparison of oral (PO) and parenteral (IP) administration of memantine at 1 mg/kg, 3 mg/kg, 10 mg/kg and 30 mg/kg doses.
Figure 9:
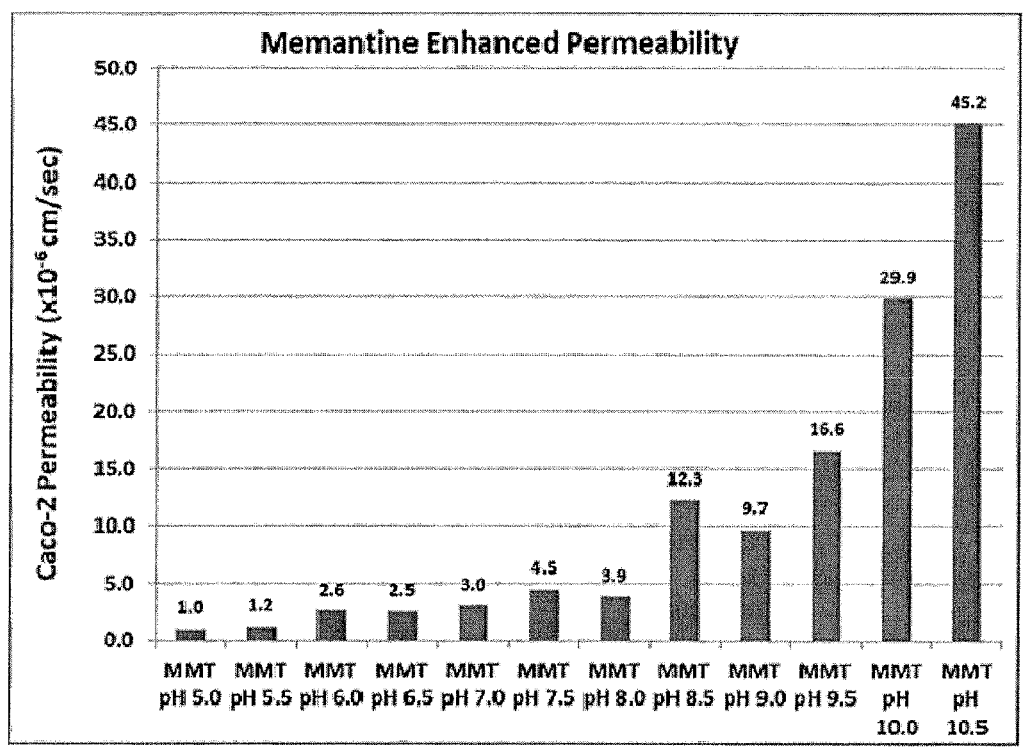
FIG. 9: Memantine-pH dependent in vitro intestinal permeability (Caco-2 cells).

The effects of orally administered versus parenterally administered memantine on citric acid evoked cough in guinea pigs is shown in FIGS. 7 and 8. FIG. 7 shows that orally administered memantine reduces cough relative to controls (measured as the percentage of animals coughing >15 times) at doses around 0.1-1 mg/kg. Surprisingly, at doses of 1 mg/kg or more, orally administered memantine consistently provided substantially reduced levels of cough compared to parenterally administered memantine (FIG. 8; except at very high doses, around 30 mg/kg, where oral and parenteral administration gave comparable reductions in levels of cough).

EXAMPLE 5

Enhancement and/or the Reduction of Decongestant-Induced Impairment of Cognition by Memantine The effects of memantine on enhancing cognition were investigated with fear conditioning tests on mice. Specifically, the fear conditioning test exposed mice to a conditioned stimulus (a tone) and an unconditioned stimulus (a mild electric shock). The mice learned to associate the tone with the shock as reflected by freezing. After being adequately conditioned, the mice were administered memantine or a control (vehicle alone). Memantine was followed with the administration of diphenhydramine; the control was followed with the administration of saline or diphenhydramine. Diphenhydramine induces anxiety in mice. Accordingly, this test studied the effect of memantine on enhancing cognition compared to diphenhydramine alone or vehicle alone.

Fear Conditioning: Fear conditioning mouse chambers (7"W×7"D×12"H; Coulbourne Instruments, Lehigh Valley, Pa.) were housed in sound attenuating chambers. A camera was mounted on the ceiling of the chamber to capture mouse behavior (FreezeFrame software, Coulbourne Instruments, Lehigh Valley, Pa.); data were analyzed by Freezeview software (Coulbourne Instruments, Lehigh Valley, Pa.). Fear conditioning chambers were calibrated prior to each experiment to ensure that each chamber delivers the same shock intensity. The experimental chambers were thoroughly cleaned with 70% ethanol, dried, and ventilated for a few minutes between subjects. Pavlovian fear conditioning refers to the learning of associations between a negative reinforcer (e.g., a mild electric foot shock/s), a novel context (e.g. a context) and/or a specific, neutral, cue (e.g., tone or white noise). To assess contextual and cued (tone) learning and memory, a standardized fear conditioning task developed for the evaluation of memory in rodents was used.

Protocol: Rodents were acclimated to the testing chamber for 2 min Following acclimation, rodents received 3 pairings of white noise (conditioned stimulus, 'CS': 10 seconds (sec) of 65 dB) and a mild foot-shock (unconditioned stimulus, US, 0.6 mA shock for 2 sec) co-terminating with the CS. After the final shock, mice were left in the chambers for 30 sec and then placed back into the home cage Immediately after training, mice were administered vehicle or memantine (10 or 20 mg/kg, IP). Thirty minutes after training, mice were treated with vehicle (saline) or diphenhydramine (20 mg/kg, IP).

Contextual Conditioning Testing: Contextual memory was tested 24 hours after training Mice were placed into the same training chamber as the day before for a test period of 8 minutes. There was no presentation of the conditioned stimulus (CS) during this test session.

Cue-induced Conditioning Testing: Mice were tested for cued memory 48 hours after training. The cued conditioning test was conducted in an altered context (i.e., a different test chamber). Cued testing at 48 hours post-training consisted of placing rodents in a novel context for 4 minutes, split into three phases: 1 min prior to presentation of the conditioned stimulus ('Pre-CS' phase); 2 minutes of presenting the conditioned stimulus ('CS' phase); 1 min after presentation of the conditioned stimulus (Post-CS' phase).

Statistical Analysis: Data are represented as the mean and standard error to the mean. Data were analyzed by analysis of variance (ANOVA) followed by Fisher PLSD, or unpaired t-tests, when appropriate to test a planned comparison. An effect was considered significant if p<0.05. Statistical outliers that fell above or below two standard deviations from the mean were removed from the final analysis.

Cue-induced Fear Conditioning: The cue-induced fear conditioning is demonstrated in FIG. 14.

Pre-CS Phase (prior to presentation of the conditioned stimulus): ANOVA revealed no effects of Treatment on pre-CS freezing.

CS Phase (Presentation of the conditioned stimulus): Diphenhydramine exhibited a strong trend toward decreased cue-induced fear conditioning compared to vehicle-vehicle controls (p=0.061) using an unpaired t-test. Further, unpaired t-test indicated that memantine (10 mg/kg, but not 20 mg/kg), co-administered with 20 mg/kg diphenhydramine significantly increased cue-induced fear conditioning compared to mice treated with vehicle-diphenhydramine 20 mg/kg alone.

Post-CS Phase (after presentation of the conditioned stimulus): There was a strong trend (p=0.052) toward a significant increase in post-CS freezing in mice treated with memantine (20 mg/kg) plus diphenhydramine versus vehicle-diphenhydramine alone.

Figure 14:
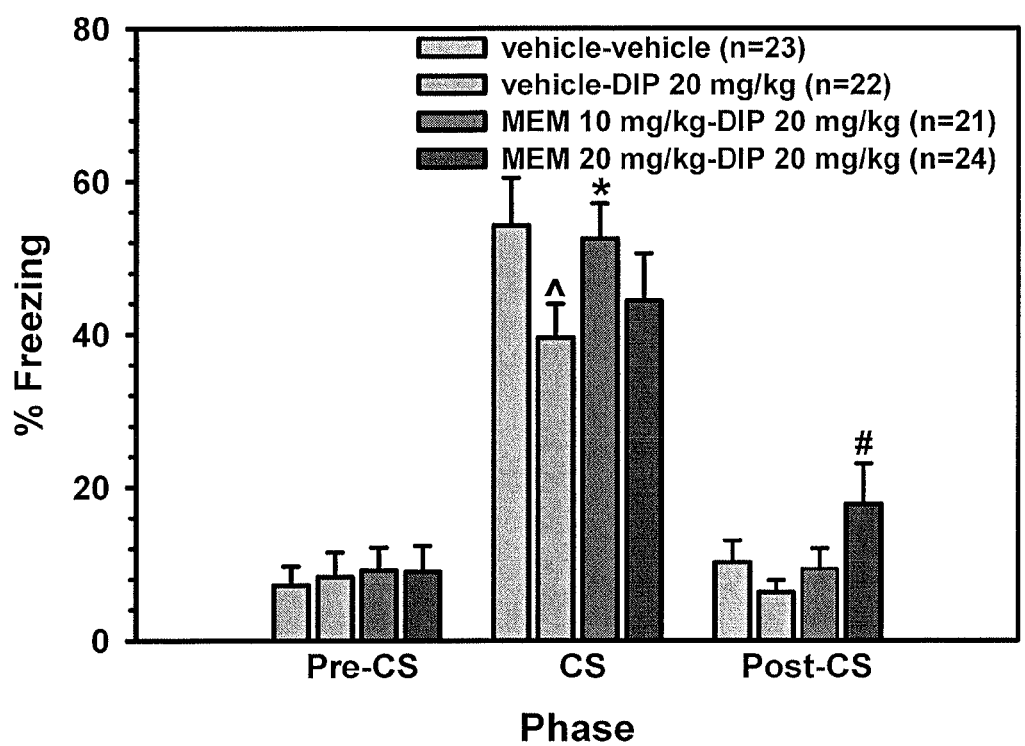
FIG. 14: The effects of diphenhydramine and memantine on freezing behavior during cued fear conditioning. Different phases of the test session are marked as 'pre-CS': before presentation of the conditioned stimulus ('cue'); 'CS: presentation of the cue; post-CS': after presentation of the cue. Data are presented as mean±SEM. Carat sign indicates a strong trend toward a significant difference compared to vehicle-vehicle ($p=0.061$). Asterisk (*$p<0.05$) indicates a significant difference compared to vehicle-DIP 20 mg/kg. Pound sign (#$p=0.052$) indicates a strong trend toward a significant difference compared to vehicle-DIP 20 mg/kg.

FIG. 14 demonstrates the effects of diphenhydramine and memantine on freezing behavior during cued fear conditioning. Specifically, FIG. 14 indicates that: 1) during the conditioned stimulus, there was a significant decrease in freezing when diphenhydramine was administered relative to the control; 2) during the conditioned stimulus, freezing was increased when memantine was administered (as opposed to just vehicle-diphenhydramine); and 3) after the conditioned stimulus, freezing was increased when memantine was administered (as opposed to just vehicle-diphenhydramine). This data thus indicates that the addition of memantine reverses the induced cognitive impairment due to the administration of diphenhydramine.

EXAMPLE 6

Synergistic Effects on Cough for Memantine Combinations with Guaifenesin, Diphenhydramine, Ambroxol, or Benzonatate in Guinea Pigs Evaluations of the synergistic effects of memantine combinations with guaifenesin, diphenhydramine, ambroxol and benzonatate, where carried out in comparison to the concentration dependent effects of each of guaifenesin, diphenhydramine, ambroxol or benzonatate on citric acid induced coughing. Each of these drugs was administered orally in half-log increments (e.g. 3 mg/kg, 10 mg/kg, 30 mg/kg) in an unpaired experimental design (each animal received only 1 dose of drug). The drugs were administered 60 minutes prior to citric acid challenge, which consisted of 5 minute challenges with aerosols of increasing concentrations of citric acid (0.01-0.3M), with 5 minute intervals in between escalating doses of the tussive stimulus. From these experiments, the highest dose of each drug that failed to inhibit coughing (i.e., subtherapeutic doses) was determined. If no inhibitory effects of the drug were apparent, dosing was set at 100 mg/kg.

The effects of the highest dose of memantine that failed to inhibit cough in these experiments (3 mg/kg) was then evaluated. with and without coincident pretreatment with 100 mg/kg guaifenesin, 10 mg/kg diphenhydramine, 30 mg/kg benzonatate or 100 mg/kg ambroxol, all of which on their own also failed to inhibit cough. The results of these experiments are presented as the mean±sem number of cumulative coughs evoked by citric acid (0.01-0.3M) in vehicle treated animals (control), memantine pretreated, combination drug pretreated (ambroxol, benzonatate, diphenhydramine or guaifenesin), or their combination with memantine.

The results of these studies are shown in FIGS. 15-18. In each case, combinations of memantine and diphenhydramine, guaifenesin, benzonatate, or ambroxol (each at the highest dose that individually failed to inhibit cough) showed significant reduction in cumulative coughs, indicating that the combination of memantine with any one of diphenhydramine, guaifenesin, benzonatate, or ambroxol are synergistic in their antitussive affect.

EXAMPLE 7

Non-Sedating Effects of Memantine

Figure 19:
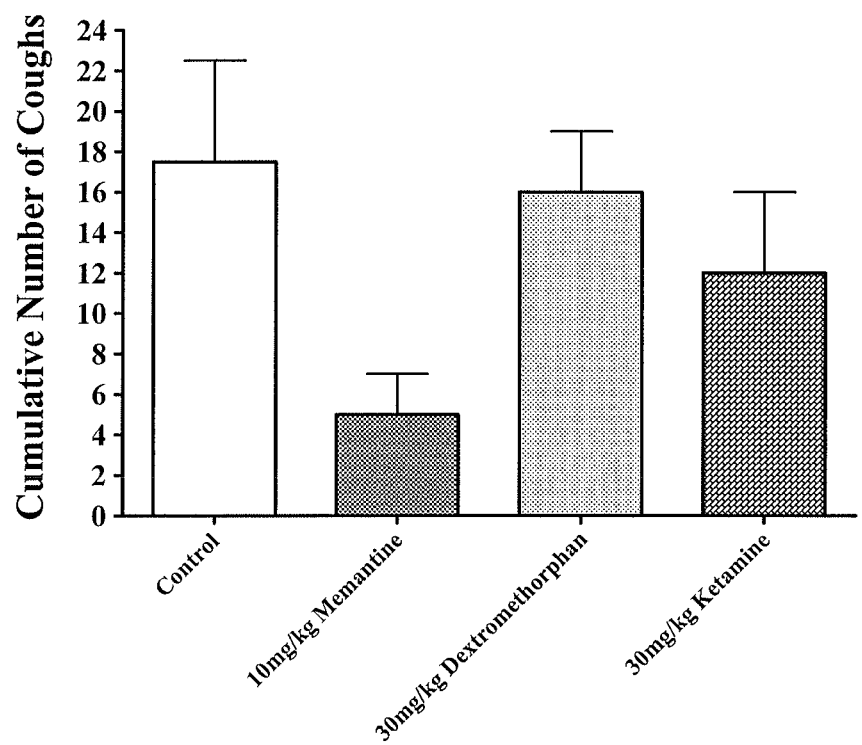
FIG. 19: Cumulative number of coughs evoked by citric acid (0.01-0.3M) in control animals and in animals pretreated intraperitoneally with 10 mg/kg memantine, 30 mg/kg dextromethorphan or 30 mg/kg ketamine. Compared to controls, 10 mg/kg memantine ($p<0.02$) but neither 30 mg/kg dextromethorphan nor 30 mg/kg ketamine ($p>0.05$) reduced the cumulative number of coughs evoked by citric acid.

As shown in FIG. 19, animals pretreated intraperitoneally with 10 mg/kg memantine, or 30 mg/kg dextromethorphan or ketamine were subjected to citric acid induced coughing. Compared to controls, memantine treated animals showed reduced cumulative numbers of coughs compared to controls and dextromethorphan or ketamine treated animals. At these doses, the dextromethorphan and ketamine treated animals showed moderate to severe sedation in the majority of animals studied. In contrast, the memantine treated animals, which showed substantially reduced levels of citric acid evoked coughing, showed no sedating effects (FIG. 20). Thus, relatively low doses of memantine, compared to dextromethorphan or ketamine, have substantially higher antitussive effects without sedation.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. An antitussive oral lozenge comprising:
   about 6-35 mg of memantine, or a pharmaceutically acceptable salt thereof;
   menthol;
   an alkalinizing agent comprising sodium carbonate and sodium bicarbonate at a weight ratio of about 1:1 to about 1:10, in an amount sufficient to raise the pH of the oral cavity, after buccal or sublingual administration, to a pH of 7.8 or higher for at least about 2 minutes; and
   one or more excipients selected from the group consisting of a binder, one or more sugar or sugar substitutes, a filler, a disintegrant, a lubricant, and combinations thereof;
   wherein after a single buccal or sublingual administration to a patient, said oral lozenge provides:
   i) a memantine $T_{max}$ ranging from about 15 minutes to about 5.5 hours;
   ii) a memantine $C_{max}$ ranging from about 1 ng/mL to about 2.5 ng/mL per mg dosed;
   iii) a memantine $AUC_{0-\infty}$ ranging from about 600 ng-hr/mL to about 5,000 ng-hr/mL and;
   iv) an absorption rate of memantine that is higher than the absorption rate of said composition that does not include an alkalinizing agent.

2. The antitussive oral lozenge of claim 1, wherein the buccal permeability of memantine is about $3.5 \times 10^{-7}$ cm/sec to about $8.25 \times 10^{-6}$ cm/sec, when tested ex vivo in porcine buccal mucosa.

3. The antitussive oral lozenge of claim 1, wherein the excipients comprise microcrystalline cellulose, magnesium stearate, starch and mannitol.

4. The antitussive oral lozenge of claim 1, wherein the lozenge is substantially free of pharmaceutically active ingredients other than memantine and menthol.

5. The antitussive oral lozenge of claim 1, further comprising one or more additional pharmaceutically active ingredients selected from the group consisting of antitussives other than memantine, expectorants, mucolytics, decongestants, nasal decongestants, first generation antihistamines, antihistamines, opioid analgesics, non-opiate analgesics, antipyretics, and combinations thereof.

6. The antitussive oral lozenge of claim 5, wherein the one or more additional pharmaceutically active ingredients are selected from the group consisting of guaifenesin, ambroxol, a first generation antihistamine, and combinations thereof.

7. The antitussive oral lozenge of claim 6, wherein the one or more additional pharmaceutically active ingredients comprise a first generation antihistamine.

8. The antitussive oral lozenge of claim 1, wherein the total weight of the lozenge is up to about 2.8 grams.

9. A method of treating cough, comprising administering the antitussive lozenge of claim 1 to the oral cavity of a patient in need thereof.

10. A method of treating cough of claim 9, wherein the oral administration is buccal administration.

11. A method of treating cough of claim 9, wherein the oral administration is sublingual administration.

12. The method of treating cough of claim 9, wherein the memantine dose is about 0.01-0.5 mg/kg.

13. The antitussive oral lozenge of claim 1, wherein after a buccal or sublingual single administration to a patient, said oral lozenge provides: a memantine $T_{max}$ ranging from about 15 minutes to about 1.5 hours.

14. The antitussive oral lozenge of claim 1, wherein after a buccal or sublingual single administration to a patient, said oral lozenge provides: a memantine $T_{max}$ ranging from about 1.5 hours to about 5.5 hours.

15. The antitussive oral lozenge of claim 1, wherein after a buccal or sublingual single administration to a patient, said oral lozenge provides: a memantine $T_{max}$ ranging from about 15 minutes to about 3 hours.

16. The antitussive oral lozenge of claim 1, wherein said antitussive lozenge further provides a buccal permeability rate of memantine that is higher than the buccal permeability rate of said lozenge that does not include an alkalinizing agent.

* * * * *